US007951787B2

(12) United States Patent  
McGuigan

(10) Patent No.: US 7,951,787 B2  
(45) Date of Patent: May 31, 2011

(54) PHOSPHORAMIDATE COMPOUNDS AND METHODS OF USE

(75) Inventor: Christopher McGuigan, Cardiff (GB)

(73) Assignee: Cardiff Protides Limited, Carmarthen (GB)

( * ) Notice: Subject to any disclaimer, the term of this patent is extended or adjusted under 35 U.S.C. 154(b) by 735 days.

(21) Appl. No.: 10/560,887

(22) PCT Filed: Jul. 20, 2004

(86) PCT No.: PCT/GB2004/003148  
§ 371 (c)(1),  
(2), (4) Date: Dec. 15, 2005

(87) PCT Pub. No.: WO2005/012327  
PCT Pub. Date: Feb. 10, 2005

(65) Prior Publication Data  
US 2006/0142238 A1   Jun. 29, 2006

(30) Foreign Application Priority Data  
Jul. 21, 2003 (GB) .................................. 0317009.9

(51) Int. Cl.  
*A01N 43/04* (2006.01)  
*A61K 31/70* (2006.01)  
*C07H 19/04* (2006.01)  
*C07H 19/10* (2006.01)

(52) U.S. Cl. ........... 514/49; 536/26.1; 536/26.8; 514/43

(58) Field of Classification Search .................. None  
See application file for complete search history.

(56) References Cited

U.S. PATENT DOCUMENTS

2003/0109697 A1* 6/2003 Shepard et al. .............. 536/26.8

FOREIGN PATENT DOCUMENTS

| JP | 2001220397 A | 8/2001 |
| JP | 2002500880 T | 1/2002 |
| WO | 9937753 A1 | 7/1999 |
| WO | WO 99/49873 | 10/1999 |
| WO | WO 01/07454 A | 2/2001 |

OTHER PUBLICATIONS

Harris et al., Antiviral Chemistry and Chemotherapy, vol. 12, 2001, pp. 293-300.*  
David B. Lackey, et al., "Enzyme-catalyzed therapeutic agent (ECTA) design: activation of the antitumor ECTA compound NB1011 by thymidylate synthase", Biochemical Pharacology, 61 (2001), pp. 179-189.  
Lisa J. Whalen, et al., "Synthesis and Evaluation of Phosphoramidate Amino Acid-Based Inhibitors of Sialyltransferases", Bioorganic & Medicinal Chemistry Letters, 13 (2003), pp. 301-304.  
Edward J. McIntee, et al., "Amino Acid Phosphoramidate Nucleosides: Potential ADEPT/GDEPT Substrates", Bioorganic & Medicinal Chemistry Letters, 11 (2001), pp. 2803-2805.

Sa Harris, et al., "Synthesis and antiviral evaluation of phosphoramidate derivatives of (E)-5-(2-bromovinyl)-2'-deoxyuridine", Antiviral Chemistry and Chemotherapy, vol. 12 (2001), pp. 293-300.  
Abraham et al., "Synthesis and Biological Activity of Aromatic Amino Acid Phosphoramidates of 5-Fluoro-2'-deoxyuridine and 1-beta-Arabinofuranosylcytosine: Evidence of Phosphoramidase Activity", J Med Chem 39:4569-4575 (1996).  
Joudka et al., "Oligonucleotides and Nucleotide-Peptides. XXXV. Some Properties of Nucleotidyl—(5'->N)-Amino Acid Esters Differing in Amino Acid and Nucleotide Components1)", J Carbohydrates Nucleosides Nucleotides 8 (1):19-39 (1981).  
Gromova et al., "Optical Rotary Dispersion and Circular Dichroism of Mono- and Oligonucleotide-Amino Acids (Amidates)", Biochim Biophys Acta 240:1-11 (1971).  
Zhou et al., "Simultaneous Formation of Peptides and Nucleotides from N-Phosphothreonine", Origins of Life and Evolution of the Bioshphere 26:547-560 (1996).  
Liorancaite et al., "Synthesis and Some Properties of Oligonucleotidyl-(Pm->N)-Serines", Nucleic Acids Symposium Series 9:215-18 (1981).  
Negishi et al., "N4-Aminocytidine, a Nucleoside Analog that has an Exceptionally High Mutagenic Activity", Nucleic Acids Research 11(15):5223-5233 (1993).  
Juodka et al., "Oligonucleotides and nucleotide-peptides. XXXVII. On the Mechanism of Hydrolysis of Uridylyl-(5'. fwdarw.N)-amino acids. Intramolecular catalysis by the .alpha.-carboxyl group of amino acids"; J Carbohydrates Nucleosides Nucleotides 8(6):519-535 (1981).  
McGuigan et al., "Systhesis and Evaluation of some masked phosphate esters of the anti-herpesvirus drug 882C (Netivudine) as potential antiviral agents", Antiviral Cheimistry & Chemotherapy 9:233-243 (1998).  
Juodka et al., "Oligonucleotides and nucleotide-peptide. XXXIV. Synthesis and some properties of complex nucleotidyl (oligonucleotidyl)-(P.fwdarw.N)-aminoacids (peptides) and their ehtyl esters"; J Carbohydrates Nucleosides Nucleotides 6(4):333-357 (1979).  
Lehsten et al., "An improved procedure for the synthesis of nucleoside amidates"; Organic Process Research & Development 6:819-822 (2002).  
Remy et al., "Studies on fluroinated pyrimidines. XIV. The synthesis of derivatives of 5-fluoro-2'-deoxyuridine 5'- phosphate and related compounds"; J Org Chem 27:2491-2500 (1962).

(Continued)

*Primary Examiner* — Traviss C McIntosh, III  
(74) *Attorney, Agent, or Firm* — Porzio, Bromberg & Newman, P.C.

(57) ABSTRACT

Phosphoramidate derivatives of nucleotides and their use in the treatment of cancer are described. The base moieties of, for example, each of deoxyuridine, cytarabine, gemcitabine and citidine may be substituted at the 5-position. The phosphoramidate moiety has attached to the P atom an aryl-O moiety and an α-amino acid moiety. The α-amino acid moiety may correspond to or be derived from either a naturally occurring or a non-naturally occurring amino acid.

22 Claims, 4 Drawing Sheets

OTHER PUBLICATIONS

Siddiqui et al., "Design and Synthesis of Lipophilic Phosphoramidate d4T-MP Prodrugs Expressing High Potency Against HIV in Cell Culture: Structural Determinants for in Vitro Activity and QSAR", J Med Chem 42 (1999), pp. 4122-4128.

Stryer, L., "DNA and RNA: Molecules of Heredity", Biochemistry, Fourth Ed., Ch. 4. pp. 75, 76, 80-83 (1995).

Stryer, L., "Flow of Genetic Information". Biochemistry, Fourth Ed., Ch. 5, pp. 95-97 (1995).

* cited by examiner

PHOSPHORAMIDATE COMPOUNDS AND METHODS OF USE

The present invention relates to nucleotide derivatives and their use in the treatment of cancer.

Nucleoside analogues such as fluorodeoxyuridine (1), cytarabine (2) and gemcitabine (3) are well established as anti-cancer agents. They function as inhibitors of DNA synthesis after activation to their 5'-phosphate form.

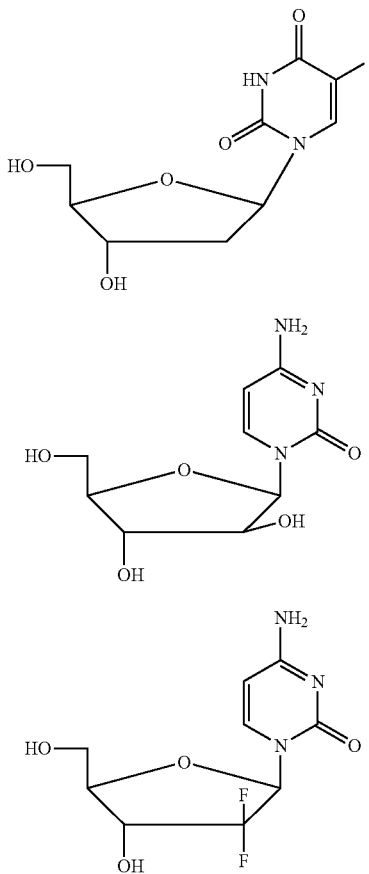

The free bioactive phosphate forms do not in general represent useful drugs due to their poor membrane permeation. In an effort to circumvent this a number of phosphate pro-drug approaches have been reported [Rosowsky et al, J. Med. Chem., 1982, 25, 171-8; Hong et al, J. Med. Chem., 1985, 28, 171-8; Kodama et al, Jpn. J. Cancer Res., 1989, 80, 679-85; Hong et al, 1979, 22, 1428-32; Ji et al, J. Med. Chem., 1990, 33, 2264-70; Jones et al, Nucleic Acids Res., 1989, 17, 7195-7201; Hunston et al, J. Med. Chem., 1984, 27, 440-4; Lorey et al, Nucleosides Nucleotides, 1997, 16, 1307-10; Farquhar et al, J. Med. Chem., 1983, 26, 1153-8; Shuto et al, Nucleosides Nucleotides, 1992, 11, 437-46; Le Bec et al, Tet. Letts., 1991, 32, 6553-6; Phelps et al, J. Med. Chem., 1980, 23, 1229-32].

In general the phosphate prodrugs have biological properties and therapeutic activities that are similar to, or somewhat lower than, the parent nucleoside analogue.

We have carried out extensive work in this area from an antiviral perspective, largely on dideoxy nucleosides, and have reported a phosphoramidate approach which has been widely adopted for the delivery of bio-active phosphates of antiviral nucleosides.

An example is the phosphoramidate (4) derived from anti-HIV d4T (5).

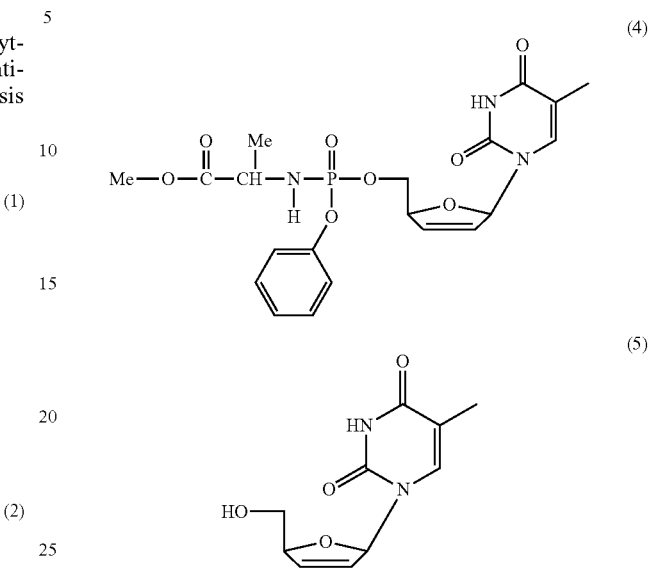

We observed the effect of variations in the ester [McGuigan et al, AVCC, 1998, 9, 473-9], amino acid [McGuigan et al, Antiviral Res., 1997, 35, 195-204; AVCC, 2000, 11, 111-6], and aryl [Siddiqui et al, J. Med. Chem., 1999, 42, 393-9] regions of the phosphoramidate, as well as the effect of amino acid stereochemistry [McGuigan et al, AVCC, 1996, 7, 184-8), phosphate stereochemistry [Allender et al, Analytica Chim. Acta, 2001, 435, 107-13] and nucleoside [Balzarini et al, BBRC, 1996, 225, 363-9; McGuigan et al, BioOrg. Med, Chem. Lett., 1996, 6, 2369-62; McGuigan et al, Bioorg. Med. Chem. Lett., 2000, 10, 645-7].

This work has lead to the optimal description of phenyl methoxyalaninyl phosphoramidate as the prototype pro-moiety for the intracellular delivery of bioactive nucleotides [Balzarini et al, PNAS, 1996, 93, 7295-9; McGuigan et al, J. Med. Chem., 1996, 39, 1748-53].

Lackey et al [Biochem Pharmacol., 2001, 61, 179-89] have reported the application of our phosphoramidate pro-drug method for antiviral nucleosides to the anti-herpetic agent bromovinyl-2'-deoxyuridine (BVDU) (6). In particular, they have found that the phenyl methoxyalaninyl phosphoramidate (7) has significant anti-cancer activity. This is in marked contrast to the parent (antiviral) nucleoside (6).

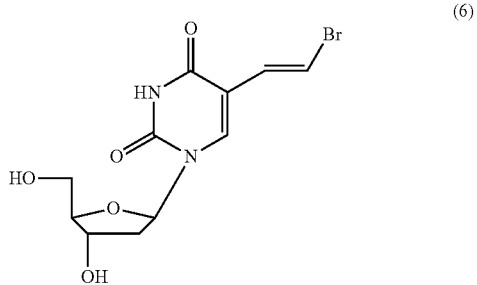

-continued

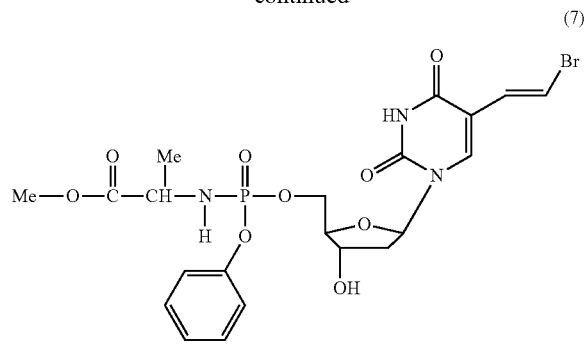
(7)

Limited SAR has been presented by this group, although in their patent applications [WO0239952, EP1200455, CA2317505, U.S. Pat. No. 6,339,151, EP116797, AU2451601] they claim a series of general variations in the base, and phosphate regions. However, based on our prior art, the phenyl methoxyalaninyl phosphoramidate (7) would be anticipated to be amongst the most optimal of structures.

Surprisingly, it has now been found that other derivatives of oxyamino acid-phosphoramidate nucleoside analogues are significantly more potent in the treatment of cancer than the phenyl methoxyalaninyl phosphoramidate (7).

According to a first aspect of the present invention there is provided a compound of formula I:

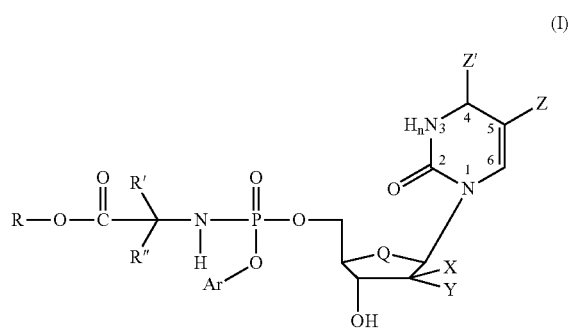
(I)

wherein:
R is selected from the group comprising alkyl, aryl and alkylaryl;
R' and R" are, independently, selected from the group comprising H, alkyl and alkylaryl, or R' and R" together form an alkylene chain so as to provide, together with the C atom to which they are attached, a cyclic system;
Q is selected from the group comprising —O— and —CH$_2$—;
X and Y are independently selected from the group comprising H, F, Cl, Br, I, OH and methyl (—CH$_3$);
Ar is a monocyclic aromatic ring moiety or a fused bicyclic aromatic ring moiety, either of which ring moieties is carbocyclic or heterocyclic and is optionally substituted;
Z is selected from the group comprising H, alkyl and halogen; and
n is 0 or 1,
wherein
when n is 0, Z' is —NH$_2$ and a double bond exists between position 3 and position 4, and
when n is 1, Z' is =O;
or a pharmaceutically acceptable derivative or metabolite of a compound of formula I;

with the proviso that when n is 1, X and Y are both H, R is methyl (—CH$_3$), one of R' and R" is H and one of R' and R" is methyl (—CH$_3$), then Ar is not phenyl (—C$_6$H$_5$).

By "a pharmaceutically acceptable derivative" is meant any pharmaceutically acceptable salt, ester or salt of such ester or any other compound which upon administration to a recipient is capable of providing (directly or indirectly) a compound of formula (I).

Suitably, except where R is 2-Bu (—CH$_2$—CH(CH$_3$)$_2$) and one of R' and R" is H and one of R' and R" is methyl (—CH$_3$), when n is 1 and X and Y are both H, then Ar is not unsubstituted phenyl (—C$_6$H$_5$).

By "pharmaceutically acceptable metabolite" is meant a metabolite or residue of a

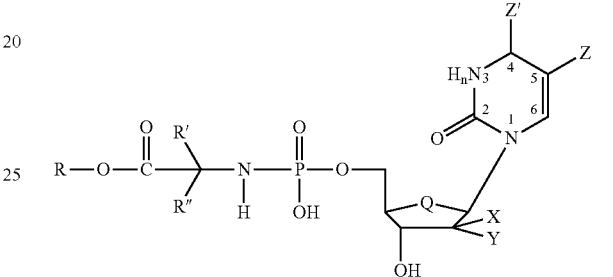
(II)

compound of formula (I) which gives rise in use to a compound of formula (II):
wherein n, Q, R, R', R", X, Y, Z and Z' have the meanings described above and below for formula I, and additionally R can be H, with the proviso that when n is 1, X and Y are both H, R is methyl (—CH$_3$), one of R' and R" is H and one of R' and R" is methyl (—CH$_3$), then Z is not —CH=CHBr.

Suitably, with respect to compounds of formula II, when n is 1 and Z either is or is not —CH=CHBr, the moiety ROCOCR'R"NH— corresponds neither to alanine (ie as above, R is not methyl (—CH$_3$), one of R' and R" is not H and one of R' and R" is not methyl (—CH$_3$)) nor to tryptophan (ie α-amino-β-indolylpropionic acid).

More suitably with respect to compounds of formula II, when n is 1 and Z either is or is not —CH=CHBr, the moiety ROCOR'R"NH is neither derived from nor corresponds to any naturally occurring amino acid.

Even more suitably, with respect to compounds of formula II, when n is 1 or 0, the moiety ROCOCR'R"NH— does not correspond to alanine (ie R is not methyl (—CH$_3$), one of R' and R" is is not H and one of R' and R" is not methyl (—CH$_3$)), does not preferably correspond to tryptophan, and even more preferably the said moiety does not correspond to any naturally occurring amino acid.

Most preferably the moiety ROCOCR'R"NH— in compounds of formula II corresponds to a non-naturally occurring amino acid.

Reference in the present specification to an alkyl group means a branched or unbranched, cyclic or acyclic, saturated or unsaturated (e.g. alkenyl or alkynyl) hydrocarbyl radical. Where cyclic, the alkylene group is preferably C$_3$ to C$_{12}$, more preferably C$_5$ to C$_{10}$, more preferably C$_5$ to C$_7$. Where acyclic, the alkyl group is preferably C$_1$ to C$_{16}$, more preferably C$_1$ to C$_6$.

Reference in the present specification to an aryl group means an aromatic group containing 5 to 14 ring atoms, for example phenyl or naphthyl. The aromatic group may be a heteroaromatic group containing one, two, three or four, preferably one, heteroatoms selected, independently, from the group consisting of O, N and S. Examples of such heteroaromatic groups include pyridyl, pyrrolyl, furanyl and thiophenyl. Preferably, the aryl group comprises phenyl or substituted phenyl.

The alkyl and aryl groups may be substituted or unsubstituted. Where substituted, there will generally be one to three substituents present, preferably one substituent. Substituents may include halogen atoms, by which is meant F, Cl, Br and I atoms, and halomethyl groups such as $CF_3$ and $CCl_3$; oxygen containing groups such as oxo, hydroxy, carboxy, carboxy$C_{1-16}$alkyl, alkoxy, alkoyl, alkoyloxy, aryloxy, aryloyl and aryloyloxy; nitrogen containing groups such as amino, $C_{1-6}$alkylamino, di$C_{1-6}$alkylamino, cyano, azide and nitro; sulphur containing groups such as thiol, $C_{1-6}$alkylthiol, sulphonyl and sulphoxide; heterocyclic groups which may themselves be substituted; alkyl groups as defined above, which may themselves be substituted; and aryl groups as defined above, which may themselves be substituted, such as phenyl and substituted phenyl. Substituents on said heterocyclic, alkyl and aryl groups are as defined immediately above.

Reference in the present specification to alkoxy and aryloxy groups means, respectively, alkyl-O— (for example where alkyl is $C_1$ to $C_{16}$, preferably $C_1$ to $C_6$) and aryl-O— (for example where aryl is a 5 to 14 membered aromatic mono- or bifused ring moiety, optionally containing 1, 2, 3 or 4 heteroatoms selected, independently, from O, S and N, preferably aryl is phenyl).

Reference in the present specification to alkoyl and aryloyl groups means, respectively, alkyl-CO— (for example where alkyl is $C_1$ to $C_{16}$, preferably $C_1$ to $C_6$) and aryl-CO— (for example where aryl is a 5 to 14 membered aromatic mono or bifused ring moiety, optionally containing 1, 2, 3 or 4 heteroatoms selected, independently, from O, S and N, preferably aryl is phenyl).

Reference in the present specification to alkoyloxy and aryloyloxy means, respectively, alkyl-CO—O (for example where alkyl is $C_1$ to $C_{16}$, preferably $C_1$ to $C_6$) and aryl-CO—O (for example where aryl is a 5 to 14 membered mono- or bifused aromatic ring system, optionally containing 1, 2, 3 or 4 heteroatoms selected, independently, from O, S and N, preferably aryl is phenyl).

Reference in the present specification to heterocyclic groups means groups containing one or more, pyrrolyl, imidazolyl, pyraziolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronly, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

The group Ar comprises a substituted or unsubstituted aryl group, wherein the term "aryl group" and the possible substitution of said group is as defined herein. Preferably, Ar is a substituted or unsubstituted phenyl group. Particularly preferred substituents are electron withdrawing groups such as halogen (preferably chlorine or fluorine), trihalomethyl (preferably trifluoromethyl), cyano and nitro groups. For example, Ar can be phenyl, 3,5-dichloro-phenyl, p-trifluoromethyl-phenyl, p-cyano-phenyl, or p-nitro-phenyl. When Ar is a heteroaromatic group, preferably it is optionally substituted pyridyl.

Suitably, R is a $C_{1-16}$ primary or secondary alkyl group, a $C_{5-7}$ carbocyclic aryl group or a $C_{1-6}$alkyl$C_{5-11}$aryl group. More suitably, R is a $C_{1-10}$ alkyl group, a phenyl group or $C_{1-3}$ alkyl$C_{5-7}$ aryl group. Preferably R is unsubstituted.

Preferably, R is methyl (—$CH_3$), ethyl (—$C_2H_5$), n- or i-propyl (—$C_3H_7$), n- or i-butyl (—$C_4H_9$) or benzyl (—$CH_2C_6H_5$). Most preferably, R is benzyl. Particularly, R is preferably benzyl when one of R' and R" is H and one of R' and R" is methyl (—$CH_3$), especially when Ar is unsubstituted phenyl, n is 0 and each of X and Y is F.

Suitably, R' and R" are each independently selected from the group comprising H, $C_{1-6}$ primary, secondary or tertiary alkyl, $C_{1-3}$alkyl$C_{5-7}$aryl, or, when together they form an alkylene chain, they provide, together the C atom to which they are attached, a $C_{3-8}$ carbocyclic aliphatic ring.

Preferably, R' and R" are the same and are alkyl, more preferably they are both methyl, ethyl or n- or i-propyl.

Alternatively, preferably, R' and R" are, independently, H, methyl (—$CH_3$), secondary butyl (—$CH_2$—CH—($CH_3$)$_2$), benzyl (—$CH_2C_6H_5$), or, together with the C atom to which they are attached, provide a $C_{5-6}$ ring.

Preferred compounds include those where R' and R" are both methyl, one of R' and R" is H and one of R' and R" is methyl, and R' and R", together with the C atom to which they are attached, provide a pentyl ring.

When R' and R" are different, the C atom to which they are attached is chiral. The present compounds can be L or D or a mixture of stereoisomers. Preferably they are L.

It will be appreciated that the moiety —O—C(O)—CR'R"—NH— corresponds to a carboxy-protected α-amino acid. R' and R" can thus correspond to the side chains of a naturally occurring amino acid.

For example, when one of R' and R" is H and one of R' and R" is Me or PhCH$_2$, the moiety corresponds to alanine or phenylalanine, respectively.

Preferably, the stereochemistry at the asymmetric centre —CR'R" corresponds to an L-amino acid. The stereochemistry at the asymmetric centre —CR'R" can, however, correspond to a D-amino acid. Alternatively, mixtures of of compounds can be employed having asymmetric centres corresponding to L and D amino acids.

In the present specification by "naturally occurring amino acid" we mean Alanine, Arginine, Asparagine, Aspartic Acid, Cysteine, Cystine, Glycine, Glutamic Acid, Glutamine, Histidine, Hydroxylysine, Hydroxyproline, Isoleucine, Leucine, Lysine, Methionine, Phenylalanine, Proline, Serine, Threonine, Tryptophan, Tyrosine and Valine.

The present invention is not, however, limited to compounds having a moiety corresponding to a naturally occurring amino acid. The present invention specifically includes compounds having a moiety which corresponds to a non-naturally occurring amino acid, such as, for example, those where R'=R"=alkyl, or, where together with the C atom to which they are attached, R' and R" provide a cyclic moiety. Preferably with respect to the compound of formula I, the moiety ROCOCR'R"NH— corresponds to or is derived from a non-naturally occurring amino acid.

With respect to compounds of formula I when n is 1, the moiety ROCOCR'R"NH— preferably neither corresponds to nor is derived from alanine, more preferably neither corresponds to nor is derived from either of alanine or tryptophan, even more preferably neither corresponds to nor is derived from any naturally occurring amino acid.

With respect to compounds of formula I when n is 0, the moiety ROCOCR'R"NH— preferably neither corresponds to nor is derived from alanine, more preferably neither corresponds to nor is derived from either of alanine or trytophan, even more preferably neither corresponds to nor is derived from any naturally occurring amino acid.

Preferably Q is O.

Preferably, X and Y are, independently, selected from the group comprising F, H and OH.

When n is 1, preferably each of X and Y is H.

When n is 0, preferably each of X and Y is F, or X is OH and Y is H, or X is H and Y is OH.

When Z is F, Q is O, n is 1 and X and Y are each H, the base moiety of the compound of formula I corresponds to that of fluorodeoxyuridine i.e. compound (1) above.

When Z is H, Q is O, n is 0 and X is OH and Y is H, the base moiety of the compound of formula I corresponds to that of cytarabine i.e. compound (2) above.

When Z is H, Q is O, n is 0 and X and Y are each F, the base moiety of the compound of formula I corresponds to that of gemcitabine i.e. compound (3) above.

When Z is H, Q is O, n is 0 and X is H and Y is OH, the base moiety of the compound of formula I corresponds to that of cytidine.

Compounds of formula I wherein n is 0 and X and Y are F are preferred. Particularly preferred are compounds of formula I wherein n is 0, X and Y are F, Q is O and Z is H, corresponding to phosphoramidated gemcitabine.

Also preferred are compounds of formula I wherein n is 0 and X is OH and Y is H. Particularly preferred are compounds of formula I wherein n is 0, X is OH, Y is H, Q is O and Z is H, corresponding to phosphoramidated cytarabine.

Also preferred are compounds of formula I wherein n is 0 and X is H and Y is OH. Particularly preferred are compounds of formula I wherein n is 0, X is H, Y is OH, Q is O and Z is H, corresponding to phosphoramidated cytidine.

Suitably, Ar is a 5 to 14 membered aromatic ring moiety. The one or two rings may include 1, 2, 3 or 4 heteroatoms, preferably 1, selected, independently, from O, S and N.

Preferably, Ar is a carbomonocyclic aromatic ring moiety. More preferably, Ar is a $C_6$ monocyclic aromatic ring moiety, ie is optionally substituted phenyl.

One, two, three or four substituents, which may be the same or different, may be present on Ar and are selected from the group comprising halogen, which may —F, —Cl, —Br or —I; —NO$_2$; —NH$_2$; optionally substituted —C$_{1-3}$alkyl; optionally substituted —C$_{1-3}$alkoxy, preferably methoxy (—OCH$_3$); optionally substituted —SC$_{1-3}$alkyl; —CN; optionally substituted —COC$_{1-3}$alkyl; and optionally substituted —CO$_2$C$_{1-3}$alkyl. The optional substitutents are one or more up to six, preferably three, members selected from the group comprising halogen which may be F, Cl, Br and I and NO$_2$. Preferred substituents on Ar include F, Cl, CF$_3$, and NO$_2$.

The substituents may be at any position on the ring moiety. Where the ring moiety is $C_6$ ie phenyl, a single substituent at the 2 (ortho) or 4 (para) position is preferred. Where Ar is phenyl, a single substituent at the 4 position is more preferred.

Preferably, Ar is an optionally substituted phenyl moiety. More preferably, Ar is selected form the group comprising: Ph—, pCF$_3$C$_6$H$_4$—, pFC$_6$H$_4$—, pNO$_2$C$_6$H$_4$—, pClC$_6$H$_4$— and oClC$_6$H$_4$—.

Suitably, Z is selected from the group comprising H, C$_{1-6}$ alkyl, substituted C$_{1-6}$ alkyl, C$_{1-6}$ alkenyl, substituted C$_{1-6}$ alkenyl, C$_{1-6}$ alkynyl, substituted C$_{1-6}$ alkynyl and halogen, where halogen is F, Cl, Br or I. Substituents that may be present on the alkenyl or alkynyl moiety are selected from the group comprising F, Cl, Br, I, and —CO$_2$Me. One, two or three substituents may be present. The alkenyl and alkynyl groups may contain one or more sites of unsaturation.

Where Z is substituted alkenyl or alkynyl, the substituent is preferably on the terminal C atom.

Preferably Z is selected from the group comprising H, F, optionally substituted C$_{1-6}$alkyl particularly Me (—CH$_3$), optionally substituted C$_{1-6}$alkenyl and optionally substituted C$_{1-6}$alkynyl, the optional substituents being as recited immediately above.

When n is 1, Z' is O, Q is O and X and Y are each H, preferably Z is a substituted C$_2$ alkenyl (i.e. ethenyl or vinyl) moiety (—CH=CH—); more preferably, Z is bromovinyl (—CH=CHBr) or methylpropenoate (—CH=CHCO$_2$Me); and most preferably, Z is —CH=CHBr.

With respect to compounds of formula II, preferably when n is 1 and X and Y are both H, then Z is not F.

With respect to compounds of formula II, when n is 0, preferably X is not H and Y is not OH, more preferably X is OH and Y is H or X and Y are both F.

With respect to compounds of formula II, when n is 0, X is OH and Y is H, preferably neither R' nor R" is phenylmethyl (ie benzyl) or 3-methylindolyl (ie 3-CH$_2$indolyl).

Surprisingly, modifying the ester moiety in compound (7) has been found to show a marked increase in potency with respect to cancer cell lines. A preferred compound embodying the present invention is the benzyl ester (8). It has surprisingly been found that the benzyl ester (8) is very significantly more potent against several cancer cell lines than the methyl ester (7):

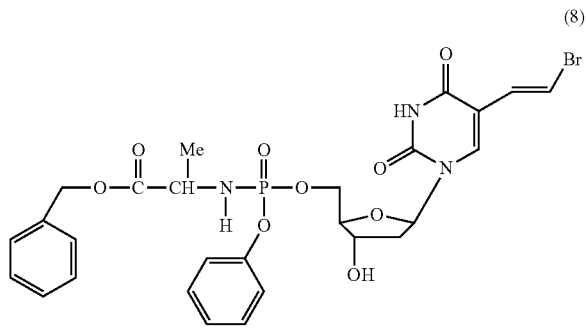

(8)

Compound (8) inhibits the growth of colon cancer cell line HT115 by 50% at 1.4 µM, whilst (7) requires a concentration of 244 µM; (8) is thus 174 times more potent. Compound (8) is also 8 times more potent than (7) versus prostate cancer cell line PC-3 (19 µM vs. 155 µM).

The degree of potency enhancement for (8) vs. (7) is surprising based on the prior art. Thus, comparing the equivalent phosphoramidates of d4T reveals a ca 4-fold potency boost of (10) over (9) [McGuigan et al, AVCC, 1998, 9, 473-9].

(9)

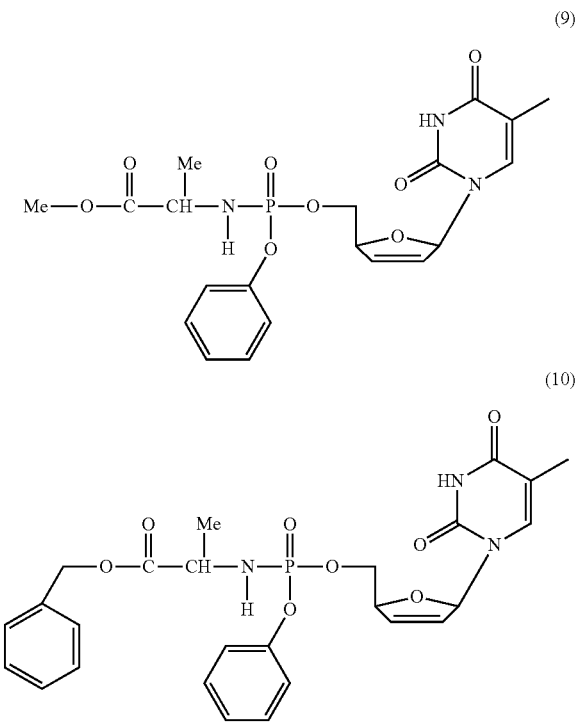

(10)

This would imply that the benzyl phosphoramidate motif in (10) is ca 4-fold more efficient at the intracellular delivery of the bio-active free phosphate forms of d4T than is the methyl ester (9). A person skilled in the art would anticipate a similar degree of enhancement for the benzyl phosphoramidate of BVDU (8) over the methyl ester (7) whilst we observed an almost 200-fold enhancement for colon cancer as noted above.

Surprising efficacy of modifications in the amino acid and aryl moieties of the BVDU phosoramidate has also been found in compounds embodying the present invention.

Thus, compound (11) has simultaneous modification in these two regions, being the p-trifluoromethylphenyl benzyl [α,α-dimethylglycinyl]phosphoramidate.

(11)

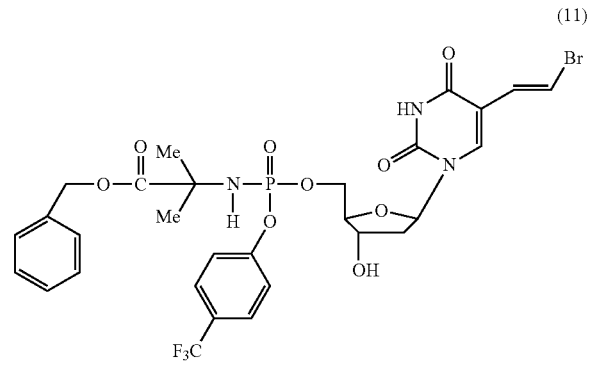

Compound 11 shows high potency against a range of cancer cell types and is significantly and surprisingly more potent than (7). Thus, for breast cancer (11) is 60-fold more active (1.3 μM vs 79 μM), and for prostate cancer (11) is 254-fold more potent (0.61 μM vs. 155 μM). Against colon cancer, (11) is 35-fold more potent (7 μM vs 244 μM). Again, the degree of enhancement of the analogue (11) vs. (7) is surprising based on prior art. Thus, comparing (12) [dimethyl glycine modification] and (13) [p-CF$_3$phenyl modification] to (9) shows no significant difference in potency.

(12)

(13)

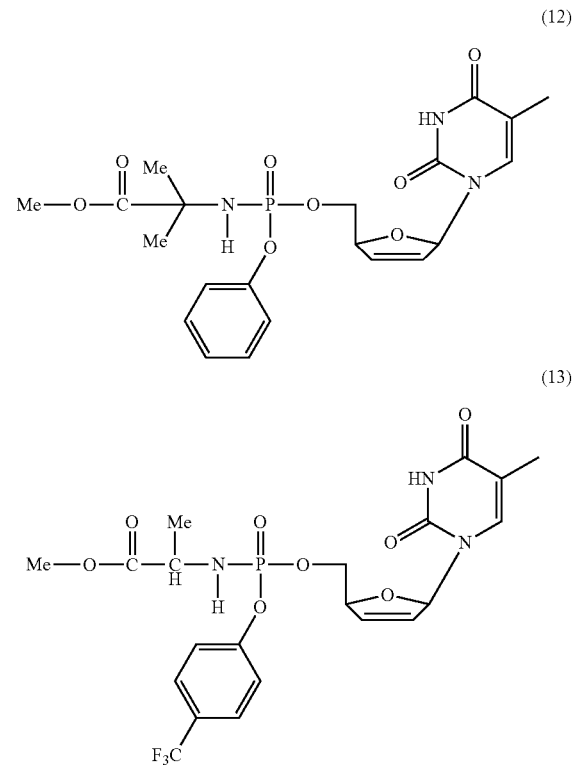

Thus 50% effective doses vs HIV-1 for (9), (12) and (13) are: 0.075, 0.29, and 0.01 μM respectively; within experimental error, (12) and (13) are identical in potency to (9). Thus a person skilled in the art would have predicted that (11) would show little enhancement over (7) as opposed to the 35 to 254-fold enhancements noted above.

Thus, compounds embodying the present invention and having variations in one or more of the ester (R), amino acid (R', R") and aryl (Ar) region of the phosphoramidate structure compared to phenyl methoxyalaninyl phosphoramidate can give surprising and substantial potency boosts of pro-tides derived from BVDU against a range of cancer cell types.

According to a further aspect of the present invention there is provided a compound having formula I according to the present invention for use in a method of treatment, preferably in the prophylaxis or treatment of cancer.

According to a further aspect of the present invention there is provided a method of phrophylaxis or treatment of cancer comprising administration to a patient in need of such treatment an effective dose of a compound having formula I according to the present invention.

According to a further aspect of the present invention there is provided use of a compound having formula I of the present invention in the manufacture of a medicament for use in the treatment or prophylaxis of cancer.

According to a further aspect of the present invention there is provided a pharmaceutical composition comprising a compound having formula I of the present invention in combination with a pharmaceutically acceptable excipient, carrier or diluent.

According to a further aspect of the present invention there is provided a method of preparing a pharmaceutical composition comprising the step of combining a compound having formula I of the present invention with a pharmaceutically acceptable excipient, carrier or diluent.

The present invention is particularly applicable for the treatment of a patient having breast cancer, colon cancer or prostate cancer. Examples of such cancers include breast MDA MB231, colon HT115 and prostate PC-3.

The compound having formula I or pharmaceutical composition according to the present invention can be administered to a patient, which may be human or animal, by any suitable means.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day. A preferred lower dose is 0.5 mg per kilogram body weight of recipient per day, a more preferred lower dose is 6 mg per kilogram body weight of recipient per day, an even more preferred lower dose is 10 mg per kilogram body weight per recipient per day. A suitable dose is preferably in the range of 6 to 150 mg per kilogram body weight per day, and most preferably in the range of 15 to 100 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

According to a further aspect of the present invention there is provided a process for the preparation of a compound having formula I according to the present invention, the process 30 comprising reacting of a compound of formula (III):

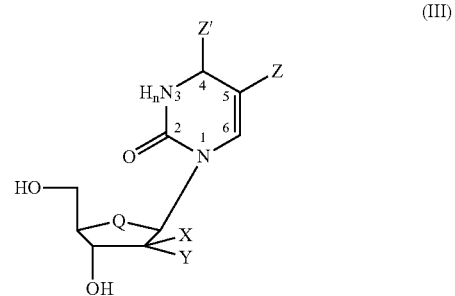

with a compound of formula (IV):

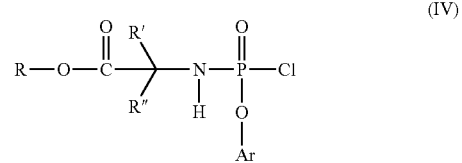

wherein Ar, n Q, R, R', R", X, Y, Z' and Z have the meanings described above with respect to formula (I).

Embodiments of the present invention will now be described, by way of example only, with reference to the following examples, experimental procedures and experimental data.

Data are presented for a range of structures against tumour cell types representing a range of common cancers in man with un-met clinical need: breast MDA MB231, colon HT115, prostate PC-3. Data from these assays are presented as Table 1.

EXPERIMENTAL PROCEDURE

General Methods

The following anhydrous solvents and reagents were bought from Aldrich with sure stopper: dichloromethane (DCM), diethyl ether ($Et_2O$), tetrahydrofuran THF), N-methylimidazole (NMI), methanol (MeOH), dimethylformamide (DMF), 1,4-dioxane. triethylamine was dried on molecular sieves of 4 Angstrom.

Thin Layer Chromatography

Thin layer chromatography (TLC) was performed on commercially available Merck Kieselgel 60 $F_{254}$ plates and separated components were visualized using ultraviolet light (254 nm and 366 nm).

Column Chromatography

Columns were performed using (Kieselgel 60, 35-70 μm, Fluka) as the stationary phase. Samples were applied as a concentrated solution in the same eluent, or pre-adsorbed onto silica gel.

NMR Spectroscopy $^1$H, $^{13}$C and $^{31}$P-NMR were recorded on a Bruker Avance DPX300 spectrometer with operating frequencies of 300 MHz, 75 MHz and 121 MHz respectively. $^{31}$P-NMR spectra are reported in units of δ relative to 85% phosphoric acid as external standard, positive shifts are downfield. The following abbreviations are used in the assignment of NMR signals: s (singlet), d (doublet), t (triplet), q (quartet), m (multiplet), bs (broad signal), dd (doublet of doublet), dt (doublet of triplet). Starred signal signal are splitted due to stereoisomeric mixtures.

Standard Procedures

For practical purposes, standard procedures are given where applicable.

Standard Procedure 1: Synthesis of Amino Ester Hydrochloride Salts.

To a stirring solution of anhydrous alcohol (10 mol eq.) was added thionyl chloride (2 mol eq.) at 0° C., and the resulting solution stirred for 1 hr. After warming to room temperature, the appropriate amino acid (1 mol eq) was added and the reaction heated at reflux for 6-16 hrs. Removal of solvent and recrystallisation from methanol/ether gave the amino ester hydrochloride salts.

Standard Procedure 2: Synthesis of Amino Benzyl Ester Hydrochloride Salts.

The appropriate amino acid (1.0 mol eq.), p-toluene sulfonic acid (1.0 mol eq.) and anhydrous benzyl alcohol (4.1 mol eq.) were heated at reflux in toluene (10 mol eq.) with Dean-Stark trap for 24 hrs. On cooling to room temperature, Et$_2$O was added and the mixture was left in ice bath for 1 hr then filtrated and washed with Et$_2$O. The solid was dissolved in DCM and washed with 10% K$_2$CO$_3$ and water. The organic layer was dried over MgSO$_4$, filtered and the solvent removed under reduced pressure to give an oil. This was solubilized in acetone and neutralized with 1 M HCl. Et$_2$O was added and the solid was filtered and washed with Et$_2$O to give a white solid.

Standard Procedure 3: Synthesis of Phosphorodichloridate Species.

Phosphorus oxychloride (1.0 mol eq.) and the appropriate substituted phenol (1.0 mol) were stirred with anhydrous diethylether (31 mol eq.). To this was added anhydrous triethylamine (1.0 mol eq) at −80° C. and left to rise to room temperature over 16 hrs the triethylamine hydrochloride salt was filtered off, and the filtrate reduced to dryness to give the crude product as a clear liquid.

Standard Procedure 4: Synthesis of Phosphochloridate Species.

Phosphodichloridate (1.0 mol eq.) and the appropriate amino ester hydrochloric salt (1.0 mol eq.) were suspended in anhydrous DCM. Anhydrous triethylamine was added dropwise at −80° C. and after 1 hr the reaction was left to rise to room temperature. The formation of phosphochloridate was monitored by $^{31}$P-NMR. After 2-5 hrs the solvent was removed under reduced pressure and the solid obtained washed with anhydrous ether (2×20 ml), filtered, and the filtrate reduced to dryness to give the products as crude oil. These oils were usually used without further purification.

Standard Procedure 5: Synthesis of Phosphoroamidate Derivatives.

To a stirring solution of (E)-5-(2-bromovinyl)-2'-deoxyuridine (1.0 mol eq.) and the appropriate phosphochloridate (2.0-3.0 mol eq) in anhydrous THF at −80° C. was added dropwise over 1 min NMI (5.0 mol eq.). After 15 mins the reaction was left to rise to room temperature and stirred at room temperature for 2-19 hrs. The solvent was removed under reduced pressure and the yellow oil obtained was dissolved in DCM, washed with 0.5 M HCl, and water. The organic layer is dried over MgSO$_4$, filtered, reduced to dryness and purified by flash chromatography (Chloroform/Methanol 97/3, Dichloromethane/Methanol 97/3).

Synthesis of Methyl-1-amino-1-cyclopentanoate hydrochloride salt

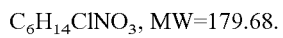

This was synthesised according to Standard Procedure 1, using 1-amino-1-cyclopentanecarboxylic acid (3.876 g, 30 mmol) with thionyl chloride (4.44 mL, 45 mmol,) and anhydrous methanol (15.5 mL). The product was isolated as a white solid (4.81 g, yield 89%).

$^1$H-NMR (CDCl$_3$; 300 MHz): δ 9.1 (3H, bs, NH$_3$$^+$Cl$^-$), 3.85 (3H, s, OCH$_3$), 2.3-2.2 (4H, m, 4H cyclopentane), 2.15 (2H, 2H cyclopentane), 1.95 (2H, m, 2H cyclopentane).

$^{13}$C-NMR (CDCl$_3$; 75 MHz): δ 26.6 (2$\underline{CH_2}$ cyclopent), 38.1 (2$\underline{CH_2}$ cyclopent), 54.8 ($\underline{CH_3}$O), 66.6 ($\underline{C}$q cyclopentane), 174.1 ($\underline{C}$OOMe).

Synthesis of Ethyl-1-amino-1-cyclopentanoate hydrochloride salt

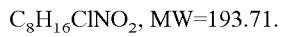

This was synthesised according to Standard Procedure 1, using 1-amino-1-cyclopentanecarboxylic acid (5.0 g, 38.6 mmol) with thionyl chloride (5.72 mL, 58 mmol) and anhydrous ethanol (29 mL). The product was isolated as a white solid (6.98 g, yield 93%).

$^1$H-NMR (CDCl$_3$; 300 MHz): δ 9.0 (3H, bs, NH$_3$$^+$Cl$^-$), 4.3 (2H, q, $^3$J=8, OCH$_2$CH$_3$), 2.3-2.2 (4H, m, 4H cyclopentane), 2.15 (2H, 2H cyclopentane), 1.95 (2H, m, 2H cyclopentane), 1.4 (3H, t, $^3$J=8, OCH$_2$CH$_3$).

$^{13}$C-NMR (CDCl$_3$; 75 MHz): δ 14.5 (CH$_3$$\underline{CH_2}$), 25.8 (2$\underline{CH_2}$ cyclopent), 37.4 (2$\underline{CH_2}$ cyclopent), $\overline{63.0}$ ($\underline{CH_3}$CH$_2$), 66.2 ($\underline{C}$q cyclopentane), 172.1 ($\underline{C}$OOEt).

Synthesis of Benzyl-1-amino-1-cyclopentanoate hydrochloride salt $C_{14}H_{18}ClNO_2$, MW=255.78.

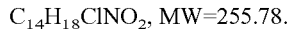

This was synthesised according to Standard Procedure 2, using 1-amino-1-cyclopentanecarboxylic acid (3.682 g, 28.5 mmol) with p-toluene sulfonic acid monohydrate (5.625 g, 29.55 mmol) and anhydrous benzylic alcohol (12 mL, 116 mmol), in Toluene (20 mL). The product was isolated as a white solid (6.441 g, yield 88.5%) Hydrochloride salt.
$^1$H-NMR (CDCl$_3$; 300 MHz): δ 9.05 (3H, bs, NH$_3^+$Cl$^-$), 7.4-7.25 (5H, m, Ph), 5.15 (2H, s, CH$_2$Ph), 2.3 (4H, m, 4H cyclopentane), 2.15 (2H, 2H cyclopentane), 1.95 (2H, m, 2H cyclopentane).

$^{13}$C-NMR (CDCl$_3$; 75 MHz): δ 25.9 (2CH$_2$ cyclopent), 37.3 (2CH$_2$ cyclopent), 66.3 (Cq cyclopentane), 68.3 (CH$_2$Ph), 129.2, 129.0, 128.8 ('o', 'm', CH$_2$Ph), 135.5 ('p', CH$_2$Ph), 172.1 (COOBn).

Synthesis of methyl-2-amino-2-methylpropanoate hydrochloride salt

C$_5$H$_{12}$ClNO$_3$, MW 153.61.

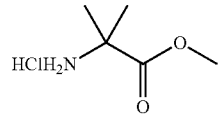

This was synthesised according to Standard Procedure 1, using 2-amino-isobutyric acid (5.102 g, 48.49 mmol) with thionyl chloride (11.538 g, 96.98 mmol, 7.04 mL) and anhydrous methanol (19.6 mL). The product was isolated as a white solid (6.636 g, yield 89.2%).

$^1$H-NMR (CDCl$_3$; 300 MHz): δ 8.81 (3H, bs, NH$_3$Cl), 3.83 (3H, s, OCH$_3$), 1.74 (6H, s, [CH$_3$]$_2$C).

$^{13}$C-NMR (CDCl$_3$; 75 MHz): δ 24.1, 24.3 ([CH$_3$]$_2$C), 57.9 (C[CH$_3$]$_2$), 172.4 (COOCH$_3$).

Synthesis of ethyl-2-amino-2-methylpropanoate hydrochloride salt

C$_6$H$_{14}$ClNO$_2$, MW 167.63.

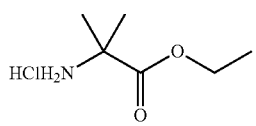

This was synthesised according to Standard Procedure 1, using 2-amino-isobutyric acid (5.102 g, 48.49 mmol) with thionyl chloride (11.772 g, 98.95 mmol, 7.2 mL) and anhydrous ethanol (29 mL). The product was isolated as a white solid (7.159 g, yield 86.3%).

$^1$H-NMR (CDCl$_3$; 300 MHz): δ 8.93 (3H, bs, NH$_2$Cl), 4.3 (2H, q, $^3$J=7.1 Hz, OCH$_2$CH$_3$), 1.75 (6H, s, [CH$_3$]$_2$C), 1.33 (3H, t, $^3$J=7.1 Hz, OCH$_2$CH$_3$).

$^{13}$C-NMR (CDCl$_3$; 75 MHz): δ 14.4 (CH$_3$CH$_2$O), 24.3 ([CH$_3$]$_2$C), 57.9 (C[CH$_3$]$_2$), 63.1 (OCH$_2$CH$_3$), 171.6 (COOCH$_2$CH$_3$).

Synthesis of benzyl-2-amino-2-methylpropanoate hydrochloride salt

C$_{11}$H$_{16}$ClNO$_2$, MW 229.70.

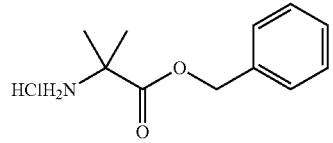

This was synthesised according to Standard Procedure 2, using 2-amino-isobutyric acid (1.960 g, 19.00 mmol) with p-toluene sulfonic acid monohydrate (3.750 g, 19.7 mmol) and benzylic alcohol (8.360 g, 77.30 mmol, 8 mL), in toluene (20 mL). The product was isolated as a white solid (2.556 g, yield 87.4%)

p-toluenesulfonate salt: $^1$H-NMR (CDCl$_3$, 300 MHz): δ 8.40 (3H, bs, NH$_3$Cl), 7.79 (2H, d, $^3$J=8.0 Hz, 'm' p-TSA), 7.34 (5H, m, CH$_2$Ph), 7.14 (2H, d, $^3$J=8.0 Hz, 'o' p-TSA), 5.16 (2H, s, CH$_2$Ph), 2.38 (3H, s, CH$_3$ p-TSA), 1.57 (6H, s, [CH$_3$]$_2$C)

$^{13}$C-NMR (CDCl$_3$; 75 MHz): δ 21.8 (CH$_3$, p-TSA), 23.9 ([CH$_3$]$_2$C), 57.8 (C[CH$_3$]$_2$), 68.3 (CH$_2$Ph), 126.55, 128.5, 128.8, 129.0, 129.3 (CH$_2$Ph+p-TSA), 135.4 ('ipso', CH$_2$Ph), 140.8 ('p', p-TSA), 141.9 ('ipso', p-TSA), 171.9 (COOCH$_2$Ph).

Hydrochloride salt: $^1$H-NMR (CDCl$_3$; 300 MHz): δ 9.10 (3H, bs, NH$_3$Cl), 7.41-7.31 (5H, m, CH$_2$Ph), 5.27 (2H, s, CH$_2$Ph), 1.77 ([CH$_3$]$_2$C).
$^{13}$C-NMR (CDCl$_3$; 75 MHz): δ 24.2 ([CH$_3$]$_2$C), 58.0 (C[CH$_3$]$_2$), 68.5 (CH$_2$Ph), 128.62, 129.0, 129.1 ('o', 'm', 'p', CH$_2$Ph), 135.2 ('ipso', CH$_2$Ph), 171.8 (COOCH$_2$Ph).

Synthesis of (E)-5-(2-bromovinyl)-2'-deoxyuridine (E)-5-(2-Carbomethoxyvinyl)-2'-deoxyuridine

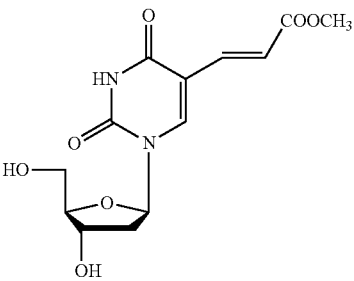

A mixture of Pd(OAc)$_2$ (0.316 g, 1.41 mmol), PPh$_3$ (0.741 g, 2.82 mmol), and triethylamine (4.9 mL) in 1,4-dioxane (50 mL) was stirred at 70° C. until an intense red colour had developed. To this 5-iodo-2'-deoxyuridine (10 g, 28.24 mmol) and methylacrilate (4.862 g, 56.48 mmol, 5.1 mL) in 1,4-dioxane (20 mL) were added and the mixture stiffed at refluxed for 30 mins. The reaction was filtered while still hot and the 20 filtrate cooled over night at 4° C. The resulting pale yellow precipitate was filtered, washed with DCM and dried in vacuo to give the product as white solid (6.2 g, yield 70.7%).

$^1$H-NMR (DMSO-d$_6$; 300 MHz) δ 11.64 (1H, bs, NH-3), 8.42 (1H, s, H-6), 7.37 (1H, d, $^3$J=15.8 Hz, H vinylic), 6.86

(1H, d, $^3J$=15.8 Hz, H vinylic), 6.13 (1H, t, $^3J$=6.5 Hz, H-1'), 5.27-5.20 (2H, 2bs, OH-3', OH-5'), 4.27 (1H, m, H-3'), 3.81 (1H, m, H-4'), 3.68 (3H,s C$\underline{H}_3$), 3.60 (2H, m, H-5'), 2.18 (2H, m, H-2').

$^{13}$C-NMR (DMSO-d$_6$; 75 MHz): δ 40.4 (C-2'), 51.6 (CH$_3$), 66.7 (C-5'), 70.0 (C-3'), 85.2 (C-4'), 88.0 (C-1'), 108.5 (C-5), 116.5 (C-5b), 138.5 (C-5a), 144.4 (C-6), 149.6, 162.1 (C-2, C-4),167.6 (COO).

(E-5-(2-Carboxyvinyl)-2'-deoxyuridine

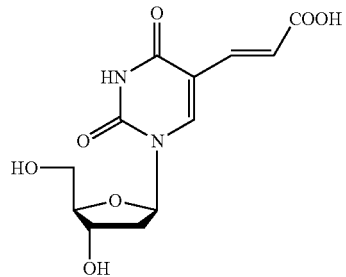

(E)-5-(2-carbomethoxyvinyl)-2'-deoxyuridine (6.0 g, 19.33 mmol) was dissolved in 300 mL of 1 M NaOH and the mixture stirred at room temperature for 3 hrs, filtered and the filtrate adjusted to pH 2 with 1M HCl. On cooling at 4° C. a white precipitate formed. This was filtered off and washed with cold water (2×20 ml) and acetone (2×20 mL) and dred to give a white solid (4.441 g, yield 77.1%).

$^1$H-NMR (DMSO-d$_6$; 300 MHz): δ 12.18 (1H, bs, CO$_2$H), 11.64 (1H, s, NH-3), 8.40 (1H, s, H-6), 7.30 (1H, d, $^3J=\overline{15.6}$ Hz, H vinylic), $\overline{6.78}$ (1H, d, $^3J$=15.8 Hz, H vinylic), 6.14 (1H, t, $^3J$=6.4 Hz, H-1'), 5.38-5.08 (2H, bs, OH-3', OH-5'), 4.26 (1H, m, H-3'), 3.80 (1H, m H-4'), 3.64 (2H, m, H-5'), 2.18 (2H, m, H-2').

$^{13}$C-NMR (DMSO-d$_6$; 75 MHz): δ 40.1 (C-2'), 61.2 (C-5'), 70.1 (C-3'), 85.1 (C-4'), 88.0 (C-1'), 108.7 (C-5), 118.0 (C-5b), 137.9 (C-5a), 143.9 (C-6), 149.6, 162.1 (C-2, C-4), 168.4 (COOH).

(E)-5-(2-bromovinyl)-2'-deoxyuridine

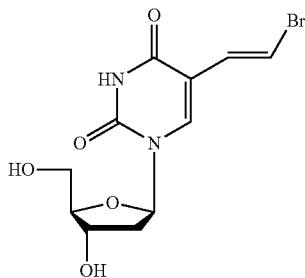

To a solution of (E)-5-(2-carboxyvinyl)-2'-deoxyuridine (5.777 g, 19.37 mmol) in dimethylforamide (29 mL) was added K$_2$CO$_3$ (5.890 g, 42.61 mmol) and the suspension stirred at room temperature for 15 mins. A solution of N-bromosuccinimide (3.655 g, 20.53 mmol) was added dropwise over 30 mins at 20° C. The resulting suspension was filtered and the solid washed with DMF. The combined filtrate and washings were evaporated to dryness in vacuo and the residue dissolved in MeOH. To this silica gel was added and the suspension evaporated to dryness and the solid applied to the top of chromatographic column. The column was eluted with chloroform/methanol 92/8 to give a white solid (5787 g, 71.9%). Crystallisation from water gave a white powder.

$^1$H-NMR (DMSO-d$_6$; 300 MHz) δ 11.59 (1H, bs, NH-3), 8.08 (1H, s, H-6), 7.25 (1H, d, $^3J$=13.6 Hz, H-5b), 6.85 (1H, d, $^3J$=13.6 Hz, H-5a), 6.13 (1H, t, $^3J$=6.5 Hz, H-1'), 5.29 (1H, bs, OH-3'), 5.13 (1H, bs, OH-5'), 4.24 (1H, m, H-3'), 3.79 (1H, m, H-4'), 3.66 (2H, m, H-5'), 2.51 (1H, m, H-2'), 2.14 (1H, m, H-2').

$^{13}$C-NMR (DMSO-d$_6$; 75 MHz): δ 40.2 (C-2'), 61.3 (C-5), 70.3 (C-4'), 84.8 (C-3'), 87.8 (C-1'), 108.9 (C-5b), 110.0 (C-5), 130.3 (C-5a), 149.6, 162.1 (C-2, C4).

Synthesis of (E)-5-(2-Bromovinyl)-2'-deoxyuridine-5'-[phenyl-(methoxy-L-alaninyl)]-phosphate (CPF 1)

C$_{21}$H$_{25}$BrN$_3$O$_9$P, MW 574.32.

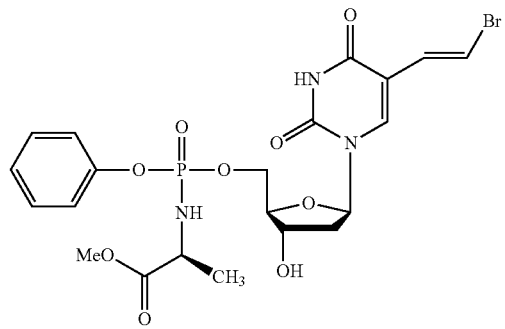

This was synthesised according to Standard procedure 5, using BVdU (300 mg, 0.90 mmol), Phenyl-(methoxy-L-alaninyl)-phosphorochloridate (472 mg, 1.7 mmol), NMI (4.5 mmol, 378 µL) in THF (9 mL) for 2 hrs. The crude product was purified by column chromatography, eluting with CH$_2$Cl$_2$/Methanol 97:3 to give the pure product as a white foamy solid (356 mg, yield 69%).

$^{31}$P-NMR (CDCl$_3$, 121 MHz): δ 4.72, 4.40.

$^1$H-NMR (CDCl$_3$; 300 MHz): δ 9.9 (1H, bs, H-3), 7.64 (1H, 2×s, H-6), 7.44-7.39 (1H, 2d, $^3J$=14 Hz, H-5b), 7.37-7.15 (5H, m, OPh), 6.75-6.67 (1H, 2d, $^3J$=14 Hz, H-5a), 6.30-6.21 (1H, 2t, $^3J$=6 Hz, H1'), 4.57-4.29 (3H, m, H-5'+H-3'), 4.2-3.96 (3H, H-4', NH, CHala), 3.72 (3H, s, CH$_3$O), 2.49-2.40 (1H, m, one of H-2'), 2.12-2.01 (1H, m, one of H-2'), 1.38 (3H, d, $^3J$=7 Hz, CH$_{3\ ala}$).

$^{13}$C-NMR (DMSO; 75 MHz): δ 22.4 (CH$_{3\ ala}$), 41.9, 41.8 (C-2'), 51.9 (C$\underline{H}$[CH$_3$]), 54.3 (CH$_3$O), 67.5 (C-5'), 72.3, 71.9 (C-3'), 87.3, $\overline{87.2}$, 86.9, 86.8 ($\overline{C}$-1', C-4'), 110.6 (C-5b), 113.1 (C-5), 121.7 ('o', OPh), 127.0 ('p', OPh), 130.1 (C-5a), 131.5 ('m', OPh), 139.2 $\overline{(C}$-6),150.9 ('ipso', OP$\underline{h}$) 151.9 (C-4), 163.2(C-2), 175.7 (C$\underline{\ }$OOCH$_3$).

Synthesis of (E)-5-(2-Bromovinyl)-2'-deoxyuridine-5'-[phenyl-(ethoxy-L-alaninyl)]-phosphate(CPF 3)

$C_{22}H_{27}BrN_3O_9P$, MW=588.34.

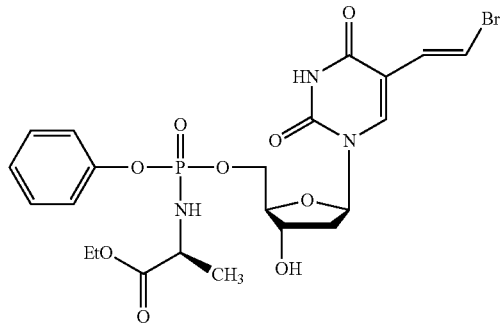

This was synthesised according to Standard procedure 5, using BVdU (150 mg, 0.45 mmol), Phenyl-(ethoxy-L-alaninyl)-phosphorochloridate (249 mg, 0.9 mmol), NMI (2.8 mmol, 190 µL) in THF (4 mL) for 2 hrs. The crude product was purified by column chromatography, eluting with CH$_2$Cl$_2$/Methanol 97:3 to give the pure product as a white foamy solid (145 mg, yield 55%).

$^{31}$P-NMR (CDCl$_3$, 121 MHz): δ 4.48, 4.86.

$^{1}$H-NMR (CDCl$_3$, 300 MHz): δ 7.65 (1H, 2xs, H-6), 7.44-7.39 (1H, 2d, $^3$J=13 Hz, H-5b), 7.35-7.10 (5H, m, OPh), 6.78-6.65 (1H, 2d, $^3$J=13 Hz, H-5a), 6.35-6.25 (1H, 2t, $^3$J=6 Hz, H1'), 4.62-3.95 (8H, m, H-5', H-3', H-4', CHala, NH, CH$_3$CH$_2$O), 2.49-2.40 (1H, m, one of H-2'), 2.10-2.00 (1H, m, one of H-2'), 1.40 (3H, d, $^3$J=7 Hz, CH$_{3\ ala}$), 1.25 (3H, 2t, $^3$J=7 Hz, CH$_4$CH$_2$O).

$^{13}$C-NMR (CDCl$_3$, 75 MHz): δ 14.5 (CH$_3$CH$_2$O) 21.2, 21.1 (CH$_3$ala), 40.9, 40.7 (C-2'), 50.8, 50.7 (CHala), 62.2, 62.1 (CH$_3$CH$_2$O), 66.5, 66.3 (C-5'), 70.9, 70.6 (C-3'), 86.0, 85.6 (C-1', C-4'), 110.1 (C-5b), 111.8 (C-5), 120.6 ('o', OPh), 125.0 ('p', OPh), 129.0 (C-5a), 130.2 ('m', OPh), 138.2 (C-6), 149.9 (C-4), 150.7 ('ipso', OPh), 162.3 (C-2), 174.2, 174.1 (COOCH$_2$CH$_3$).

Synthesis of (E)-5-(2-Bromovinyl)-2'-deoxyuridine-5'-[phenyl-(benzoxy-L-alaninyl)]-phosphate (CPF 2)

$C_{27}H_{29}BrN_3O_9P$, MW=649.08.

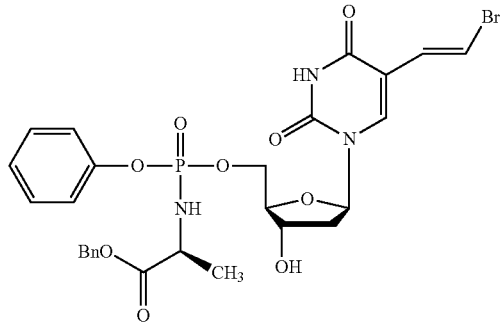

This was synthesised according to Standard procedure 5, using BVdU (150 mg, 0.45 mmol), Phenyl-(benzyloxy-L-alaninyl)-phosphorochloridate (249 mg, 0.9 mmol), NMI (2.8 mmol, 190 µL) in THF (5 mL) for 2 hrs. The crude product was purified by column chromatography, eluting with CH$_2$Cl$_2$/Methanol 97:3 to give the pure product as a white foamy solid (228 mg, yield 78%).

$^{31}$P-NMR (CDCl$_3$, 121 MHz): δ 4.74, 4.44.

$^{1}$H-NMR (CDCl$_3$, 300 MHz): δ 10.31 (1H, bs, H-3), 7.63 (1H, 2xs, H-6), 7.45-7.14 (11H, m, OPh+CH$_2$Ph, H-5b), 6.75-6.66 (1H, 2d, $^3$J=14 Hz, H-5a), 6.30-6.25 (1H, m, H-1'), 5.18-50.9 (1H, s, CH$_2$Ph), 4.70-4.04 (6H, m, H-3', H-5', H-4', NH, CHala), 2.42 (1H, m, one of H-2'), 2.02 (1H, m, one of H-2'), 1.40 (3H, d, $^3$J=7 Hz, CH$_3$ala).

$^{13}$C-NMR (CDCl$_3$, 75 MHz): δ 20.7, 20.8 (CH$_3$ala), 40.4 (C-2'), 50.4 (CHala), 66.0 (C-5') 67.4 (CH$_2$Ph), 70.6 (C-3'), 85.4, 85.5, 85.6, 85.8 (C-1', C-4'), 109.9 (C-5b), 111.5 (C-5b), 120.2 ('o', OPh), 125.4 ('p', OPh), 128.5, 128.6, 129.9 ('m' OPh, Bn, C-5a), 135.1('ipso', CH$_2$Ph) 137.8 (C-6), 149.8 (C-4) 150.2 ('ipso', OPh), 161.8 (C-2), 173.6 (COOBn).

Synthesis of (E)-5-(2-Bromovinyl)-2'-deoxyuridine-5'-[para-fluorophenyl-(methoxy-L-alaninyl)]-phosphate (CPF 5)

$C_{21}H_{24}BrFN_3O_9P$, MW=592.31.

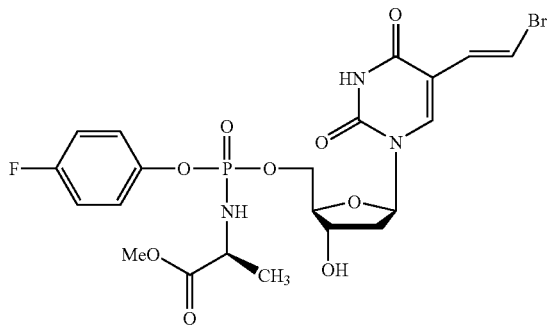

This was synthesised according to Standard procedure 5, using BVdU (200 mg, 0.60 mmol), para-fluorophenyl-(methoxy-L-alaninyl)-phosphorochloridate (442 mg, 1.5 mmol), NMI (4.98 mmol, 332 µL) in THF (5 mL) for 2 hrs. The crude product was purified by column chromatography, eluting with CH$_2$Cl$_2$/Methanol 97:3 to give the pure product as a white foamy solid (177 mg, yield 50%).

$^{31}$P-NMR (CDCl$_3$, 121 MHz): δ 5.10, 4.81.

$^{1}$H-NMR (CDCl$_3$; 300 MHz): δ 10.1 (1H, bs, H-3), 7.60 (1H, 2xs, H-6), 7.39-7.32 (1H, 2d, $^3$J=14 Hz, H-5b), 7.20-6.95 (4H, m, OPh), 6.70-6.60 (1H, 2d, $^3$J=14 Hz, H-5a), 6.30-6.15 (1H, 2t, $^3$J=6 Hz, H1'), 4.55-4.29 (3H, m, H-5'+H-3'), 4.15 (1H, NH), 4.05-3.85 (2H, H-4', CHala), 3.72 (3H, 2s, CH$_3$O), 2.49-2.32 (1H, m, one of H-2'), 2.15-2.05 (1H, m, one of H-2'), 1.35 (3H, 2d, $^3$J=6 Hz, CH$_{3\ ala}$).

$^{13}$C-NMR (DMSO; 75 MHz): δ 21.2 (CH$_{3\ ala}$), 40.8 (C-2'), 50.8, 50.6 (CH[CH$_3$]), 53.2 (CH$_3$O), 66.7, 66.3 (C-5'), 71.9, 71.8 (C-3'), 86.1, 85.7, 85.8 (C-1', C-4'), 110.3 (C-5b), 111.9 (C-5), 117.0, 116.7 ('o', OPh), 122.0 ('m', OPh), 128.2 (C-5a), 138.2 (C-6), 149.0 ('ipso', OPh) 149.9 (C-4), 158.5 ('p', OPh), 163.2(C-2), 175.1 (COOCH$_3$).

Synthesis of (E)-5-(2-Bromovinyl)-2'-deoxyuridine-5'-[para-fluorophenyl-(ethoxy-L-alaninyl)]-phosphate (CPF 6)

$C_{22}H_{26}BrFN_3O_9P$, MW=606.33.

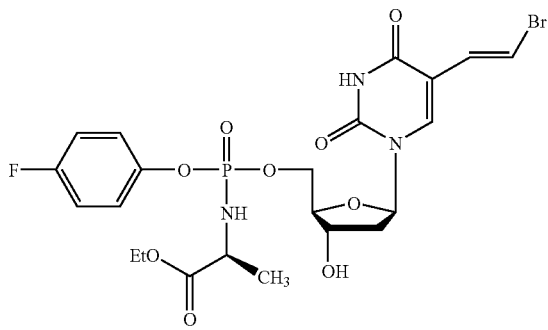

This was synthesised according to Standard procedure 5, using BVdU (200 mg, 0.60 mmol), para-fluorophenyl-(ethoxy-L-alaninyl)-phosphorochloridate (464 mg, 1.5 mmol), NMI (4.98 mmol, 332 μL) in THF (5 mL) for 2 hrs. The crude product was purified by column chromatography, eluting with $CH_2Cl_2$/Methanol 97:3 to give the pure product as a white foamy solid (240 mg, yield 66%).

$^{31}$P-NMR (CDCl$_3$, 121 MHz): δ 5.14, 4.88.

$^1$H-NMR (CDCl$_3$, 300 MHz): δ 10.25 (1H, bs, H-3), 7.85 (1H, 2×s, H-6), 7.44-7.39 (1H, 2d, $^3$J=14 Hz, H-5b), 7.3-7.0 (4H, m, OPh), 6.8-6.65 (1H, 2d, $^3$J=14 Hz, H-5a), 6.35-6.25 (1H, 2t, $^3$J=6 Hz, H1'), 4.6-4.1 (6H, m, H-5', H-3', CHala, NH, CH$_3$CH$_2$O), 4.02 (1H, m, H-4'), 2.55-2.45 (1H, m, one of H-2'), 2.20-2.10 (1H, m, one of H-2'), 1.40 (3H, d, $^3$J=8 Hz, CH$_{3\ ala}$), 1.25 (3H, 2t, $^3$J=7 Hz, CH$_3$CH$_2$O).

$^{13}$C-NMR (CDCl$_3$, 75 MHz): δ 14.5 (CH$_3$CH$_2$O) 21.3 (CH$_3$ala), 40.8, 40.7 (C-2'), 50.8, 50.7 (CHala), 62.3 (CH$_3$CH$_2$O), 66.7, 66.3 (C-5'), 71.1, 70.7 (C-3'), 86.1, 85.8, 85.6, 85.4 (C-1', C-4'), 110.4 (C-5b), 111.9 (C-5), 117.0 ('o', OPh), 122.2 ('m', OPh), 128.9 (C-5a), 138.2 (C-6), 146.4 ('ipso', OPh), 149.9 (C-4), 158.5 ('p', OPh), 162.2, 161.8 (C-2), 174.2 (COOCH$_2$CH$_3$).

Synthesis of (E-5-(2-Bromovinyl)-2'-deoxyuridine-5'-[para-fluorophenyl-(benzoxy-L-alaninyl)]-phosphate (CPF 7)

$C_{27}H_{28}BrFN_3O_9P$, MW=668.40.

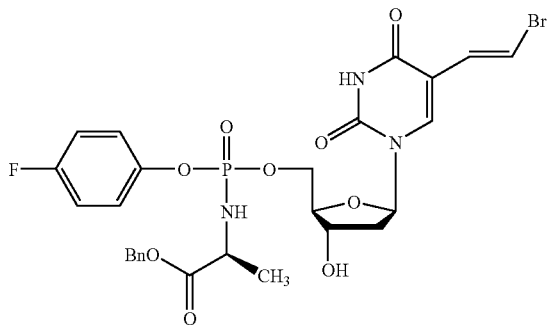

This was synthesised according to Standard procedure 5, using BVdU (200 mg, 0.60 mmol), para-fluorophenyl-(ben-zyloxy-L-alaninyl)-phosphorochloridate (556 mg, 1.5 mmol), NMI (4.98 mmol, 332 μL) in THF (5 mL) for 2 hrs. The crude product was purified by column chromatography, eluting with $CH_2Cl_2$/Methanol 97:3 to give the pure product as a white foamy solid (256 mg, yield 64%).

$^{31}$P-NMR (CDCl$_3$, 121 MHz): δ 4.74, 4.44.

$^1$H-NMR (CDCl$_3$, 300 MHz): δ 7.69 (1H, 2×s, H-6), 7.45-7.39 (1H, 2d, $^3$J=14 Hz, H-5b), 7.37-7.00 (9H. m, OPh+CH$_2$Ph), 6.75-6.65 (1H, 2d, $^3$J=14 Hz, H-5a), 6.30-6.2 (1H, 2t, $^3$J=6 Hz, H-1'), 5.2 (1H, 2s, CH$_2$Ph), 4.85-4.00 (6H, m, H-3', H-5',H-4', NH, CHala), 2.47 (1H, m, one of H-2'), 2.0-2.15 (1H, m, one of H-2'), 1.38 (3H, d, $^3$J=7 Hz, CH$_3$ala).

$^{13}$C-NMR (CDCl$_3$, 75 MHz): δ 21.2, 21.1 (CH$_3$ala), 40.7 (C-2'), 50.4 (CHala), 66.7, 66.4 (C-5'), 67.8 (CH$_2$Ph), 71.1, 70.7 (C-3'), 86.0, 85.7, 85.4, 85.3 (C-1', C-4'), 110.4 (C-5b), 111.9 (C-5), 117.0 ('o', OPh), 122.0 ('m', OPh), 128.7, 128.6 (Bn, C-5a), 135.4('ipso', CH$_2$Ph) 138.2 (C-6), 146.5 ('ipso', OPh), 149.9 (C-4), 158.5 ('p' OPh), 162.2 (C-2), 173.9 (COOBn).

Synthesis of (E)-5-(2-Bromovinyl)-2'-deoxyuridine-5'-[para-nitrophenyl-(methoxy-L-alaninyl)]-phosphate (CPF 10)

$C_{21}H_{24}BrN_4O_{11}P$, MW=619.31.

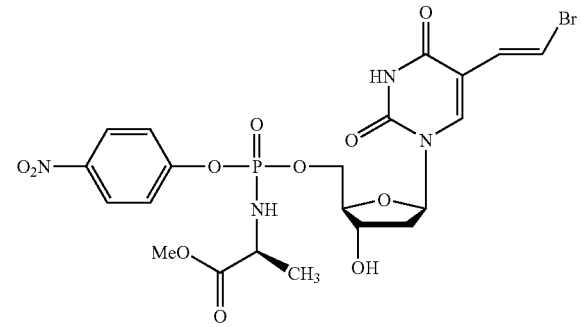

This was synthesised according to Standard procedure 5, using BVdU (200 mg, 0.60 mmol), para-nitrophenyl-(methoxy-L-alaninyl)-phosphorochloridate (483 mg, 1.5 mmol), NMI (4.98 mmol, 332 μL) in THF (5 mL) for 2 hrs. The crude product was purified by column chromatography, eluting with $CH_2Cl_2$/Methanol 97:3 to give the pure product as a white foamy solid (211 mg, yield 57%).

$^{31}$P-NMR (CDCl$_3$, 121 MHz): δ 4.95.

$^1$H-NMR (MeOD; 300 MHz): δ 8.3-8.2 (2H, m, OPh) 7.8-7.75 (1H, 2×s, H-6), 7.35-7.30, 7.55-7.4 (2H, m, OPh), 7.35-7.30 (1H, 2d, $^3$J=14 Hz, H-5b), 6.80-6.70 (1H, 2d, $^3$J=14 Hz, H-5a), 6.30-6.2 (1H, 2t, $^3$J=6 Hz, H1'), 4.5-4.3 (3H, m, H-5',H-3'), 4.2-4.0 (2H, m, H-4', CHala), 3.72 (3H, 2s, CH$_3$O), 2.35-2.15 (2H, n, 2 H-2'), 1.35 (3H, 2d, $^3$J=7 Hz, CH$_{3\ ala}$).

$^{13}$C-NMR (DMSO; 75 MHz): δ 20.9 (CH$_{3\ ala}$), 41.6, 41.5 (C-2'), 52.0, 51.9 (CH[CH$_3$]), 53.4 (CH$_3$O), 68.5 (C-5'), 72.4, 72.3 (C-3'), 87.7, 87.4, 87.0, 86.9 (C-1', C-4'), 109.8 (C-5b), 112.8 (C-5), 122.6 ('o', OPh), 127.1 ('m', OPh), 130.8 (C-5a), 140.3 (C-6), 146.5 ('ipso', OPh), 151.4 (C-4), 157.2 ('p', OPh), 163.9 (C-2), 175.8, 175.5 (COOCH$_3$).

Synthesis of (E)-5-(2-Bromovinyl)-2'-deoxyuridine-5'-[para-nitrophenyl-(ethoxy-L-alaninyl)]-phosphate (CPF 9)

$C_{22}H_{26}BrN_4O_{11}P$, MW=633.34.

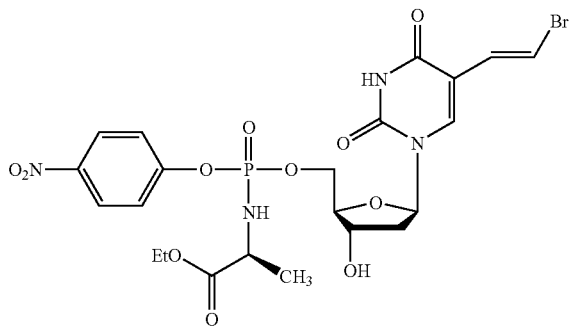

This was synthesised according to Standard procedure 5, using BVdU (200 mg, 0.60 mmol), para-nitrophenyl-(ethoxy-L-alaninyl)-phosphorochloridate (504 mg, 1.5 mmol), NMI (4.98 mmol, 332 μL) in THF (5 mL) for 1 hr. The crude product was purified by column chromatography, eluting with $CH_2Cl_2$/Methanol 97:3 to give the pure product as a white foamy solid (232 mg, yield: 61%).

$^{31}$P-NMR (CDCl$_3$, 121 MHz): δ 4.28.
$^1$H-NMR (CDCl$_3$, 300 MHz): δ 10.25 (1H, bs, H-3), 8.25-8.2 (2H, 2d, $^3$J=9 Hz OPh), 7.7 (1H, 2×s, H-6), 7.5-7.45 (2H, 2d, $^3$J=9 Hz, OPh), 7.4-7.35 (1H, 2d, $^3$J=14 Hz, H-5b), 6.7-6.65 (1H, 2d, $^3$J=14 Hz, H-5a), 6.3-6.2 (1H, 2t, $^3$J=6 Hz, H1'), 4.8-4.1 (7H, m, H-5', H-4' H-3', CHala, NH, CH$_3$CH$_2$O), 2.45-2.4 (1H, m, one of H-2'), 2.20-2.10 (1H, m, one of H-2'), 1.40 (3H, d, $^3$J=8 Hz, CH$_3$ $_{ala}$), 1.3 (3H, 2t, $^3$J=7 Hz, C H$_3$CH$_2$O).
$^{13}$C-NMR (CDCl$_3$, 75 MHz): δ 14.5 (CH$_3$CH$_2$O) 21.1 (CH$_3$ala), 40.6 (C-2'), 50.8, 50.7 (CHala), 62.5 (CH$_3$CH$_2$O), 66.9, 66.8 (C-5'), 71.2, 70.9 (C-3'), 86.3, 85.9, 85.4, 85.3 (C-1', C-4'), 111.8 (C-5), 121.3 ('o', OPh), 126.1 ('m', OPh), 128.8 (C-5a), 138.4 (C-6), 145.1 ('ipso', OPh), 149.9 (C-4), 155.5 ('p', OPh), 162.3 (C-2), 174.0, 173.9 (COOCH$_2$CH$_3$).

Synthesis of (E)-5-(2-Bromovinyl)-2'-deoxyuridine-5'-[para-nitrophenyl-(benzoxy-L-alaninyl)]-phosphate (CPF 8)

$C_{27}H_{28}BrN_4O_{11}P$, MW=695.41.

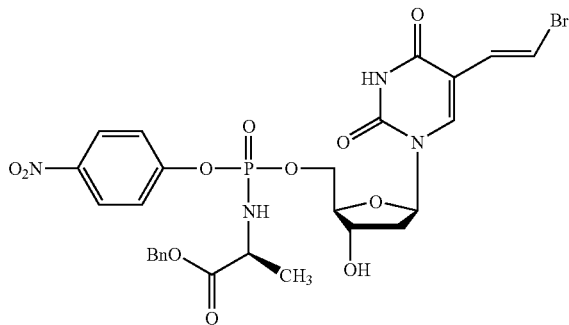

This was synthesised according to Standard procedure 5, using BVdU (200 mg, 0.60 mmol), para-nitrophenyl-(benzyloxy-L-alaninyl)-phosphorochloridate (597 mg, 1.5 mmol), NMI (4.98 mmol, 332 μL) in THF (5 mL) for 2 hrs. The crude product was purified by column chromatography, eluting with $CH_2Cl_2$/Methanol 97:3 to give the pure product as a white foamy solid (228 mg, yield 55%).

$^{31}$P-NMR (CDCl$_3$, 121 MHz): δ 4.74, 4.44.
$^1$H-NMR (CDCl$_3$, 300 MHz): δ 10.4-10.3 (1H, bs, H-3), 8.2-8.1 (2H, m, OPh), 7.69 (1H, 2×s, H-6), 7.4-7.2 (1H, 2d, $^3$J=14 Hz, H-5b), 7.37-7.00 (7H. m, OPh+CH$_2$Ph), 6.75-6.65 (1H, 2d, $^3$J=14 Hz, H-5a), 6.25-6.15 (1H, 2t, $^3$J=6 Hz, H-1'), 5.2 (1H, d, CH$_2$Ph), 4.87 (1H, m, H-3'), 4.6-4.2 (3H, m, H-5', CHala) 4.2-4.00 (2H, m, H-4', NH,), 2.55-2.45 (1H, m, one of H-2'), 2.2-2.05 (1H, m, one of H-2'), 1.38 (3H, d, $^3$J=7 Hz, CH$_3$ala).
$^{13}$C-NMR (CDCl$_3$, 75 MHz): δ 21.2, 21.1 (CH$_3$ala), 40.6 (C-2'), 50.9 (CHala), 67.1, 670 (C-5'), 68.0 (CH$_2$Ph), 71.3, 70.9 (C-3'), 86.3, 86.0, 85.3, 85.2 (C-1', C-4'), 110.4 (C-5b), 111.9, 111.8 (C-5), 121.3 ('o', OPh), 126.2-126.1 ('m', OPh), 129.1, 128.7, 128.6 (Bn, C-5a), 135.4 ('ipso', CH$_2$Ph), 138.3 (C-6), 145.1 ('ipso', OPh), 149.9 (C4), 155.6 ('p' OPh), 162.2 (C-2), 173.8, 173.7 (COOBn).

Synthesis of (E)-5-(2-bromovinyl)-2'-deoxyuridine-5'-[para-(trifluoromethyl)-phenyl-(methoxy-L-alaninyl)]-phosphate (CPF 15)

$C_{22}H_{24}BrF_3N_3O_9$, MW=642.31.

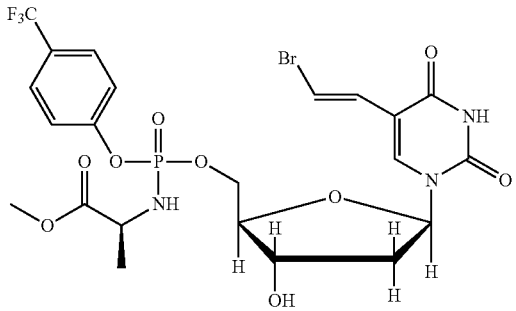

This was synthesised according to Standard procedure 5, using BVdU (200 mg, 0.60 mmol), phenyl-(methoxy-L-alaninyl)-phosphorochloridate (518.8 mg, 1.5 mmol), NMI (246.3 mg, 3.0 mmol, 239 μL) in THF (5 mL) for 4 hrs. The crude product was purified by column chromatography, eluting with chloroform/methanol 97:3 to give the pure product as a white foamy solid (211.1 mg, yield 54.7%).

$^{31}$P-NMR (MeOD, 121 MHz): δ 5.23, 5.07.
$^1$H-NMR (MeOD, 300 MHz): δ 7.80 (1H, s, H-6), 7.70 (2H, d, $^3$J=8.7 Hz, OPh), 7.47-7.42 (2H, m, OPh), 7.37 (1H, d, $^3$J=13.6 Hz, H-5b), 6.82-6.78 (1H, d, 3J=13.6 Hz, H-5a), 6.30-6.23 (1H, m, H-1'), 4.52-4.29 (3H, m, H-3'+H-5'), 4.17-4.13 (1H, m, H-4'), 4.05-3.91 (1H, m, CHCH$_3$), 3.67 (3H, s, OCH$_3$), 2.35-2.32 (1H, m, one of H-2'), 2.23-2.16 (1H, m, one of H-2'), 1.37-1.34 (3H, d, $^3$J=7.1 Hz, CHCH$_3$.
$^{13}$C-NMR (MeOD, 75 MHz): δ 20.6, 20.7, 20.8, 20.9 (CH CH$_3$), 41.5, 41.7 (C-2'), 51.9, 52.0 (CHCH$_3$), 68.2, 68.3 (C-5'), 72.4, 72.5 (C-3'), 87.1, 87.2, 87.4, 87.6 (C-1', C-4'), 109.7 (C-5b), 112.6 (C-5), 122.5, 122.7 ('o', OPh), 125.8 (CF$_3$, J=269 Hz), 128.7 ('m', OPh), 128.8 ('p', J=33 Hz, OPh), 130.9 (C-5a), 140.3 (C-6), 151.4, 151.5 ('ipso', OPh), 155.1, 155.2 (C-4), 164.0 (C-2), 175.6, 175.9, (COOCH$_3$).

Synthesis of (E)-5-(2-bromovinyl)-2'-deoxyuridine-5'-[para-(trifluoromethyl)-phenyl-ethoxy-L-alaninyl)]-phosphate (CPF 25)

$C_{23}H_{26}BrF_3N_3O_9P$, MW=656.34.

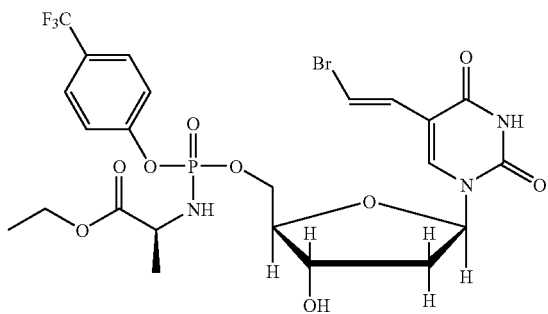

This was synthesised according to Standard procedure 5, using BVdU (200 mg, 0.60 mmol), phenyl-(ethoxy-L-alaninyl)-phosphorochloridate (539.5 mg, 1.5 mmol), NMI (246.3 mg, 3.0 mmol, 239 µL) in THF (5 mL) for 20 hrs. The crude product was purified by column chromatography, eluting with dichloromethane/methanol 95:5 to give the pure product as a white foamy solid (172.6 mg, yield 43.8%).

$^{31}$P-NMR (CDCl$_3$, 121 MHz): δ 4.65, 4.35.

$^1$H-NMR (CDCl$_3$, 300 MHz): δ 10.05 (1H, s, H-3), 7.69-7.64 (3H, m, H-6+OPh), 7.46-7.39 (3H, m, OPh+H-5b), 6.76-6.68 (1H, 2d, $^3$J=13.6 Hz, H-5a), 6.34-6.25 (1H, m, H-1'), 4.57-4.35 (4H, m, H-3'+H-5'+NH, 4.27-4.13 (4H, m, H-4'+OCH$_2$CH$_3$+OH-3'), 4.12-3.98 (1H, m, CHCH$_3$), 2.53-2.47 (1H, m, one of H-2'), 2.21-2.12 (1H, m, one of H-2'), 1.43-1.40 (3H, d, $^3$J=7.0 Hz, CHCH$_3$), 1.28, 1.27 (3H, 2t, $^3$J=7.0 Hz, OCH$_2$CH$_3$)

$^{13}$C-NMR (CDCl$_3$, 75 MHz): δ 14.5 (CH$_3$CH$_2$O), 21.2, 21.3 (CHCH$_3$), 40.7 (C-2'), 50.8, 50.9 (CHCH$_3$), 62.4 (CH$_3$CH$_2$O), 66.3, 66.7 (C-5'), 70.7, 71.1 (C-3'), 85.3, 85.4, 85.8, 86.1 (C-1', C-4'), 110.5 (C-5b), 112.0 (C-5), 122.0 ('o', OPh), 124.2 (CF$_3$, J=271 Hz), 127.7, 127.8, 128.7 ('m', 'p', OPh), 128.8 (C-5a), 138.0 (C-6), 149.7 ('ipso', OPh), 153.2 (C-4), 161.9 (C-2), 174.0, 174.1 (COOCH$_2$CH$_3$).

Synthesis of (E)-5-(2-Bromovinyl)-2'-deoxyuridine-5'-[para-trifluorophenyl-(benzoxy-L-alaninyl)]-phosphate (CPF 4)

$C_{28}H_{28}BrF_3N_3O_9P$, MW=718.41.

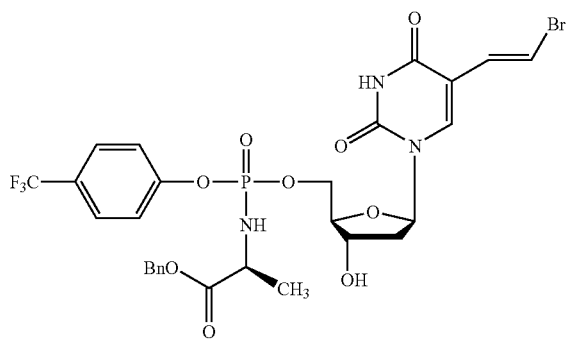

This was synthesised according to Standard procedure 5, using BVdU (200 mg, 0.60 mmol), para-trifluorophenyl-(benzyloxy-L-alaninyl)-phosphorochloridate (632 mg, 1.55 mmol), NMI (4.98 mmol, 332 µL) in THF (6 mL) for 2 hrs. The crude product was purified by column chromatography, eluting with CH$_2$Cl$_2$/Methanol 97:3 to give the pure product as a white foamy solid (308 mg, yield 71%).

$^{31}$P-NMR (CDCl$_3$, 121 MHz): δ 5.31, 4.87.

$^1$H-NMR (CDCl$_3$, 300 MHz): δ 10.05 (1H, bs, H-3), 7.7, 7.25 (11H. m, H-5b, H-6 OPh+CH$_2$Ph), 6.75-6.65 (1H, 2d, $^3$J=14 Hz, H-5a), 6.35-6.2 (1H, 2t, $^3$J=6 Hz, H-1'), 5.15 (1H, 2s, CH$_2$Ph), 4.6-4.25 (4H, m, H-5', H-3', CHala) 4.2-4.00 (2H, m, H-4', NH,), 2.55-2.4 (1H, m, one of H-2'), 2.2-2.05 (1H, m, one of H-2'), 1.38 (3H, d, $^3$J=7 Hz, CH$_3$ala).

$^{13}$C-NMR (CDCl$_3$, 75 MHz): δ 21.2, 21.1 (CH$_3$ala), 40.7 (C-2'), 50.9, 50.8 (CHala), 67.1, 67.0 (C-5'), 68.0 (CH$_2$Ph), 71.2, 70.9 (C-3'), 86.1, 85.8, 85.5, 85.4 (C-1', C-4'), 110.2 (C-5b), 111.9, 111.8 (C-5), 121.1 ('o', OPh), 125.1 (d, J=270 Hz, CF$_3$), 127.6 ('m', OPh), 129.1, 128.7, 128.6 (Bn, C-5a), 130.1 ('p',q, J=32 Hz, OPh) 135.4 ('ipso', CH$_2$Ph) 138.2 (C-6), 150.2, 150.1 (C4), 153.6 ('ipso' OPh), 162.7 (C-2), 173.9, 173.6 (COOBn).

Synthesis of (E)-5-(2-bromovinyl)-2'-deoxyuridine-5'-[4-chlorophenyl-(methoxy-L-alaninyl)]-phosphate (CPF 13)

$C_{21}H_{24}BrClN_3O_9P$, MW=608.76.

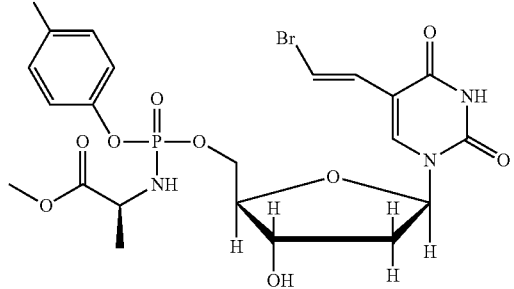

This was synthesised according to Standard procedure 5, using BVdU (200 mg, 0.60 mmol), 4-chlorophenyl-(methoxy-L-alaninyl)-phosphorochloridate (374.5 mg, 1.2 mmol), NMI (246.3 mg, 3.0 mmol, 239 µL) in THF (8 mL) for 5 hrs. The crude product was purified by column chromatography, eluting with Chloroform/Methanol 97:3 to give the pure product as a white foamy solid (139.0 mg, yield 38.0%).

$^{31}$P-NMR (CDCl$_3$, 121 MHz): δ 4.81, 4.54.

$^1$H-NMR (CDCl$_3$, 300 MHz): δ 10.11 (1H, bs, H-3), 7.68 (1H, s, H-6), 7.46-7.40 (1H, d, $^3$J=13.6 Hz, H-5b), 7.35-7.20 (4H, m, OPh), 6.76-6.67 (1H, 2d, $^3$J=13.6 Hz, H-5a), 6.34-6.24 (1H, m, H-1'), 4.58-4.40 (5H, m, H-3'+H-5'+NH), 4.36-4.19 (1H, m, H-4'), 4.07-3.99 (1H, m, CHCH$_3$), 3.75 (3H, s, OCH$_3$), 2.49-2.48 (1H, m, one of H-2'), 2.17-2.15 (1H, m, one of H-2'), 1.42-1.39 (3H, d, $^3$J=7.0 Hz, CHCH$_3$).

$^{13}$C-NMR (CDCl$_3$, 75 MHz): δ 21.2 (CHCH$_3$), 40.7, 40.8 (C-2'), 50.6, 50.8 (CHCH$_3$), 53.2, 53.3 (OCH$_3$), 66.4, 66.7 (C-5'), 70.8, 71.2 (C-3'), 85.4, 85.5, 85.8, 86.2 (C-1', C-4'), 110.5 (C-5b), 111.9, 112.0 (C-5), 122.0 ('o', OPh), 128.9 (C-5a), 130.3 ('m', OPh), 131.1 ('p', OPh), 138.2 (C-6), 149.1, 149.2 ('ipso', OPh), 149.8 (C-4), 162.1, 162.2 (C-2), 174.5, 174.6 (COOCH$_3$).

Synthesis of (E)-5-(2-bromovinyl)-2'-deoxyuridine-5'-[4-chlorophenyl-(ethoxy-L-alaninyl)]-phosphate (CPF 11)

$C_{22}H_{26}BrN_3O_9P$, Mw=622.79.

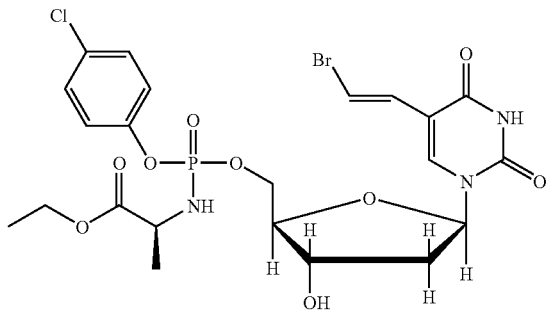

This was synthesised according to Standard procedure 5, using BVdU (300 mg, 0.90 mmol), 4-chlorophenyl-(ethoxy-L-alaninyl)-phosphorochloridate (557.7 mg, 1.71 mmol), NMI (221.7 mg, 2.7 mmol, 215 μL) in THF (10 mL) for 16 hrs. The crude product was purified by column chromatography, eluting with dichloromethane/methanol 97:3 to give the pure product as a white foamy solid (168.4 mg, yield 30.0%).

$^{31}$P-NMR (CDCl$_3$, 121 MHz): δ 4.88, 4.65.

$^1$H-NMR (CDCl$_3$, 300 MHz): δ 9.51 (1H, bs, H-3), 7.69-7.68 (1H, 2s, H-6), 7.49-7.43 (1H, 2d, $^3$J=13.6 Hz, H-5b), 7.37-7.22 (4H, m, OPh), 6.79-6.71 (1H, 2d, $^3$J=13.6 Hz, H-5a), 6.33-6.24 (1H, m, H-1'), 4.62-4.34 (3H, m, H-3'+H-5'), 4.28-3.89 (5H, m, H-4'+OCH$_2$CH$_3$+CHCH$_3$+NH), 2.59-2.45 (1H, m, one of H-2'), 2.22-2.14 (1H, m, one of H-2'), 1.43-1.41 (3H, d, $^3$J=7.0 Hz, CHCH$_3$), 1.33-1.28 (3H, 2t, $^3$J=7.2 Hz, OCH$_2$CH$_3$).

$^{13}$C-NMR (CDCl$_3$, 75 MHz): δ 14.5 (CH$_3$CH$_2$O), 21.2, 21.3 (CHCH$_3$), 40.7 (C-2'), 50.7, 50.8 (CHCH$_3$), 62.4 (CH$_3$CH$_2$O), 66.7 (C-5'), 70.8, 71.2 (C-3'), 85.4, 85.8, 86.1 (C-1', C-4'), 110.4 (C-5b), 112.0 (C-5), 122.0, 122.1 ('o', OPh), 128.9 (C-5a), 130.3 ('m', OPh), 131.1 ('p', OPh), 138.2 (C-6), 149.2 ('ipso', OPh), 150.0 (C-4), 162.2 (C-2), 174.1, 174.2 (COOCH$_2$CH$_3$).

Synthesis of (E)-5-(2-bromovinyl)-2'-deoxyuridine-5'-[4-chlorophenyl-(benzoxy-L-alaninyl)]-phosphate (CPF 12)

$C_{22}H_{26}BrN_3O_9P$, MW=622.79.

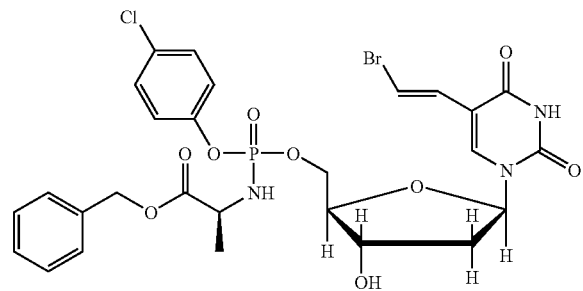

This was synthesised according to Standard procedure 5, using BVdU (300 mg, 0.90 mmol), 4-chlorophenyl-(benzoxy-L-alaninyl)-phosphorochloridate (698.7 mg, 1.80 mmol), NMI (369.5 mg, 4.5 mmol, 358.7 μL) in THF (10 mL) for 2 hrs. The crude product was purified by column chromatography, eluting with dichloromethane/methanol 95:5 to give the pure product as a white foamy solid (310.0 mg, yield 50.3%).

$^{31}$P-NMR (CDCl$_3$, 121 MHz): δ 4.81, 4.53.

$^1$H-NMR (CDCl$_3$, 300 MHz): δ 10.10 (1H, bs, H-3), 7.65-7.63 (1H, 2s, H-6), 7.69-7.68 (1H, 2s, H-6), 7.46, 7.41 (1H, 2d, $^3$J=13.6 Hz, H-5b), 7.40-7.17 (9H, m, OPh), 6.75-6.66 (1H, 2d, $^3$J=13.6 Hz, H-5a), 6.33-6.23 (1H, 2t, $^3$J=6.0 Hz, H-1'), 5.17 (2H, s, CH$_2$Ph), 4.60-4.23 (4H, m, H-3'+H-5'+NH), 4.20-3.97 (2H, m, H-4'+CHCH$_3$), 2.48-2.44 (1H, m, one of H-2'), 2.15-2.05 (1H, m, one of H-2'), 1.43-1.40 (3H, d, $^3$J=7.0 Hz, CHCH$_3$).

$^{13}$C-NMR (CDCl$_3$, 75 MHz): δ 21.2 (CHCH$_3$), 40.7 (C-2'), 50.8, 50.9 (CHCH$_3$), 66.6 (C-5'), 67.9 (CH$_2$Ph), 70.7, 71.1 (C-3'), 85.4, 85.5, 85.8, 86.1 (C-1', C-4'), 110.5 (C-5b), 111.9, 112.0 (C-5), 122.0, ('o', OPh), 128.7, 129.0, 129.1, 130.3 ('m', OPh+C-5a), 131.1 ('ipso', CH$_2$Ph), 135.4 ('p', OPh), 138.2 (C-6), 149.1 ('ipso', OPh), 150.0 (C-4), 162.1 (C-2), 173.9, 174.0 (COOCH$_2$Ph).

Synthesis of (E)-5-(2-bromovinyl)2'-deoxyuridine-5'-[phenyl-(methoxy-α,α-dimethylglycinyl)]-phosphate (CPF 26)

$C_{22}H_{27}BrN_3O_9P$, MW 588.34.

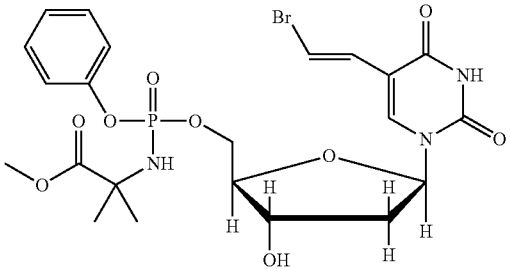

This was synthesised according to Standard procedure 5, using BVdU (200 mg, 0.60 mmol), phenyl-(methyl-2-amino-2-methylpropanoate)-phosphorochloridate (437.5 mg, 1.5 mmol), NMI (246.3 mg, 3.0 mmol, 239.1 μL) in THF (5 mL) for 4 hrs. The crude product was purified by column chromatography, eluting with chloroform/methanol 97:3 to give the pure product as a white foamy solid (117 mg, yield 33.1%).

$^{31}$P-NMR (CDCl$_3$, 121 MHz): δ 3.36, 3.14

$^1$H-NMR (CDCl$_3$; 300 MHz): δ 9.91 (1H, bs, H-3), 7.73, 7.65 (1H, 2s, H-6), 7.50-7.43 (1H 2d, $^3$J=13.6 Hz, H-5b), 7.41-7.02 (5H, m, OPh), 6.81-6.71 (1H, 2d, $^3$J=13.6 Hz, H-5a), 6.34-6.28 (1H, m, H1'), 4.55-4.17 (6H, m, H-5'+H-4'+H-3', NH, OH-3'), 3.78 (3H, s, CH$_3$O), 2.53-2.39 (1H, m, one of H-2'), 2.25-1.99 (1H, m, one of H-2'), 1.60 (6H, s, [CH$_3$]$_2$C).

$^{13}$C-NMR (CDCl$_3$; 75 MHz): δ 27.5, 27.4, 27.2 ([CH$_3$]$_2$C), 40.7, 40.6 (C-2'), 53.5 (CH$_3$O), 57.6 (C[CH$_3$]$_2$), 66.5, 66.2 (C-5'), 70.7, 71.1 (C-3'), 85.4, 85.6, 85.5, 85.9 (C-1', C-4'), 110.4 (C-5b), 111.9 (C-5), 120.5, 120.6 ('o', OPh), 125.7 ('p', OPh), 128.9 (C-5a), 130.3 ('m', OPh), 138.0, 138.3 (C-6), 149.8 ('ipso', OPh) 150.9, 150.8 (C-4), 162.0, 162.1 (C-2), 176.4, 176.2 (COOCH$_3$).

Synthesis of (E)-5-(2-bromovinyl)-2'-deoxyuridine-5'-[phenyl-(ethoxy-α,α-dimethylglycinyl)]-phosphate (CPF 27)

$C_{23}H_{29}BrN_3O_9P$, MW=602.37

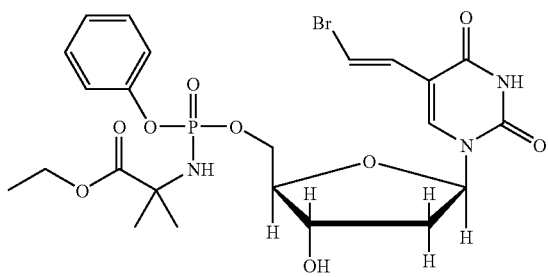

This was synthesised according to Standard procedure 5, using BVdU (200 mg, 0.60 mmol), phenyl-(ethyl-2-amino-2-methylpropanoate)-phosphorochloridate (458.0 mg, 1.5 mmol), NMI (246.3 mg, 3.0 mmol, 239.1 μL) in THF (5 mL) for 5 hrs. The crude product was purified by column chromatography, eluting with chloroform/methanol 97:3 to give the pure product as a white foamy solid (106 mg, yield 29.3%).

$^{31}$P-NMR (MeOD, 121 MHz): δ 3.91, 3.85

$^1$H-NMR (MeOD, 300 MHz): δ 7.84, 7.81 (1H, 2s, H-6), 7.44-7.20 (6H, m, OPh+H-5b), 6.88-6.81 (1H, 2d, $^3$J=13.6 Hz, H-5a), 6.34-6.28 (1H, m, H-1'), 4.50-4.34 (3H, m, H-5'+H-3'), 4.23-4.15 (3H, m, H-4'+CH$_3$CH$_2$O), 2.38-2.28 (1H, m, one of H-2'), 2.22-2.09 (1H, m, one of H-2'), 1.51 (6H, s, [CH$_3$]$_2$C), 1.29 (3H, t, $^3$J=7 Hz, CH$_3$CH$_2$O)

$^{13}$C-NMR (MeOD, 75 MHz): δ 14.9 (CH$_3$CH$_2$O) 27.9, 28.3 ([CH$_3$]$_2$C), 41.5 (C-2'), 58.51 (C[CH$_3$]$_2$), 63.1 (CH$_3$CH$_2$O), 68.2 (C-5'), 72.6 (C-3'), 87.1, 87.4 (C-1', C-4'), 109.6 (C-5b), 112.7 (C-5b), 122.0, 122.1, 122.2, ('o', OPh), 126.7 ('p', OPh), 131.0, 131.2 (C-5a, 'm' OPh), 140.4 (C-6), 151.4 ('ipso', OPh) 152.5 (C-4), 164.0 (C-2), 177.2 (COOCH$_2$CH$_3$).

Synthesis of (E)-5-(2-bromovinyl)-2'-deoxyuridine-5'-[phenyl-(benzoxy-α,α-dimethylglycinyl)]-phosphate (CPF 14)

$C_{28}H_{31}BrN_3O_9P$, MW=664.44.

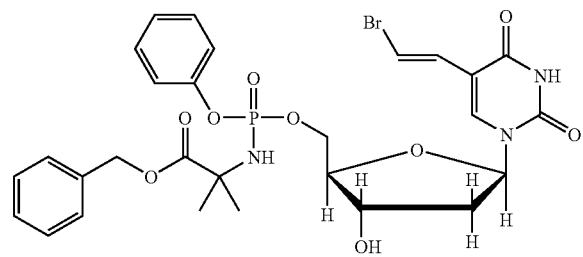

This was synthesised according to Standard procedure 5, using BVdU (242 mg, 0.73 mmol), phenyl-(benzyl-2-amino-2-methylpropanoate)-phosphorochloridate (533.0 mg, 2.0 mmol), NMI (298.0 mg, 3.63 mmol, 289 μL) in THF (5 mL) for 4 hrs. The crude product was purified by column chromatography, eluting with chloroform/methanol 97:3 to give the pure product as a white foamy solid (129.0 mg, yield 26.7%).

$^{31}$P-NMR (CDCl$_3$, 121 MHz): δ 3.39, 3.12.

$^1$H-NMR (CDCl$_3$, 300 MHz): δ 9.92 (1H, bs, H-3), 7.67-7.60 (1H, 2s, H-6), 7.48-7.41 (1H, 2d, $^3$J=13.6 Hz, H-5b), 7.40-7.16 (10H. m, OPh+CH$_2$Ph), 6.78-6.67 (1H, 2d, $^3$J=13.6 Hz, H-5a), 6.31-6.25 (1H, m, H-1'), 5.18 (1H, s, CH$_2$Ph), 4.50-4.09 (6H, m, H-3'+H-5'+H-4', NH, OH-3'), 2.48-2.25 (1H, m, one of H-2'), 2.16-1.82 (1H, m, one of H-2'), 1.60 (6H, s, [CH$_3$]$_2$C).

$^{13}$C-NMR (CDCl$_3$, 75 MHz): δ 27.3, 27.4, 28.5 ([CH$_3$]$_2$C), 40.6, 40.7 (C-2'), 57.6, 57.6 (C[CH$_3$]$_2$), 66.2, 66.5 (C-5'), 68.1 (CH$_2$Ph), 70.6, 71.1 (C-3'), 85.4, 85.5, 85.6, 85.8 (C-1', C-4'), 110.4 (C-5b), 112.0 (C-5), 120.4, 120.5, 120.6, 125.7, 128.4, 128.5, 128.8, 128.9, 130.3 (OPh, C-5a), 135.7('ipso', CH$_2$Ph) 138.1, 138.3 (C-6), 149.8, 150.8, 150.9 ('ipso' OPh, C-4), 162.1 (C-2), 177.5, 175.7 (COOCH$_2$Ph).

Synthesis of (E)-5-(2-bromovinyl)-2'-deoxyuridine-5'-[4-nitrophenyl-(methoxy-α,α-dimethylglycinyl)]-phosphate (CPF 45)

$C_{22}H_{26}BrN_4O_{11}P$, MW=633.34.

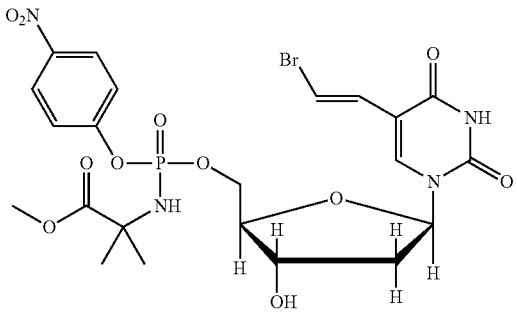

This was synthesised according to Standard procedure 5, using BVdU (150 mg, 0.45 mmol), 4-nitrophenyl-(methyl-2-amino-2-methylpropanoate)-phosphorochloridate (378.8 5 mg, 1.13 mmol), NMI (184.7 mg, 2.25 mmol, 179.4 μL) in THF (5 mL) for 3 hrs. The crude product was purified by column chromatography, eluting with dichloromethane/methanol 97:3 to give the pure product as a white foamy solid (145.7 mg, yield 50.9%).

$^{31}$P-NMR (MeOD, 121 MHz): δ 3.61, 3.56.

$^1$H-NMR (MeOD, 300 MHz): δ 8.30-8.25 (2H, 2d, $^3$J=9.0 Hz, OPh), 7.79-7.78 (1H, 2s, H-6), 7.49-7.46 (2H, d, $^3$J=9.0 Hz, OPh), 7.37-7.32 (1H, 2d, $^3$J=13.6 Hz, H-5b), 6.79-6.72 (1H, 2d, $^3$J=13.6 Hz, H-5a), 6.32-6.25 (1H, m, H-1'), 4.48-4.35 (3H, m, H-3'+H-5'), 4.15-4.14 (1H, m, H-4'), 3.71 (3H, s, CH$_3$O), 2.41-2.17 (2H, m, H-2'), 1.51 (6H, s, [CH$_3$]$_2$C.

$^{13}$C-NMR (CDCl$_3$, 75 MHz): δ 28.0, 28.1, 28.2, 28.3 ([CH$_3$]$_2$C), 41.4, 41.5 (C-2'), 53.6 (CH$_3$O), 58.7 (C[CH$_3$]$_2$), 68.5 (C-5'), 72.3, 72.4 (C-3'), 86.9, 87.0, 87.4, 87.5 (C-1', C-4'), 109.7 (C-5b), 112.6 (C-5), 122.8, 122.9 ('o', OPh), 127.0 ('m', OPh), 130.9 (C-5a), 140.5 (C-6), 146.5 ('p', OPh), 151.5 ('ipso', OPh), 157.3 (C-4), 164.0 (C-2), 177.5 (COOCH$_3$).

Synthesis of (E)-5-(2-bromovinyl)-2'-deoxyuridine-5'-[4-nitrophenyl-(ethoxy-α,α-dimethylglycinyl)]-phosphate (CPF 46)

$C_{23}H_{28}BrN_4O_{11}P$, MW=647.3.

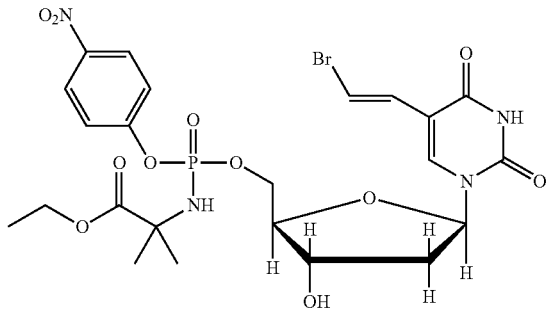

This was synthesised according to Standard procedure 5, using BVdU (150 mg, 0.45 mmol), 4-nitrophenyl-(ethyl-2-amino-2-methylpropanoate)-phosphorochloridate (442.1 mg, 1.26 mmol), NMI (184.7 mg, 2.25 mmol, 179.4 μL) in THF (5 mL) for 4 hrs. The crude product was purified by column chromatography, eluting with dichloromethane/methanol 97:3 to give the pure product as a white foamy solid (152.9 mg, yield 52.5%).

$^{31}$P-NMR (CDCl$_3$, 121 MHz): δ 3.00, 2.96.

$^1$H-NMR (CDCl$_3$, 300 MHz): δ 10.28 (1H, bs, H-3), 8.25.-8.12 (2H, 2d, $^3$J=9.0 Hz, OPh), 7.68-7.67 (1H, 2s, H-6), 7.46-7.32 (3H, m, OPh+H-5b), 6.69-6.67 (1H, 2d, $^3$J=13.5 Hz, H-5a), 6.32-6.26 (1H, m, H-1'), 4.75-4.36 (5H, m, H-3'+H-5'+NH), 4.25-4.17 (3H, m, OCH$_2$CH$_3$, H-4'), 2.60-2.98 (1H, m, one of H-2'), 2.31-2.10 (1H, m, one of H-2'), 1.58 (6H, s, [CH$_3$]$_2$C), 1.30-1.28 (3H, 2t, $^3$J=7.1 Hz, OCH$_2$CH$_3$).

$^{13}$C-NMR (CDCl$_3$, 75 MHz): δ 14.5 (CH$_3$CH$_2$O), 27.1, 27.2, 27.3, 27.4 ([CH$_3$]$_2$C), 40.6 (C-2'), 57.7 (C[CH$_3$]$_2$), 62.7 (CH$_3$CH$_2$O), 67.0 (C-5'), 71.0, 71.2 (C-3'), 85.4, 85.9, 86.1 (C-1', C-4'), 110.3 (C-5b), 111.9 (C-5), 121.2, 121.3 ('o', OPh), 126.2 ('m', OPh), 128.8 (C-5a), 138.4 (C-6), 145.0 ('p', OPh), 150.0 (C-4), 155.7-155.9 ('ipso', OPh), 162.2 (C-2), 175.0-175.1 (COOCH$_2$CH$_3$).

Synthesis of (E)-5-(2-bromovinyl)-2'-deoxyuridine-5'-[4-nitrophenyl-(benzoxy-α,α-dimethylglycinyl)]-phosphate (CPF 47)

$C_{28}H_{30}BrN_4O_{11}P$, MW=709.44.

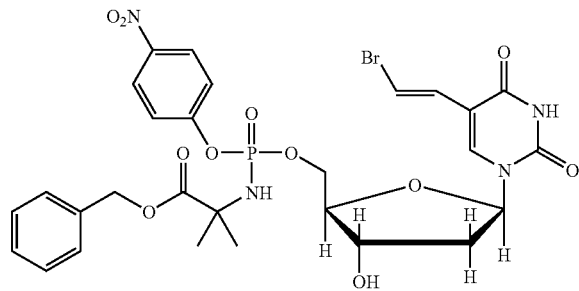

This was synthesised according to Standard procedure 5, using BVdU (100 mg, 0.30 mmol), 4-nitrophenyl-(benzyl-2-amino-2-methylpropanoate)-phosphorochloridate (309.6 mg, 1.07 mmol), NMI (123.7 mg, 1.5 mmol, 120.1 μL) in THF (5 mL) for 5 hrs. The crude product was purified by column chromatography, eluting with dichloromethane/methanol 97:3 to give the pure product as a white foamy solid (160.2 mg, yield 50.2%).

$^{31}$P-NMR (CDCl$_3$, 121 MHz): δ 2.95, 2.89.

$^1$H-NMR (CDCl$_3$, 300 MHz): δ 10.16 (1H, bs, H-3), 8.26-8.24 (2H, 2d, $^3$J=9.1 Hz, OPh), 7.71-7.69 (1H, 2s, H-6), 7.48-7.37 (8H, m, OPh+CH$_2$Ph, H-5b), 6.75-6.72 (1H, 2d, $^3$J=13.5 Hz, H-5a), 6.36-6.29 (1H, m, H-1'), 5.24 (2H, s, CH$_2$Ph), 4.81-4.40 (5H, m, H-3'+H-5'+OH-3', NH, 4.22-4.21 (1H, m, H-4'), 2.57-2.36 (1H, m, one of H-2') 2.27-2.22 (1H, m, one of H-2'), 1.64 (6H, s, [CH$_3$]$_2$C).

$^{13}$C-NMR (CDCl$_3$, 75 MHz): δ 27.4 ([CH$_3$]$_2$C), 40.6 (C-2'), 57.8 (C[CH$_3$]$_2$), 67.0 (C-5'), 68.2 (CH$_2$Ph), 71.1, 71.2 (C-3'), 85.3, 86.2 (C-1', C-4'), 110.5 (C-5b), 111.9 (C-5), 111.9 (C-5), 121.2, 126.2, 128.5, 128.8, 129.0, 129.1 ('o', 'm', 'p', CH$_2$Ph+OPh+C-5a), 135.5 ('ipso', CH$_2$Ph), (C-5a), 138.4 (C-6), 145.0 ('p', OPh), 150.0 (C-4), 155.7 ('ipso', OPh), 162.2 (C-2), 175.4-175.5 (COOCH$_2$Ph).

Synthesis of (E)-5-(2-bromovinyl)-2'-deoxyuridine-5'-[4-chlorophenyl-(methoxy-α,α-dimethylglycinyl)]-phosphate (CPF 42)

$C_{22}H_{26}BrClN_3O_9P$, MW=622.79.

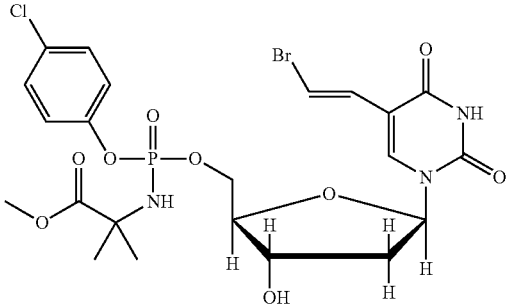

This was synthesised according to Standard procedure 5, using BVdU (150 mg, 0.45 mmol), 4-chlorophenyl-(methyl-2-amino-2-methylpropanoate)-phosphorochloridate (440.2 mg, 1.35 mmol), NMI (184.7 mg, 2.25 mmol, 179.4 μL) in THF (5 mL) for 6 hrs. The crude product was purified by column chromatography, eluting with dichloromethane/methanol 97:3 to give the pure product as a white foamy solid (146.7 mg, yield 56.5%).

$^{31}$P-NMR (MeOD, 121 MHz): δ 3.98 (s).

$^1$H-NMR (MeOD, 300 MHz): δ), 7.71-7.69 (1H, 2s, H-6), 7.31-7.13 (5H, m, OPh+H-5b) 6.73-6.66 (1H, 2d, $^3$J=13.6 Hz, H-5a), 6.23-6.16 (1H, m, H-1'), 4.39-4.22 (3H, m, H-3'+H-5'), 4.05-4.03 (1H, m, H-4'), 3.61 (3H, s, CH$_3$O), 2.29-2.19 (1H, m, one of H2'), 2.15-2.05 (1H, m, one of H-2'), 1.38 (6H, s, [CH$_3$]$_2$C).

$^{13}$C-NMR (CDCl$_3$; 75 MHz): δ 28.0, 28.2, 28.3, 28.4 ([CH$_3$]$_2$C), 41.5, 41.6 (C-2'), 53.5, 53.6 (CH$_3$O), 58.6 (C[CH$_3$]$_2$), 68.2 (C-5'), 72.4, 72.5 (C-3'), 87.1, 87.2, 87.3, 87.4 (C-1', C-4'), 109.7 (C-5b), 112.7 (C-5), 123.7, 123.8 ('o', OPh), 130.9, 131.1 ('m', OPh+C-5a), 131.9 ('p', OPh), 140.4 (C-6), 151.1, 151.2, 151.4 ('ipso', OPh+C-4), 164.0 (C-2), 177.6, 177.7 (COOCH$_3$).

Synthesis of (E)-5-(2-bromovinyl)-2'-deoxyuridine-5'-[4-chlorophenyl-(ethoxy-α,α-dimethylglycinyl)]-phosphate (CPF 43)

$C_{23}H_{28}BrClN_3O_9P$, MW=636.81.

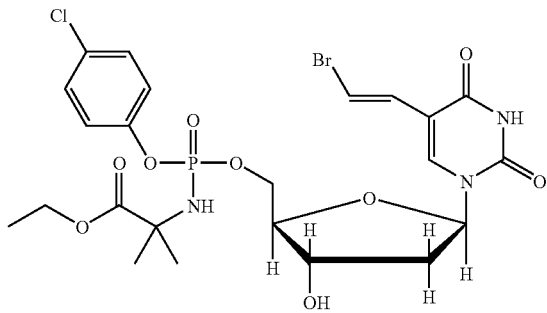

This was synthesised according to Standard procedure 5, using BVdU (150 mg, 0.45 mmol), 4-chlorophenyl-(ethyl-2-amino-2-methylpropanoate)-phosphorochloridate (413.3 mg, 1.22 mmol), NMI (184.7 mg, 2.25 mmol, 179.3 µL) in THF (5 mL) for 16 hrs. The crude product was purified by column chromatography, eluting with dichloromethane/methanol 97:3 to give the pure product as a white foamy solid (74 mg, yield 25.8%).

$^{31}$P-NMR (CDCl$_3$, 121 MHz): δ 3.47, 3.33.

$^1$H-NMR (CDCl$_3$, 300 MHz): δ 10.03-9.99 (1H, 2bs, H-3), 7.70-7.67 (1H, 2s, H-6), 7.47-7.43 (1H, 2d, $^3$J=13.6 Hz, H-5b), 7.35-7.20 (4H, m, OPh), 6.77-6.68 (1H, 2d, $^3$J=13.6 Hz, H-5a), 6.33-6.27 (1H, m, H-1'), 4.55-4.29 (5H, m, H-3'+H-5'+OH-3'+NH), 4.22-4.17 (2H, q, $^3$J=7.1 Hz, OCH$_2$CH$_3$+H-4'), 2.53-2.42 (1H, m, one of H-2'), 2.22-2.08 (1H, m, one of H-2'), 1.57-1.54 (6H, 2s, [CH$_3$]$_2$C), 1.31-1.30 (3H, 2t, $^3$J=7.1 Hz, OCH$_2$CH$_3$).

$^{13}$C-NMR (CDCl$_3$, 75 MHz): δ 14.5 (CH$_3$CH$_2$O), 27.2, 27.3, 27.4 ([CH$_3$]$_2$C), 40.7 (C-2'), 57.6 (C[CH$_3$]$_2$), 62.6 (CH$_3$CH$_2$O), 66.5, 66.6 (C-5'), 70.8, 71.1 (C-3'), 85.5, 85.74, 86.0 (C-1', C-4'), 110.4 (C-5b), 112.0 (C-5), 121.9, 122.0, 122.1 ('o', OPh), 128.9, 130.2 ('m', OPh+C-5a), 130.9 ('p', OPh), 138.3 (C-6), 149.4 ('ipso', OPh), 149.9 (C-4), 162.1, 162.2 (C-2), 175.7-175.9 (COOCH$_2$CH$_3$).

Synthesis of (E)-5-(2-bromovinyl)-2'-deoxyuridine-5'-[4-chlorophenyl-(benzoxy-α,α-dimethylglycinyl)]-phosphate (CPF 44)

$C_{28}H_{30}BrClN_3O_9P$, MW=698.88.

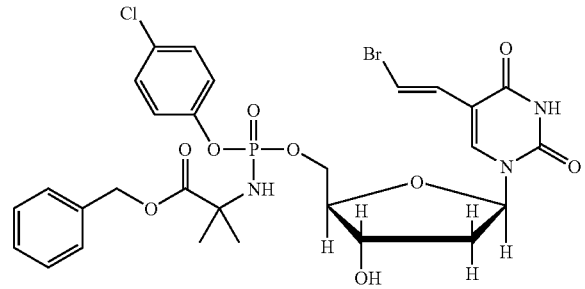

This was synthesised according to Standard procedure 5, using BVdU (150 mg, 0.45 mmol), 4-chlorophenyl-(benzyl-2-amino-2-methylpropanoate)-phosphorochloridate (505.0 mg, 1.25 mmol), NMI (184.7 mg, 2.25 mmol, 179.3 µL) in THF (5 mL) for 16 hrs. The crude product was purified by column chromatography, eluting with dichloromethane/methanol 97:3 to give the pure product as a white foamy solid (134.8 mg, yield 42.9%).

$^{31}$P-NMR (CDCl$_3$, 121 MHz): δ 3.44, 3.26.

$^1$H-NMR (CDCl$_3$, 300 MHz): δ 9.96-9.93 (1H, 2bs, H-3), 7.66-7.65 (1H, 2s, H-6), 7.47-7.41 (1H, 2d, $^3$J=13.5, H-5b), 7.39-7.18 (9H, m, OPh+CH$_2$Ph) 6.74-6.69 (1H, 2d, $^3$J=13.5 Hz, H-5a), 6.31-6.25 (1H, m, H-1'), 5.19 (2H, CH$_2$Ph), 4.51-4.29 (4H, m, H-3'+H-5'+NH), 4.15-4.12 (2H, m, H-4'+OH-3'), 2.48-2.40 (1H, m, one of H-2'), 2.18-2.05 (1H, m, one of H-2'), 1.60-1.59 (6H, 2s, [CH$_3$]$_2$C).

$^{13}$C-NMR (CDCl$_3$, 75 MHz): δ 27.1, 27.5 ([CH$_3$]$_2$C), 40.7 (C-2'), 57.7 (C[CH$_3$]$_2$), 66.4, 66.6 (C-5'), 68.2 (CH$_2$Ph), 70.7, 71.1 (C-3'), 85.4, 85.5, 85.7, 86.0 (C-1', C-4'), 110.5 (C-5b), 112.0 (C-5), 121.9, 122.0, 128.4, 128.5, 128.9, 129.1 ('o', 'm', 'p', CH$_2$Ph+OPh+C-5a), 131.0 ('ipso', CH$_2$Ph), 135.6 ('p', OPh), 138.1 (C-6), 149.3 ('ipso', OPh), 149.8 (C-4), 162.1 (C-2), 175.6 (COOCH$_2$Ph).

Synthesis of (E)-5-(2-bromovinyl)-2'-deoxyuridine-5'-[para-(trifluoromethyl)phenyl-(benzoxy-α,α-dimethylglycinyl)]-phosphate (CPF 48)

$C_{29}H_{30}BrF_3N_3O_9P$, MW=732.44.

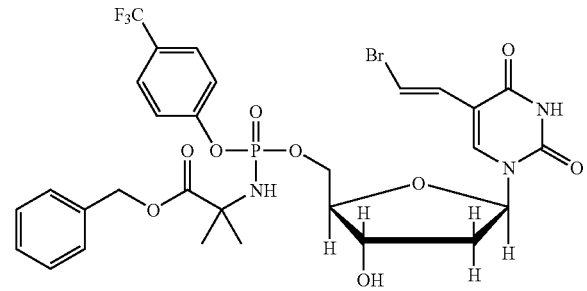

This was synthesised according to Standard procedure 5, using BVdU (150 mg, 0.45 mmol), 4-(trifluoromethyl)-phenyl-(benzyl-2-amino-2-methylpropanoate)-phosphorochloridate (529.4.5 mg, 1.22 mmol), NMI (184.7 mg, 2.25 mmol, 179.4 µL) in THF (5 mL) for 4 hrs. The crude product was purified by column chromatography, eluting with dichloromethane/methanol 97:3 to give the pure product as a white foamy solid (142.1 mg, yield 43.1%).

$^{31}$P-NMR (CDCl$_3$, 121 MHz): δ 3.16, 3.01.

$^1$H-NMR (CDCl$_3$, 300 MHz): δ 10.06-10.02 (1H, 2bs, H-3), 7.67-7.66 (1H, s, H-6), 7.64-7.60 (2H, 2d, $^3$J=8.8 Hz, OPh), 7.46-7.32 (8H, m, OPh+CH$_2$Ph+H-5b), 6.77-6.68 (1H, 2d, $^3$J=13.6 Hz, H-5a), 6.31-6.26 (1H, m, H-1'), 5.18 (2H, s, CH$_2$Ph), 4.61-4.32 (4H, m, H-3'+H-5'+NH), 4.16-4.15 (2H, m, H-4'+OH-3'), 2.48-2.41 (1H, m, one of H-2'), 2.23-2.09 (1H, m, one of H-2'), 1.60-1.58 (6H, 2s, C[CH$_3$]$_2$)

$^{13}$C-NMR (CDCl$_3$, 75 MHz): δ 27.0, 27.4, 27.5 (C[CH$_3$]$_2$), 40.6 (C-2'), 57.7, 57.8 (C[CH$_3$]$_2$), 66.8, 66.5 (C-5'), 68.2 (CH$_2$Ph), 70.8, 71.1 (C-3'), 85.4, 85.7, 86.0 (C-1', C-4'), 110.4 (C-5b), 111.9 (C-5), 120.8, 120.9, 121.0, 127.6, 127.7, 128.0, 128.5, 128.8, 129.0 ('o', 'm', 'p', OPh+CH$_2$Ph+C-5a), 124.2 (CF$_3$, J=267 Hz), 135.6 ('ipso', CH$_2$Ph), 138.2 (C-6), 149.9 (C-4), 153.3 ('ipso', OPh), 162.1 (C-2), 175.4 (COOCH$_2$Ph).

Synthesis of (E)-5-(2-Bromovinyl)-2'-deoxyuridine-5'-[phenyl-(methoxy-α, α-cycloleucinyl)]-phosphate (CPF 16)

$C_{24}H_{29}BrN_3O_9P$, MW=614.38.

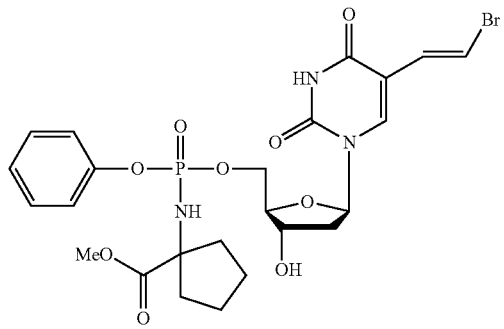

This was synthesised according to Standard procedure 5, using BVdU (250 mg, 0.75 mmol), Phenyl-(methoxy-α,α-cycloleucinyl)-phosphorochloridate (589 mg, 1.87 mmol), NMI (6.2 mmol, 415 μL) in THF (7 mL) for 3 hrs. The crude product was purified by column chromatography, eluting with $CH_2Cl_2$/Methanol 97:3 to give the pure product as a white foamy solid (234 mg, yield 51%).

$^{31}$P-NMR (CDCl$_3$, 121 MHz): δ 3.87, 3.82.

$^1$H-NMR (CDCl$_3$; 300 MHz): δ 10.35-10.2 (1H, bs, H-3), 7.65 (1H, 2×s, H-6), 7.44-7.39 (1H, 2d, $^3$J=13 Hz, H-5b), 7.37-7.15 (5H, m, OPh), 6.8 (1H, 2d, $^3$J=13 Hz, H-5a), 6.30 (1H, 2t, $^3$J=6 Hz, H1'), 4.4-4.2 (4H, m, H-5', H-3', NH), 4.1 (1H, H-4'), 3.72 (3H, 2s, CH$_3$O), 2.49-2.40 (1H, m, one of H-2'), 2.35-2.01 (5H, m, one of H-2'+4H cyclopentane), 1.8-1.6 (4H, m, 4H cyclopentane).

$^{13}$C-NMR (DMSO; 75 MHz): δ 24.4, 24,3, 24.2 (2CH$_2$ cyclopent), 39.2, 38.6, 38.5 (2CH$_2$ cyclopent), 40.0 (C-2'), 53.2 (CH$_3$O), 66.4 (Cq cyclopentane), 66.6 (C-5'), 70.9 (C-3'), 85.8, 85.6, 85.4, 85.3 (C-1', C-4'), 110.2 (C-5b), 111.9 (C-5), 120.7-120.6 ('o', OPh), 125.7 ('p', OPh), 129.0 (C-5a), 130.2 ('m', OPh), 138.5 (C-6), 149.9 (C-4), 150.9, 150.8 ('ipso', OPh), 162.3(C-2), 176.3, 176.2 (COOCH$_3$).

Synthesis of (E)-5-(2-Bromovinyl)-2'-deoxyuridine-5'-[phenyl-(ethoxy-α, α-cycloleucinyl)]-phosphate (CPF 17)

$C_{25}H_{31}BrN_3O_9P$, MW=628.41.

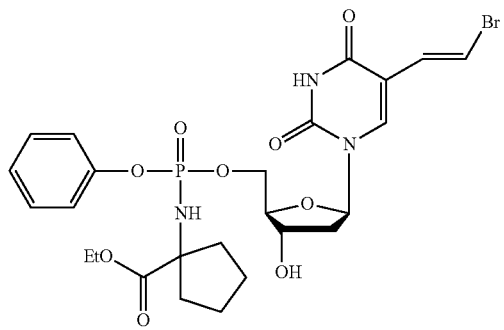

This was synthesised according to Standard procedure 5, using BVdU (250 mg, 0.75 mmol), Phenyl-(ethoxy-α,α-cycloleucinyl)-phosphorochloridate (642 mg, 1.87 mmol), NMI (6.2 mmol, 415 μL) in THF (7 mL) for 2 hrs. The crude product was purified by column chromatography, eluting with $CH_2Cl_2$/Methanol 97:3 to give the pure product as a white foamy solid (258 mg, yield 55%).

$^{31}$P-NMR (CDCl$_3$, 121 MHz): δ 4.23, 4.1.

$^1$H-NMR (CDCl$_3$, 300 MHz): δ 10.3-10.1 (1H, bs, H-3), 7.8-7.75 (1H, 2×s, H-6), 7.51 (1H, 2d, $^3$J=14 Hz, H-5b), 7.45-7.10 (5H, m, OPh), 6.8 (1H, 2d, $^3$J=14 Hz, H-5a), 6.22 (1H, 2t, $^3$J=4 Hz, H1'), 4.55-4.05 (7H, m, H-5', H-3', H-4', NH, CH$_3$CH$_2$O), 2.50-2.40 (1H, m, one of H-2'), 2.35-1.95 (5H, m, one of H-2'+4H cyclopentane), 1.95-1.75 (4H, m, 4H cyclopentane), 1.25 (3H, 2t, $^3$J=7 Hz, CH$_3$CH$_2$O).

$^{13}$C-NMR (CDCl$_3$, 75 MHz): δ 14.5 (CH$_3$CH$_2$O), 24.5, 24,4 (2CH$_2$ cyclopent), 39.2, 38.9 38.8, 38.4 (2CH$_2$ cyclopent), 40.6 (C-2'), 62.2, 62.1 (CH$_3$CH$_2$O), 66.2 (Cq cyclopentane), 66.6 (C-5'), 70.8 (C-3'), 85.7, 85.5 (C-1', C-4'), 110.2 (C-5b), 111.5 (C-5), 120.7, 120.6 ('o', OPh, 125.6 ('p', OPh), 129.7 (C-5a), 130.2 ('m', OPh), 138.5, 138.3 (C-6), 149.7 (C-4), 150.9, 150.8 ('ipso', OPh), 162.3 (C-2),176.3 (COOCH$_2$CH$_3$).

Synthesis of (E)-5-(2-Bromovinyl)-2'-deoxyuridine-5'-[phenyl-(benzoxy-α, α-cycloleucinyl)]-phosphate (CPF 18)

$C_{30}H_{33}BrN_3O_9P$, MW=690.48.

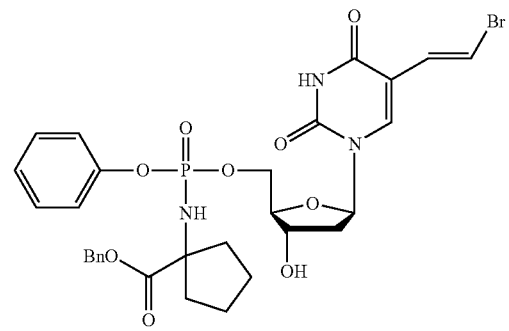

This was synthesised according to Standard procedure 5, using BVdU (200 mg, 0.6 mmol), Phenyl-(benzyloxy-α,α-cycloleucinyl)-phosphorochloridate (589 mg, 1.5 mmol), NMI (4.98 mmol, 332 μL) in THF (5 mL) for 10 hrs. The crude product was purified by column chromatography, eluting with $CH_2Cl_2$/Methanol 97:3 to give the pure product as a white foamy solid (127 mg, yield 31%).

$^{31}$P-NMR (CDCl$_3$, 121 MHz): δ 4.11, 4.01.

$^1$H-NMR (CDCl$_3$, 300 MHz): δ 10.2 (1H, bs, H-3), 7.8-7.6 (1H, 2×s, H-6), 7.45-7.4 (1H, 2d, $^3$J=14 Hz, H-5b), 7.40-7.10 (10H. m, OPh+CH$_2$Ph), 6.85 (1H, 2d, $^3$J=14 Hz, H-5a), 6.20 (1H, m, H-1'), 5.15 (1H, s, CH$_2$Ph), 4.4-4.2 (3H, m, H-3',H-4', NH), 4.1 (2H, m, H-5'), 2.45-2.35 (1H, m, one of H-2'), 2.35-1.95 (5H, m, one of H-2'+4H cyclopentane), 1.95-1.75 (4H, m, 4H cyclopentane).

$^{13}$C-NMR (CDCl$_3$, 75 MHz): δ 24.4, 24,3, 24.2 (2CH$_2$ cyclopent), 39.9, 39.7 38.6, 38.5 (2CH$_2$ cyclopent), 40.5 (C-2'), 66.2 (Cq cyclopentane), 66.5 (C-5'), 67.8 (CH$_2$Ph), 70.8, 70.7 (C-3'), 85.7, 85.6, 85.5, 85.4 (C-1', C-4'), 110.2 (C-5b), 111.8, 118.7 (C-5b), 120.7, 120.5 ('o', OPh), 125.7 ('p', OPh), 130.2, 129.0, 128.8, 128.7, 128.5 ('m' OPh, Bn, C-5a), 135.8('ipso', CH$_2$Ph) 138.4, 138.2 (C-6), 149.8 (C-4), 150.9, 150.8 ('ipso', OPh), 162.2 (C-2), 175.7, 175.5 (COOBn).

Synthesis of (E)-5-(2-Bromovinyl)-2'-deoxyuridine-5'-[para-nitrophenyl-(methoxy-α,α-cycloleucinyl)]-phosphate (CPF 19)

$C_{24}H_{28}BrN_4O_{11}P$, MW=659.38.

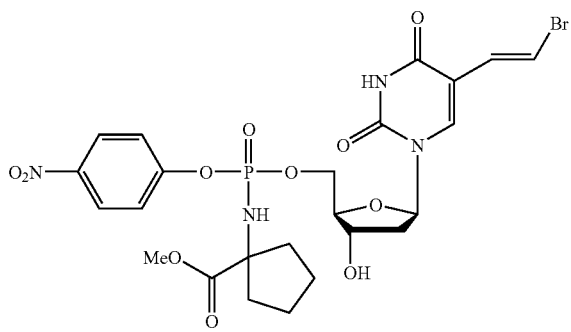

This was synthesised according to Standard procedure 5, using BVdU (200 mg, 0.60 mmol), para-nitrophenyl-(methoxy-α,α-cycloleucinyl)-phosphorochloridate (543 mg, 1.5 mmol), NMI (4.98 mmol, 332 μL) in THF (5 mL) for 2 hrs. The crude product was purified by column chromatography, eluting with $CH_2Cl_2$/Methanol 97:3 to give the pure product as a white foamy solid (239 mg, yield 60%).

$^{31}$P-NMR (CDCl$_3$, 121 MHz): δ 3.73.

$^1$H-NMR (CDCl$_3$; 300 MHz): δ 10.5-10.2 (1H, bs, H-3), 8.35-8.25 (2H, d, $^3$J=6 Hz OPh) 7.8-7.75 (1H, 2×s, H-6), 7.47 (2H, d, $^3$J=6 Hz, OPh), 7.45-7.35 (1H, 2d, $^3$J=14 Hz, H-5b), 6.75-6.67 (1H, 2d, $^3$J=14 Hz, H-5a), 6.30 (1H, 2t, $^3$J=6 Hz, H1'), 4.65-4.4 (3H, m, H-5',H-3'), 4.25-4.20 (1H, m, H-4'), 3.79 (3H, s, CH$_3$O), 2.6-2.4 (1H, m, one of H-2'), 2.3-1.98 (5H, m, one of H-2'+4H cyclopentane), 1.9-1.76 (4H, m, 4H cyclopentane).

$^{13}$C-NMR (CDCl$_3$; 75 MHz): δ 24.4, 24,3, 24.2 (2CH$_2$ cyclopent), 39.2, 39.1 (2CH$_2$ cyclopent), 40.5 (C-2'), 53.4, 53.3 (CH$_3$O), 66.8 (Cq cyclopentane), 67.1 (C-5'), 70.9 (C-3'), 86.1, 86.0, 85.5, 85.4 (C-1', C-4'), 110.2 (C-5b), 111.8 (C-5), 121.3, 121.2 ('o', OPh), 126.2 ('m', OPh), 128.9 (C-5a), 138.6 (C-6), 144.9 ('ipso', OPh) 149.9 (C-4), 155.9, 155.8 ('p', OPh), 162.3 (C-2), 176.3 (COOCH$_3$).

Synthesis of (E)-5-(2-Bromovinyl)-2'-deoxyuridine-5'-[para-nitrophenyl-(ethoxy-α,α-cycloleucinyl)]-phosphate (CPF 20)

$C_{25}H_{30}BrN_3O_{11}P$, MW=673.4.

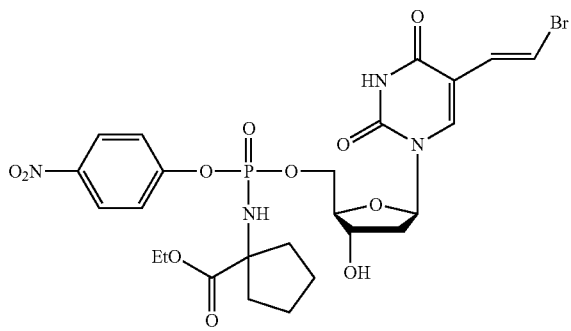

This was synthesised according to Standard procedure 5, using BVdU (200 mg, 0.60 mmol), para-nitrophenyl-(ethoxy-α,α-cycloleucinyl)-phosphorochloridate (563 mg, 1.5 mmol), NMI (4.98 mmol, 332 μL) in THF (5 mL) for 1 hr. The crude product was purified by column chromatography, eluting with $CH_2Cl_2$/Methanol 97:3 to give the pure product as a white foamy solid (240 mg, yield: 59%).

$^{31}$P-NMR (CDCl$_3$, 121 MHz): δ 3.83, 3.79.

$^1$H-NMR (CDCl$_3$, 300 MHz): δ 8.25-8.2 (2H,2d,$^3$J=9 Hz OPh), 7.66 (1H, s, H-6), 7.4 (2H, 2d, $^3$J=9 Hz, OPh), 7.3 (1H, 2d, $^3$J=14 Hz, H-5b), 6.85 (1H, 2d, $^3$J=14 Hz, H-5a), 6.3-6.2 (1H, m, H1'), 4.7-4.45 (4H, m, H-5', H-3', NH), 4.2-4.05 (3H, m, H-4', CH$_3$CH$_2$O), 2.55-2.4 (1H, m, one of H-2'), 2.2-1.95 (5H, m, one of H-2'+4H cyclopentane), 1.95-1.8 (4H, m, 4H cyclopentane), 1.2 (3H, 2t, $^3$J=8 Hz, CH$_3$CH$_2$O).

$^{13}$C-NMR (CDCl$_3$, 75 MHz): δ 14.9 (CH$_3$CH$_2$O), 24.5, 24,4 (2CH$_2$ cyclopent), 39.1, 39.0, 38.8 (2CH$_2$ cyclopent), 40.7 (C-2'), 62.4 (CH$_3$CH$_2$O), 66.5 (Cq cyclopentane), 67.0 (C-5'), 70.9 (C-3'), 85.9, 85.4 (C-1', C-4'), 110.2 (C-5b), 111.8 (C-5), 121.3 ('o', OPh), 126.2 ('m', OPh), 128.8 (C-5a), 138.5 (C-6), 144.9 ('ipso', OPh), 149.9 (C-4), 155.5 ('p', OPh), 162.3 (C-2), 175.8, 175.7 (COOCH$_2$CH$_3$).

Synthesis of (E)-5-(2-Bromovinyl)-2'-deoxyuridine-5'-[para-nitrophenyl-(benzoxy-α,α-cycloleucinyl)]-phosphate (CPF 21)

$C_{30}H_{32}BrN_4O_{11}P$, MW=735.47.

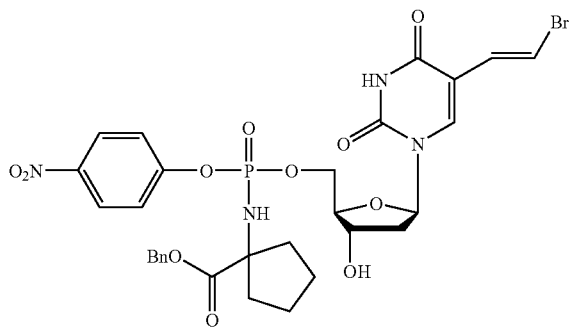

This was synthesised according to Standard procedure 5, using BVdU (200 mg, 0.60 mmol), para-nitrophenyl-(benzyloxy-α,α-cycloleucinyl)-phosphorochloridate (656 mg, 1.5 mmol), NMI (4.98 mmol, 332 μL) in THF (5 mL) for 3 hrs. The crude product was purified by column chromatography, eluting with $CH_2Cl_2$/Methanol 97:3 to give the pure product as a white foamy solid (269 mg, yield 61%).

$^{31}$P-NMR (CDCl$_3$, 121 MHz): δ 3.72.

$^1$H-NMR (CDCl$_3$, 300 MHz): δ 10.3 (1H, bs, H-3), 8.22-8.12 (2H, 2d, J=7 Hz, OPh), 7.65 (1H, 2×s, H-6), 7.45-7.30 (8H, m, H-5b+OPh+CH$_2$Ph), 6.72-6.65 (1H, 2d, $^3$J=14 Hz, H-5a), 6.28 (1H, 2t, $^3$J=6 Hz, H-1'), 5.15 (1H, d, CH$_2$Ph), 4.6-4.35 (4H, m, H-3', H-5', H-4', NH,), 2.55-2.4 (1H, m, one of H-2'), 2.3-1.92 (5H, m, one of H-2'+4H cyclopentane), 1.85-1.6 (4H, m, 4H cyclopentane).

$^{13}$C-NMR (CDCl$_3$, 75 MHz): δ 24.4, 24,3, 24.2 (2CH$_2$ cyclopent), 39.1, 38.9, 38.7 (2CH$_2$ cyclopent), 40.5 (C-2'), 66.9 (cyclopentane), 67.1 (C-5'), 68.0 (CH$_2$Ph), 70.9 (C-3'), 85.3, 85.0 (C-1', C-4'), 110.3 (C-5b), 111.8 (C-5), 121.2 ('o', OPh), 126.1 ('m', OPh), 129.0, 128.8 (Bn, C-5a), 135.7 ('ipso', CH$_2$Ph), 138.5 (C-6), 144.9 ('ipso', OPh), 149.9 (C-4), 155.8 ('p' OPh), 162.3 (C-2), 175.6 (COOBn).

Synthesis of (E)-5-(2-Bromovinyl)-2'-deoxyuridine-5'-[para-fluorophenyl-(methoxy-α,α-cycloleucinyl)]-phosphate (CPF 22)

C$_{24}$H$_{28}$BrFN$_3$O$_9$P, MW=632.37.

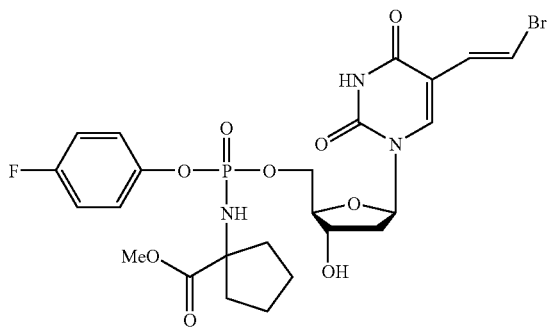

This was synthesised according to Standard procedure 5, using BVdU (200 mg, 0.60 mmol), para-fluorophenyl-(methoxy-α,α-cycloleucinyl)-phosphorochloridate (503 mg, 1.5 mmol), NMI (4.98 mmol, 332 μL) in THF (5 mL) for 2 hrs. The crude product was purified by column chromatography, eluting with CH$_2$Cl$_2$/Methanol 97:3 to give the pure product as a white foamy solid (251 mg, yield 66%).

$^{31}$P-NMR (CDCl$_3$, 121 MHz): δ 4.22.

$^{1}$H-NMR (CDCl$_3$; 300 MHz): δ 10.3 (1H, bs, H-3), 7.70 (1H, 2×s, H-6), 7.4 (1H, 2d, $^3$J=14 Hz, H-5b), 7.25-7.15 (2H, m, OPh), 7.1-6.95 (2H, m, OPh), 6.70 (1H, 2d, $^3$J=14 Hz, H-5a), 6.30-6.15 (1H, 2t, $^3$J=5 Hz, H1'), 4.55-4.05 (5H, m, H-5'+H-3', NH, H-4'), 3.72 (3H, 2s, CH$_3$O), 2.55-2.35 (1H, m, one of H-2'), 2.25-1.92 (5H, m, one of H-2'+4H cyclopentane), 1.85-1.6 (4H, m, 4H cyclopentane).

$^{13}$C-NMR (DMSO; 75 MHz): δ 24.4, 24,3, 24.2 (2CH$_2$ cyclopent), 39.3, 39.2, 38.9, 38.5 (2CH$_2$ cyclopent), 40.6 (C-2'), 53.3, 53.2 (CH$_3$O), 66.5 (Cq cyclopentane), 66.7 (C-5'), 70.9 (C-3'), 85.8, 85.7, 85.4 (C-1', C-4'), 110.2 (C-5b), 111.9 (C-5), 116.9, 116.6 ('o', OPh), 122,2, 122.0 ('m', O Ph), 128.5 (C-5a), 138.5 (C-6), 146.7 ('ipso', OPh) 149.9 (C-4), 158.5 ('p', OPh), 162.3(C-2), 176.4, 176.3 (COOCH$_3$).

Synthesis of (E)-5-(2-Bromovinyl)-2'-deoxyuridine-5'-[para-fluorophenyl- (ethoxy-α,α-cycloleucinyl)]-phosphate (CPF 23)

C$_{25}$H$_{30}$BrFN$_3$O$_9$P, MW=646.4.

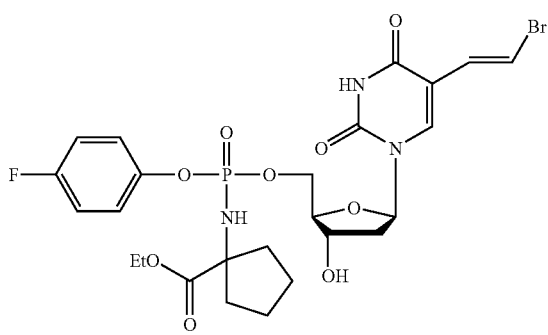

This was synthesised according to Standard procedure 5, using BVdU (200 mg, 0.60 mmol), para-fluorophenyl-(ethoxy-α,α-cycloleucinyl)-phosphorochloridate (524 mg, 1.5 mmol), NMI (4.98 mmol, 332 μL) in THF (5 mL) for 2 hrs. The crude product was purified by column chromatography, eluting with CH$_2$Cl$_2$/Methanol 97:3 to give the pure product as a white foamy solid (274 mg, yield 71%).

$^{31}$P-NMR (CDCl$_3$, 121 MHz): δ 5.30.

$^{1}$H-NMR (CDCl$_3$, 300 MHz): δ 10.35 (1H, bs, H-3), 7.7 (1H, 2×s, H-6), 7.44 (1H, 2d, $^3$J=14 Hz, H-5b), 7.25-7.15 (2H, m, OPh), 7.1-6.95 (2H, m, OPh), 6.7 (1H, 2d, $^3$J=14 Hz, H-5a), 6.30 (1H, 2t, $^3$J=6 Hz, H1'), 4.55,4.3 (3H, m, H-5', H-3'), 4.2-4.1 (4H, m, NH, H-4', CH$_3$CH$_2$O), 2.55-2.4 (1H, m, one of H-2'), 2.22-1.90 (5H, m, one of H-2'+4H cyclopentane), 1.8-1.6 (4H, m, 4H cyclopentane), 1.3-1.2 (3H, 2t, $^3$J=7 Hz, CH$_3$CH$_2$O).

$^{13}$C-NMR (CDCl$_3$, 75 MHz): δ 14.5 (CH$_3$CH$_2$O), 24.6, 24,4, 24.3 (2CH$_2$ cyclopent), 39.3, 39.2, 38.9, 38.6 (2CH$_2$ cyclopent), 40.6 (C-2'), 62.2 (CH$_3$CH$_2$O), 66.5 (Cq cyclopentane) 66.7 (C-5'), 71.0 (C-3'), 85.8, 85.7, 85.5, 85.4 (C-1', C-4'), 110.2 (C-5b), 111.9 (C-5), 116.9, 116.5 ('o', OPh), 122.2, 122.1 ('m', OPh), 129.0 (C-5a), 138.5 (C-6), 146.8, 146.7 ('ipso', OPh), 149.9 (C-4), 158.5 ('p', OPh), 162.3 (C-2), 175.9, 175.8 (COOCH$_2$CH$_3$).

Synthesis of (E)-5-(2-Bromovinyl)-2'-deoxyuridine-5'-[para-fluorophenyl-(benzoxy-α,α-cycloleucinyl)]-phosphate (CPF 24)

C$_{30}$H$_{32}$BrN$_3$O$_9$P, MW=708.47.

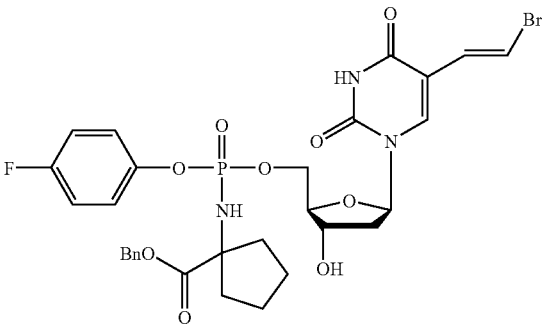

This was synthesised according to Standard procedure 5, using BVdU (200 mg, 0.60 mmol), para-fluorophenyl-(benzyloxy-α,α-cycloleucinyl)-phosphorochloridate (616 mg, 1.5 mmol), NMI (4.98 mmol, 332 μL) in THF (5 mL) for 2 hrs. The crude product was purified by column chromatography, eluting with CH$_2$Cl$_2$/Methanol 97:3 to give the pure product as a white foamy solid (283 mg, yield 67%).

$^{31}$P-NMR (CDCl$_3$, 121 MHz): δ 4.27.

$^{1}$H-NMR (CDCl$_3$, 300 MHz): δ 10.3-9.85 (1H, bs, H-3), 7.65 (1H, 2×s, H-6), 7.45-7.35 (1H, 2d, $^3$J=14 Hz, H-5b), 7.40-7.30 (5H. m, CH$_2$Ph), 7.25-7.15 (2H, m, OPh), 7.05-6.95 (2H, m, OPh), 6.71 (1H, 2d, $^3$J=14 Hz, H-5a), 6.27 (1H, 2t, $^3$J=6 Hz, H-1'), 5.15 (1H, s, CH$_2$Ph), 4.45 (1H, m, H-3'), 4.40-4.30 (2H, m, H-5') 4.20-4.05 (2H, m, H-4', NH), 2.5-2.4 (1H, m, one of H-2'), 2.25-1.9 (5H, m, one of H-2'+4H cyclopentane), 1.8-1.6 (4H, m, 4H cyclopentane).

$^{13}$C-NMR (CDCl$_3$, 75 MHz): δ 24.5, 24,3, 24.2 (2CH$_2$ cyclopent), 39.7, 39.6, 39.3, 39.2 (2CH$_2$ cyclopent), 40.5, 40.0 (C-2'), 66.6 (Cq cyclopentane), 67.2, 66.7 (C-5'), 67.9 (CH$_2$Ph), 70.8, 70.7 (C-3'), 85.8, 85.7, 85.4, 85.3 (C-1', C-4'), 110.3 (C-5b), 111.8 (C-5), 116.9, 116.6 ('o', OPh), 122.2, 122.1 ('m', OPh), 129.0, 128.9, 128.6, 128.5 (Bn, C-5a), 135.8('ipso', CH$_2$Ph) 138.5 (C-6), 146.8, 146.7 ('ipso' OPh), 149.9 (C-4), 158.5 ('p' OPh), 162.3 (C-2), 175.7, 175.0 (COOBn).

Synthesis of (E)-5-(2-Bromovinyl)-2'-deoxyuridine-5'-[para-chlorophenyl-(methoxy-α,α-cycloleucinyl)]-phosphate (CPF 32)

$C_{24}H_{28}BrClN_3O_9P$, MW=648.82.

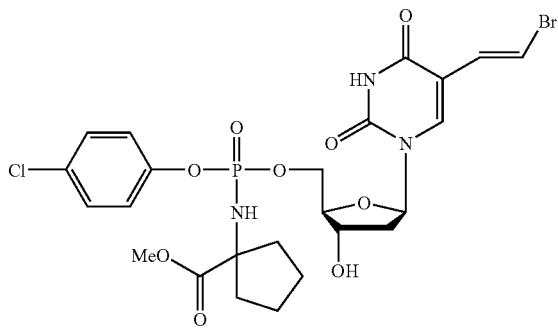

This was synthesised according to Standard procedure 5, using BVdU (150 mg, 0.45 mmol), para-chlorophenyl-(methoxy-α,α-cycloleucinyl)-phosphorochloridate (475 mg, 1.35 mmol), NMI (4.5 mmol, 300 μL) in THF (5 mL) for 2 hrs. The crude product was purified by column chromatography, eluting with $CH_2Cl_2$/Methanol 97:3 to give the pure product as a white foamy solid (187 mg, yield 64%).

$^{31}$P-NMR (MeOD, 121 MHz): δ 4.64.

$^1$H-NMR (MeOD; 300 MHz): δ 7.75 (1H, 2×s, H-6), 7.32 (1H, 2d, $^3$J=14 Hz, H-5b), 7.32-7.27 (2H, m, OPh), 7.20-7.11 (2H, m, OPh), 6.72 (1H, 2d, $^3$J=14 Hz, H-5a), 6.27-6.20 (1H, 2t, $^3$J=6 Hz, H1'), 4.35 (1H, m, H-3'), 4.30 (2H, m, H-5') 4.1 (2H, m, H-4'), 3.72 (3H, 2s, $CH_3O$), 2.32-2.20 (1H, m, one of H-2'), 2.20-1.92 (5H, m, one of H-2'+4H cyclopentane), 1.8-1.6 (4H, m, 4H cyclopentane).

$^{13}$C-NMR (MeOD; 75 MHz): δ 25.7, 25.6 (2CH$_2$ cyclopent), 41.7, 41.6, 41.4, 41.3 (2CH$_2$ cyclopent), 42.7 (C-2'), 54.1, 53.9 (CH$_3$O), 67.8 (Cq cyclopentane), 69.1, 69.0 (C-5'), 73.8 (C-3'), 88.4, 88.3, 88.2 (C-1', C-4'), 110.2 (C-5b), 111.8 (C-5), 122.1, 121.9 ('o', OPh), 128.9 (C-5a), 130.6 ('m', OPh), 130.8 ('p', OPh), 138.5 (C-6), 149.5, 149.4 ('ipso', OPh), 149.9 (C-4), 162.2(C-2), 175.6 (COOCH$_3$).

Synthesis of (E)-5-(2-Bromovinyl)-2'-deoxyuridine-5'-[para-chlorophenyl-(ethoxy-α,α-cycloleucinyl)]-phosphate (CPF 33)

$C_{25}H_{30}BrClN_3O_9P$, MW=662.85.

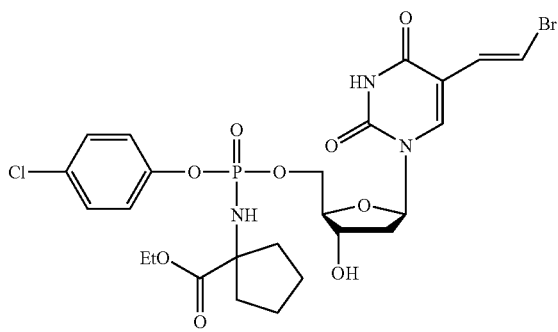

This was synthesised according to Standard procedure 5, using BVdU (150 mg, 0.45 mmol), para-chlorophenyl-(ethoxy-α,α-cycloleucinyl)-phosphorochloridate (495 mg, 1.35 mmol), NMI (4.5 mmol, 300 μL) in THF (5 mL) for 2 hrs. The crude product was purified by column chromatography, eluting with $CH_2Cl_2$/Methanol 97:3 to give the pure product as a white foamy solid (240 mg, yield 66%).

$^{31}$P-NMR (CDCl$_3$, 121 MHz): δ 4.15.

$^1$H-NMR (CDCl$_3$, 300 MHz): δ 10.25-10.1 (1H, bs, H-3), 7.65 (1H, 2×s, H-6), 7.4-7.3 (1H, 2d, $^3$J=14 Hz, H-5b), 7.25-7.20 (2H, m, OPh), 7.20-7.10 (2H, m, OPh), 6.75 (1H, 2d, $^3$J=14 Hz, H-5a), 6.20 (1H, m, H1'), 4.35 (3H, m, H-3', H-5'), 4.2-4.0 (4H, m, H-4', NH, CH$_3$CH$_2$O), 2.45-2.25 (1H, m, one of H-2'), 2.25-1.85 (5H, m, one of H-2'+4H cyclopentane), 1.75-1.55 (4H, m, 4H cyclopentane), 1.2 (3H, 2t, $^3$J=7 Hz, CH$_3$CH$_2$O).

$^{13}$C-NMR (CDCl$_3$, 75 MHz): δ 14.5 (CH$_3$CH$_2$O), 24.5, 24,4 (2CH$_2$ cyclopent), 39.3, 39.2, 38.8, 38.6 (2CH$_2$ cyclopent), 40.5 (C-2'), 62.3 (CH$_3$CH$_2$O), 66.1 (Cq cyclopentane), 66.7 (C-5'), 70.8 (C-3'), 85.8, 85.4 (C-1', C-4'), 110.3 (C-5b), 111.9 (C-5), 122.1, 121.9 ('o', OPh), 129.0 (C-5a), 130.2 ('m', OPh), 130.8 ('p', OPh), 138.5 (C-6), 149.5, 149.4 ('ipso', OPh), 149.9 (C-4), 162.3 (C-2), 175.9 (COOCH$_2$CH$_3$).

Synthesis of (E)-5-(2-Bromovinyl)-2'-deoxyuridine-5'-[para-chlorophenyl-(benzoxy-α,α-cycloleucinyl)]-phosphate (CPF 34)

$C_{30}H_{32}BrClN_3O_9P$, MW=724.92.

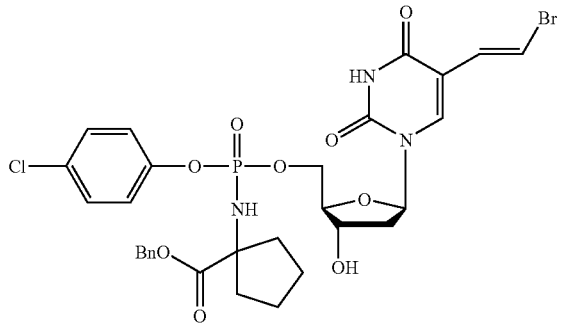

This was synthesised according to Standard procedure 5, using BVdU (150 mg, 0.45 mmol), para-chlorophenyl-(benzyloxy-α,α-cycloleucinyl)-phosphorochloridate (578 mg, 1.35 mmol), NMI (4.5 mmol, 300 μL) in THF (5 mL) for 2 hrs. The crude product was purified by column chromatography, eluting with $CH_2Cl_2$/Methanol 97:3 to give the pure product as a white foamy solid (222 mg, yield 68%).

$^{31}$P-NMR (CDCl$_3$, 121 MHz): δ 4.11, 4.05.

$^1$H-NMR (CDCl$_3$, 300 MHz): δ 7.65 (1H, 2×s, H-6), 7.45-7.29 (10H, m, H-5b, 2H OPh+CH$_2$Ph), 7.20-7.15 (2H, m, OPh), 6.75-6.67 (1H, 2d, $^3$J=14 Hz, H-5a), 6.28 (1H, 2t, $^3$J=6 Hz, H-1'), 5.15 (1H, 2s, CH$_2$Ph), 4.5 (1H, m, H-3'), 4.35 (2H, m, H-5') 4.1 (H, m, H-4'), 4.00 (1H, m, NH), 2.48-2.35 (1H, m, one of H-2'), 2.3-1.92 (5H, m, one of H-2'+4H cyclopentane), 1.8-1.6 (4H, m, 4H cyclopentane).

$^{13}$C-NMR (CDCl$_3$, 75 MHz): δ 24.5, 24.4, 24,3, 24.2 (2CH$_2$ cyclopent), 39.3, 38.8, 38.6 (2CH$_2$ cyclopent), 40.5 (C-2'), 66.7 (Cq cyclopentane), 67.9 (CH$_2$Ph), 68.4 (C-5'), 70.7 (C-3'), 85.7, 85.7, 85.4, 85.3 (C-1', C-4'), 110.3 (C-5b), 111.8 (C-5), 122.0, 121.9 ('o', OPh), 129.1, 128.3, 128.2 (Bn, 'm', OPh), 130.2 (C-5a), 135.8 ('ipso', CH$_2$Ph), 136.3 ('p' OPh), 138.2 (C-6), 149.5, 149.3 ('ipso', OPh), 149.9 (C-4), 162.2 (C-2), 175.7, 175.5 (COOBn).

Synthesis of (E)-5-(2-Bromovinyl)-2'-deoxyuridine-5'-[para-trifluorophenyl-(methoxy-α,α-cycloleucinyl)]-phosphate (CPF 28)

$C_{25}H_{28}BrF_3N_3O_9P$, MW=682.38.

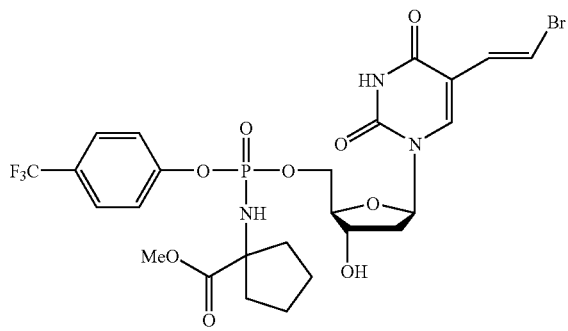

This was synthesised according to Standard procedure 5, using BVdU (150 mg, 0.45 mmol), para-trifluorophenyl-(methoxy-α,α-cycloleucinyl)-phosphorochloridate (521 mg, 1.35 mmol), NMI (4.5 mmol, 300 μL) in THF (5 mL) for 2 hrs. The crude product was purified by column chromatography, eluting with $CH_2Cl_2$/Methanol 97:3 to give the pure product as a white foamy solid (199 mg, yield 65%).

$^{31}$P-NMR (CDCl$_3$, 121 MHz): δ 3.80.

$^{1}$H-NMR (CDCl$_3$; 300 MHz): δ 7.70 (1H, 2s, H-6), 7.55 (1H, 2d, $^{3}$J=14 Hz, H-5b), 7.45-7.32 (4H, m, OPh), 6.72 (1H, 2d, $^{3}$J=14 Hz, H-5a), 6.28 (1H, 2t,$^{3}$J=6 Hz, H1'), 4.55 (1H, m, H-3'), 4.45 (2H, m, H-5'), 4.25 (1H, H-4'), 4.15 (1H, NH), 3.71 (3H, 2s, CH$_3$O), 2.6-2.4 (1H, m, one of H-2'), 2.3-1.9 (5H, m, one of H-2'+4H cyclopentane), 1.85-1.6 (4H, m 4H cyclopentane).

$^{13}$C-NMR (CDCl$_3$; 75 MHz): δ 24.4, 24,3, 24.2 (2CH$_2$ cyclopent), 39.2, 39.1, 38.8, 38.6 (2CH$_2$ cyclopent), 40.5 (C-2'), 53.9 (CH$_3$O), 66.3 (Cq cyclopentane), 66.8 (C-5'), 70.9 (C-3'), 85.8, 85.4 (C-1', C-4'), 110.3 (C-5b), 111.9 (C-5), 125.1 (d, J=270 Hz, CF$_3$), 127.1, 127.0 ('o', OPh), 127.8 ('m', OPh), 128.9 (C-5a), 129.0 ('p', q, J=32 Hz, OPh), 138.5 (C-6), 149.9 (C-4), 153.5 ('ipso', OPh), 162.2 (C-2), 176.3, 176.2 (COOCH$_3$).

Synthesis of (E)-5-(2-Bromovinyl)-2'-deoxyuridine-5'-[para-trifluorophenyl-(ethoxy-α,α-cycloleucinyl)]-phosphate (CPF 29)

$C_{26}H_{30}BrF_3N_3O_9P$, MW=696.40.

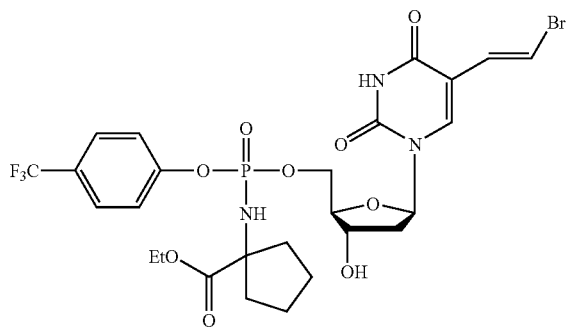

This was synthesised according to Standard procedure 5, using BVdU (150 mg, 0.45 mmol), para-trifluorophenyl-(ethoxy-α,α-cycloleucinyl)-phosphorochloridate (540 mg, 1.35 mmol), NMI (4.50 mmol, 300 μL) in THF (5 mL) for 2 hrs. The crude product was purified by column chromatography, eluting with $CH_2Cl_2$/Methanol 97:3 to give the pure product as a white foamy solid (185 mg, yield 59%).

$^{31}$P-NMR (CDCl$_3$, 121 MHz): δ 4.30.

$^{1}$H-NMR (CDCl$_3$, 300 MHz): δ 10.35 (1H, bs, H-3), 7.70 (1H, 2×s, H-6), 7.40 (1H, 2d, $^{3}$J=14 Hz, H-5b), 7.28-7.14 (2H, m, OPh), 7.05-6.95 (2H, m, OPh), 6.70 (1H, 2d, $^{3}$J=14 Hz, H-5a), 6.3 (1H, m, H1'), 4.55-4.3 (3H, m, H-5', H-3'), 4.2-4.1 (3H, m, H-4', CH$_3$CH$_2$O), 2.5-2.35 (1H, m, one of H-2'), 2.20-1.9 (5H, m, one of H-2'+4H cyclopentane), 1.85-1.6 (4H, m, 4H cyclopentane), 1.25 (3H, 2t, $^{3}$J=7 Hz, CH$_3$CH$_2$O).

$^{13}$C-NMR (CDCl$_3$, 75 MHz): δ 14.5 (CH$_3$CH$_2$O), 24.5, 24,4 (2CH$_2$ cyclopent), 39.3, 39.2, 38.9, 38.5 (2CH$_2$ cyclopent), 40.6 (C-2'), 62.2 (CH$_3$CH$_2$O), 66.7 (Cqcyclopentane), 67.4, 67.3 (C-5'), 70.9 (C-3'), 85.8, 85.7 (C-1', C-4'), 110.2 (C-5b), 111.9 (C-5), 116.8, 116.5 ('o', OPh), 122.2, 122.1 ('m', OPh), 125.1 (d, J=270 Hz, CF$_3$), 129.0 (C-5a), 131.1 ('p', q, J=32 Hz, OPh), 138.5 (C-6), 146.8, 146.7 ('ipso', OPh), 149.9 (C-4), 162.3 (C-2), 175.9, 175.8 (COOCH$_2$CH$_3$).

Synthesis of (E)-5-(2-Bromovinyl)-2'-deoxyuridine-5'-[para-trifluorophenyl-(benzoxy-α,α-cycloleucinyl)]-phosphate (CPF 30)

$C_{31}H_{32}BrF_3N_3O_9P$, MW=758.47.

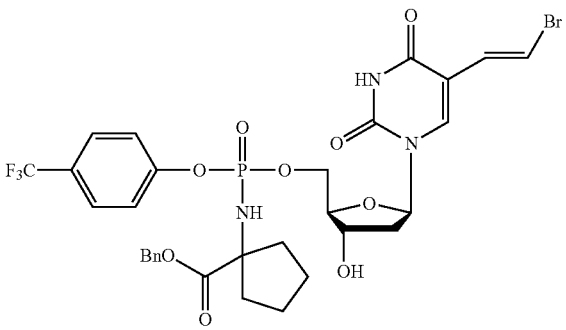

This was synthesised according to Standard procedure 5, using BVdU (150 mg, 0.45 mmol), para-trifluorophenyl-(benzyloxy-α,α-cycloleucinyl)-phosphorochloridate (623 mg, 1.35 mmol), NMI (4.5 mmol, 300 μL) in THF (5 mL) for 2 hrs. The crude product was purified by column chromatography, eluting with $CH_2Cl_2$/Methanol 97:3 to give the pure product as a white foamy solid (218 mg, yield 64%).

$^{31}$P-NMR (CDCl$_3$, 121 MHz): δ 4.30.

$^{1}$H-NMR (CDCl$_3$, 300 MHz): δ 10.35 (1H, bs, H-3), 7.65 (1H, 2×s, H-6), 7.55 (2H, m, 2H OPh), 7.45-7.25 (8H. m, 2H OPh+CH$_2$Ph+H-5b), 6.7 (1H, 2d, $^{3}$J=14 Hz, H-5a), 6.30 (1H, 2t,$^{3}$J=6 Hz, H-1), 5.15 (1H, 2s, CH$_2$Ph), 4.55-4.35 (3H, m, H-3'+H-5'), 4.25 (1H, H-4'), 4.10 (1H, NH), 2.55-2.35 (1H, m, one of H-2'), 2.30-1.92 (5H, m, one of H-2'+4H cyclopentane), 1.8-1.6 (4H, m, 4H cyclopentane).

$^{13}$C-NMR (CDCl$_3$, 75 MHz): δ 25.5, 24.4, 24,3, 24.2 (2CH$_2$ cyclopent), 39.2, 39.1, 38.7, 38.6 (2CH$_2$ cyclopent), 40.5, 40.0 (C-2'), 66.4 (Cq cyclopentane), 66.8 (C-5'), 68.0 (CH$_2$Ph), 70.9 (C-3'), 86.0, 85.8, 85.4, 85.3 (C-1', C-4'), 110.3 (C-5), 111.9 (C-5), 121.8, 120.8 ('o, m', OPh), 125.2 (d, J=270 Hz, CF$_3$), 128.5, 127.7, 127.5 (Bn, C-5a), 129,2 ('p',q, J=32 Hz, OPh), 135.4 ('ipso', CH$_2$Ph), 138.5 (C-6), 149.9 (C-4), 153.5 ('ipso' OPh), 162.2 (C-2), 175.6, 175.5 (COOBn).

Synthesis of (E)-5-(2-Bromovinyl)-2'-deoxyuridine-5'-[phenyl-(methoxy-L-phenylalaninyl)]-phosphate (CPF 36)

C$_{27}$H$_{29}$BrN$_3$O$_9$P, MW=650.41.

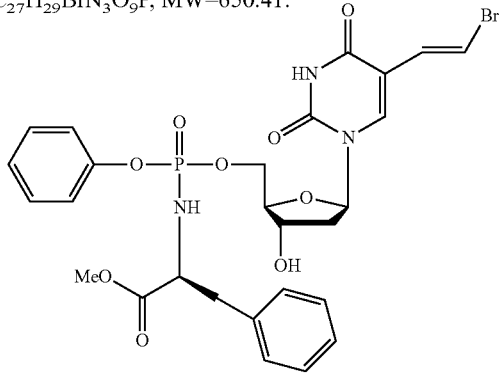

This was synthesised according to Standard procedure 5, using BVdU (150 mg, 0.45 mmol), Phenyl-(methoxy-L-phenylalaninyl)-phosphorochloridate (477 mg, 1.35 mmol), NMI (4.42 mmol, 190 µL) in THF (5 mL) for 2 hrs. The crude product was purified by column chromatography, eluting with CH$_2$Cl$_2$/Methanol 97:3 to give the pure product as a white foamy solid (169 mg, yield 58%).

$^{31}$P-NMR (CDCl$_3$, 121 MHz): δ 4.79, 4.71.

$^1$H-NMR (CDCl$_3$; 300 MHz): δ 9.95 (1H, bs, H-3), 7.60-7.55 (1H, 2×s, H-6), 7.48-7.4 (1H, 2d, $^3$J=14 Hz, H-5b), 7.3-7.1 (10H, m, CH$_2$Ph+OPh), 6.75-6.65 (1H, 2d, $^3$J=14 Hz, H-5a), 6.27-6.18 (1H, m, H1'), 4.57-4.29 (6H, m, H-5',H-3', H-4', NH, CHphenylala), 3.70 (3H, 2s, CH$_3$O), 3.01 (2H, m, CH$_2$Ph), 2.35-2.20 (1H, m, one of H-2'), 2.07-1.95 (1H, m, one of H-2').

$^{13}$C-NMR (CDCl$_3$; 75 MHz): δ 36.3 (CH$_2$phenylalanine), 41.9, 41.8 (C-2'), 53.0 (CH$_3$O), 56.6, 56.1 (CHphenylala), 67.1 (C-5'), 71.3, 70.7 (C-3'), 85.7, 85.6, 85.5, 85.4 (C-1', C-4'), 110.4 (C-5b), 111.9 (C-5), 120.6, 120.5 ('o', OPh), 127.8 ('p', OPh), 130.1, 129.9, 129.8, 129.1 (CH$_2$Ph, C-5a, 'm' OPh), 138.0, 137.9 (C-6), 149.8 (C-4), 150.7, 150.6 ('ipso', OPh), 162.1, 162.0 (C-2), 173.5 (COOCH$_3$).

Synthesis of (E)-5-(2-Bromovinyl)-2'-deoxyuridine-5'-[phenyl-(methoxy-L-leucinyl)]-phosphate (CPF 35)

C$_{24}$H$_{31}$BrN$_3$O$_9$P, MW=616.40.

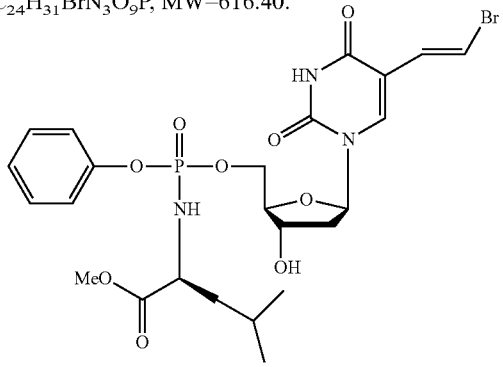

This was synthesised according to Standard procedure 5, using BVdU (150 mg, 0.45 mmol), Phenyl-(methoxy-L-leucinyl)-phosphorochloridate (432 mg, 1.35 mmol), NMI (4.42 mmol, 190 µL) in THF (5 mL) for 2 hrs. The crude product was purified by column chromatography, eluting with CH$_2$Cl$_2$/Methanol 97:3 to give the pure product as a white foamy solid (167 mg, yield 60%).

$^{31}$P-NMR (CDCl$_3$, 121 MHz): δ 5.14, 4.60.

$^1$H-NMR (CDCl$_3$; 300 MHz): δ 10.1 (1H, bs, H-3), 7.75 (1H, 2×s, H-6), 7.45 (1H, 2d, $^3$J=14 Hz, H-5b), 7.4-7.2 (5H, m, OPh), 6.85 (1H, 2d, $^3$J=14 Hz, H-5a), 6.27-6.18 (1H, 2t, $^3$J=6 Hz, H1'), 4.5-4.2 (4H, m, H-5',H-3', NH), 4.1 (1H, m,H-4'), 3.95 (1H, m, CHCH$_2$CH(CH$_3$)$_2$), 3.70 (3H, 2s, CH$_3$O), 2.40-2.20 (1H, m, one of H-2'), 2.05-1.95 (1H, m, one of H-2'), 1.8 (1 H, m, CHCH$_2$CH(CH$_3$)$_2$), 1.8-1.5 (2H, m, CHCH$_2$CH(CH$_3$)$_2$), 1.0-0.9 (6H, m, CHCH$_2$CH(CH$_3$)$_2$).

$^{13}$C-NMR (CDCl$_3$; 75 MHz): δ 23.2, 23.1, 22.0, 21.9 (2C, CHCH$_2$CH(CH$_3$)$_2$), 24.9, 24.7 (CHCH$_2$CH(CH$_3$)$_2$), 40.6 (C-2'), 43.7, 43.6 (CHCH$_2$CH(CH$_3$)$_2$), 53.0 (CH$_3$O), 53.7, 53.6 (CHCH$_2$CH(CH$_3$)$_2$), 66.6, 66.3 (C-5'), 71.1, 70.8 (C-3'), 86.0, 85.7, 85.6, 85.5 (C-1', C-4'), 110.4 (C-5b), 111.9 (C-5), 120.6, 120.5, 120.4 ('o', OPh), 125.8, 125.7 ('p', OPh), 128.9 (C-5a), 130.2 ('m' OPh), 138.1 (C-6), 149.9 (C-4), 150.8, 150.7 ('ipso', OPh), 162.2 (C-2), 175.1, 174.9 (COOCH$_3$).

Synthesis of (E)-5-(2-Bromovinyl)-2'-deoxyuridine-5'-[phenyl-(benzoxy-L-leucinyl)]-phosphate (CPF 37)

C$_{30}$H$_{35}$BrN$_3$OP, MW=692.49.

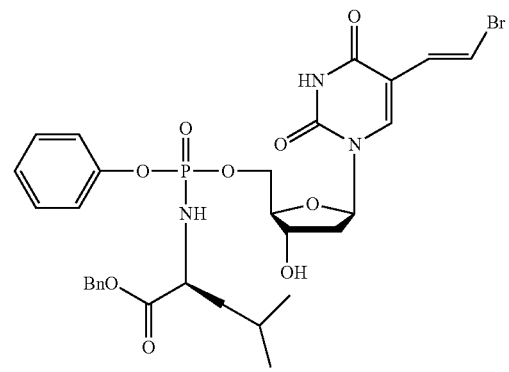

This was synthesised according to Standard procedure 5, using BVdU (150 mg, 0.45 mmol), Phenyl-(benzoxy-L-leucinyl)-phosphorochloridate (534 mg, 1.35 mmol), NMI (4.42 mmol, 190 µL) in THF (5 mL) for 2 hrs. The crude product was purified by column chromatography, eluting with CH$_2$Cl$_2$/Methanol 97:3 to give the pure product as a white foamy solid (199 mg, yield 64%).

$^{31}$P-NMR (CDCl$_3$, 121 MHz): δ 5.18, 4.54.

$^1$H-NMR (CDCl$_3$; 300 MHz): δ 9.95-9.85 (1H, bs, H-3), 7.55 (1H, 2×s, H-6), 7.38 (1H, 2d, $^3$J=14 Hz, H-5b), 7.3-7.1 (5H, m, CH$_2$Ph+OPh), 6.65 (1H, 2d, $^3$J=14 Hz, H-5a), 6.26-6.14 (1H, 2t, $^3$J=6 Hz, H1'), 5.1 (2H, 2s, CH$_2$Ph) 4.4-3.8 (6H, m, H-5',H-3, NH, H-4', CHCH$_2$CH(CH$_3$)$_2$), 2.35-2.25 (1H, m, one of H-2'), 1.95-1.85 (1H, m, one of H-2'), 1.6-1.4 (3H, m, CHCH$_2$CH(CH$_3$)$_2$), 0.8 (6H, m, CHCH$_2$CH(CH$_3$)$_2$).

$^{13}$C-NMR (CDCl$_3$; 75 MHz): δ 23.2, 23.1, 22.0, 21.9 (2C, CHCH$_2$CH(CH$_3$)$_2$), 24.9, 24.7 (CHCH$_2$CH(CH$_3$)$_2$), 40.7 (C-2'), 43.9, 43.8 (CHCH$_2$CH(CH$_3$)$_2$), 53.9, 53.7 (CHCH$_2$CH(CH$_3$)$_2$), 66.4, 66.2 (C-5'), 67.8, 67.7 (CH$_2$Ph), 71.1, 70.7 (C-3'), 85.9, 85.6, 85.4, 85.3 (C-1', C-4'), 110.4 (C-5b), 111.9 (C-5), 120.6, 120.5 ('o', OPh), 125.8, 125.7 ('p', OPh), 130.2, 129.1, 128.9 (C-5a, CH$_2$Ph, 'm' OPh), 135.4 ('ipso', CH$_2$Ph), 138.1 (C-6),149.8 (C4),150.2 ('ipso', OPh), 162.1 (C-2),175.7, 174.6 (COOBn).

Synthesis of (E)-5-(2-Bromovinyl)-2'-deoxyuridine-5'-(para-nitrophenyl-(benzoxy-L-leucinyl)]-phosphate (CPF 38)

$C_{30}H_{34}BrN_4O_{11}P$, MW=737.49.

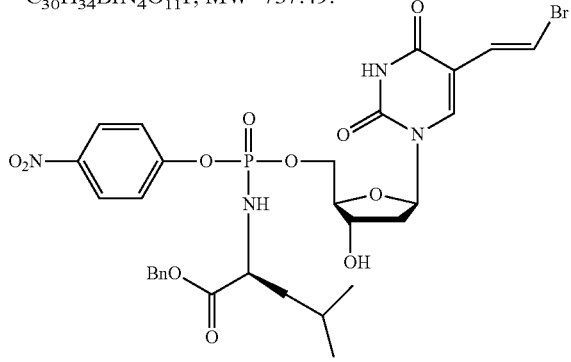

This was synthesised according to Standard procedure 5, using BVdU (150 mg, 0.45 mmol), para-nitrophenyl-(benzoxy-L-leucinyl)-phosphorochloridate (595 mg, 1.35 mmol), NMI (4.42 mmol, 190 µL) in THF (5 mL) for 2 hrs. The crude product was purified by column chromatography, eluting with $CH_2Cl_2$/Methanol 97:3 to give the pure product as a white foamy solid (176 mg, yield 53%).

$^{31}$P-NMR (CDCl$_3$, 121 MHz): δ 5.72, 4.35.

$^1$H-NMR (CDCl$_3$; 300 MHz): δ 10.2 (1H, bs, H-3), 8.1(2H, m, 2H OPh), 7.65 (1H, 2×s, H-6), 7.45-7.2 (8H, m, H-5b, CH$_2$Ph+2H OPh), 6.65 (1H, 2d, $^3$J=14 Hz, H-5a), 6.35-6.2 (1H, 2t, $^3$J=6 Hz, H1'), 5.15 (2H, 2s, CH$_2$Ph) 4.7-3.9 (6H, m, H-5',H-3', NH, H-4', CHCH$_2$CH(CH$_3$)$_2$), 2.55-2.4 (1H, m, one of H-2'), 2.15-2.05 (1H, m, one of H-2'), 1.7-1.5 (3H, m, CHCH$_2$CH(CH$_3$)$_2$), 0.95-0.8 (6H, m, CHCH$_2$CH(CH$_3$)$_2$).

$^{13}$C-NMR (CDCl$_3$; 75 MHz): δ 23.2, 23.1, 22.0, 21.9 (2C, CHCH$_2$CH(CH$_3$)$_2$), 24.9, 24.8 (CHCH$_2$CH(CH$_3$)$_2$), 40.6 (C-2'), 43.7, 43.6 (CHCH$_2$CH(CH$_3$)$_2$), 53.9, 53.7 (CHCH$_2$CH(CH$_3$)$_2$), 66.9 (C-5'), 67.9 (CH$_2$Ph), 71.2, 70.8 (C-3'), 85.8, 85.3, 85.2 (C-1', C-4'), 110.6 (C-5b), 111.9 (C-5), 121.3 ('o' OPh), 129.2, 129.1, 128.8, 126.2 (C-5a, CH$_2$Ph, 'm' OPh), 135.4, 135.3 ('ipso', CH$_2$Ph), 138.2 (C-6), 145.2, 145.1 ('ipso', OPh), 149.9 (C-4), 155.5 ('p', OPh), 162.1 (C-2), 174.2 (COOBn).

Synthesis of (E)-5-(2-Bromovinyl)-2'-deoxyuridine-5'-[para-chlorophenyl-(benzoxy-L-leucinyl)]-phosphate (CPF 39)

$C_{30}H_{34}BrClN_3O_9P$, MW=726.94.

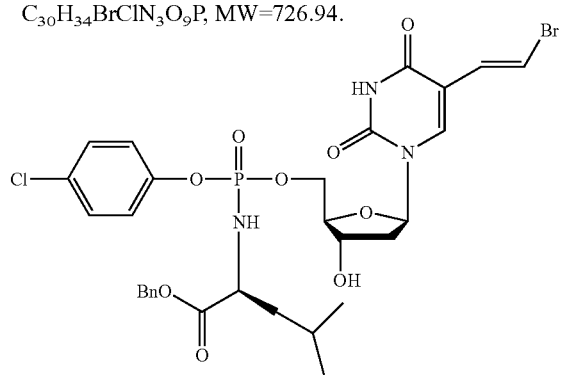

This was synthesised according to Standard procedure 5, using BVdU (150 mg, 0.45 mmol), para-chlorophenyl-(benzoxy-L-leucinyl)-phosphorochloridate (581 mg, 1.35 mmol), NMI (4.42 mmol, 190 µL) in THF (5 mL) for 2 hrs. The crude product was purified by column chromatography, eluting with $CH_2Cl_2$/Methanol 97:3 to give the pure product as a white foamy solid (221 mg, yield 68%).

$^{31}$P-NMR (CDCl$_3$, 121 MHz): δ 5.27, 4.76.

$^1$H-NMR (CDCl$_3$; 300 MHz): δ 10.25-10.15 (1H, bs, H-3), 7.65 (1H, 2×s, H-6), 7.45 (1H, 2d, $^3$J=14 Hz, H-5b), 7.4-7.15 (9H, m, CH$_2$Ph+OPh), 6.7 (1H, 2d, $^3$J=14 Hz, H-5a), 6.35-6.2 (1H, 2t, $^3$J=6 Hz, H1'), 5.15 (2H, 2s, CH$_2$Ph) 4.55-3.9 (6H, m, H-5', H-3', NH, H-4', CHCH$_2$CH(CH$_3$)$_2$), 2.5-2.4 (1H, m, one of H-2'), 2.15-2.0 (1H, m, one of H-2'), 1.7-1.45 (3H, m, CHCH$_2$CH(CH$_3$)$_2$), 0.94-0.82 (6H, m, CHCH$_2$CH(CH$_3$)$_2$).

$^{13}$C-NMR (CDCl$_3$; 75 MHz): δ 23.1, 23.0, 22.2, 22.0 (2C, CHCH$_2$CH(CH$_3$)$_2$), 24.9, 24.7 (CHCH$_2$CH(CH$_3$)$_2$), 40.7 (C-2'), 43.9, 43.8 (CHCH$_2$CH(CH$_3$)$_2$), 53.9, 53.7 (CHCH$_2$CH(CH$_3$)$_2$), 66.7, 66.3 (C-5'), 67.8 (CH$_2$Ph), 71.1, 70.7 (C-3'), 85.8, 85.7, 85.4 (C-1', C-4'), 110.5 (C-5b), 111.9 (C-5),122.1, 122.0 ('o', OPh), 130.2, 129.1, 129.0 (C-5a, CH$_2$Ph, 'm' OPh), 131.1, 130.9 ('p', OPh), 135.5, 135.4 ('ipso', CH$_2$Ph), 138.2 (C-6), 149.2, 149.1 ('ipso', OPh), 149.2, 149.1 (C-4),162.2 (C-2), 174.2, 174.2 (COOBn).

Synthesis of Gemcitabine-[phenyl-(benzoxy-L-alaninyl)]-phosphate $C_{25}H_{27}F_2N_4O_8P$, MW=580.47 (CPF 31).

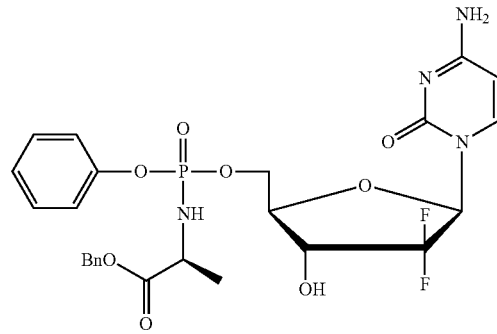

This was synthesised according to Standard procedure 5, using gemcitabine (131 mg, 0.5 mmol), Phenyl-(benzoxy-L-alaninyl)-phosphorochloridate (529 mg, 1.5 mmol), NMI (4.42 mmol, 300 µL) in THF/pyridine (4/2 mL) for 2 hrs. The crude product was purified by column chromatography, eluting with $CH_2Cl_2$/Methanol 95:5 to give the pure product as a white foamy solid (46 mg, yield 16%).

$^{31}$P-NMR (MeOD, 121 MHz): δ 5.05, 4.94.

$^1$H-NMR (MeOD, 300 MHz): δ 7.6-7.5 (1H, 2d, $^3$J=7 Hz H-6), 7.4-7.2 (10H, m, OPh+CH$_2$Ph), 6.25 (1H, m, H-1'), 5.95 (1H, 2d, $^3$J=7 Hz, H-5), 5.19 (1H, 2s, CH$_2$Ph), 4.55-4.1 (3H, m, H-3', H-4', CHala), 4.05 (2H, m, H-5'), 1.20 (3H, 2t, $^3$J=6 Hz, CH$_3$ala).

$^{13}$C-NMR (MeOD, 75 MHz): δ 20.8, 20.7 (CH$_3$ala), 52.2, 52.0 (CHala), 66.1 (C-5'), 68.4 (CH$_2$Ph), 71.9, 71.3 (C-3'), 80.6 (C-4'), 85.9 (C-1'), 97.1 (C-5), 121.8, 121.6 ('o', OPh), 123 (C-2'), 126.2 ('p', OPh), 131.8, 130.0, 129.7 ('m' OPh, Bn), 137.9('ipso', CH$_2$Ph), 142.7, 142.6 (C-6), 152.5, 152.4 ('ipso', OPh), 158.2 (C-2), 168.0 (C-4), 175.3, 174.9 (COOBn).

Synthesis of Gemcitabine-[para-chlorophenyl-(benzoxy-L-alaninyl)]-phosphate $C_{25}H_{26}ClF_2N_4O_8P$, MW=614.92 (CPF 40).

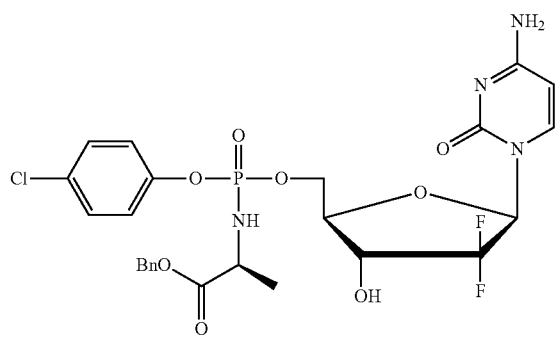

This was synthesised according to Standard procedure 5, using gemcitabine (131 mg, 0.5 mmol), para-chlorophenyl-(benzoxy-L-alaninyl)-phosphorochloridate (582 mg, 1.5 mmol), NMI (4.42 mmol, 300 μL) in THF/pyridine (4/2 mL) for 2 hrs. The crude product was purified by column chromatography, eluting with $CH_2Cl_2$/Methanol 95:5 to give the pure product as a white foamy solid (76 mg, yield 25%).

$^{31}$P-NMR (MeOD, 121 MHz): δ 5.08.

$^1$H-NMR (MeOD, 300 MHz): δ 7.65 (1H, 2d, $^3$J=7 Hz H-6), 7.5-7.2 (9H. m, OPh+CH$_2$Ph), 6.2 (1H, m, H-1'), 5.9 (1H, 2d, $^3$J=7 Hz, H-5), 5.12 (1H, 2s, CH$_2$Ph), 4.6-4.1 (3H, m, H-3', H-4', CHala), 4.05 (2H, m, H-5'), 1.45-1.35 (3H, 2t, $^3$J=6 Hz, CH$_3$ala).

$^{13}$C-NMR (MeOD, 75 MHz): δ 20.9, 20.7 (CH$_3$ala), 52.2, 52.0 (CHala), 66.2, 66.2 (C-5'), 68.5 (CH$_2$Ph), 71.5 (C-3'), 80.7 (C-4'), 86.4 (C-1'), 97.2 (C-5), 123.5 ('o', OPh), 126.9 (C-2'), 131.2, 130.6, 130.3 ('m' OPh, Bn), 131.9 ('p', OPh) 137.5 ('ipso', CH$_2$Ph), 142.8, 142.7 (C-6), 151.4, 151.0 ('ipso', OPh), 158.2 (C-2),166.9 (C-4), 175.1, 174.9 (COOBn).

Synthesis of Gemcitabine-[para-chlorophenyl-(benzoxy-α,α-dimethylglycinyl)]-phosphate (CPF 41)

$C_{26}H_{28}ClF_2N_4O_8P$, MW=628.95.

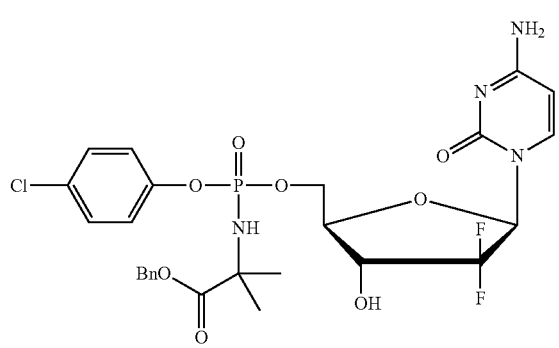

This was synthesised according to Standard procedure 5, using gemcitabine (131 mg, 0.5 mmol), para-chlorophenyl-(benzoxy-α,α-dimethylglycinyl)-phosphorochloridate (603 mg, 1.5 mmol), NMI (4.42 mmol, 300 μL) in THF/pyridine (4/3 mL) for 2 hrs. The crude product was purified by column chromatography, eluting with $CH_2Cl_2$/Methanol 95:5 to give the pure product as a white foamy solid (163 mg, yield 52%).

$^{31}$P-NMR (MeOD, 121 MHz): δ 3.56, 3.52.

$^1$H-NMR (MeOD, 300 MHz): δ 7.55 (1H, 2d, $^3$J=7 Hz, H-6), 7.4-7.15 (9H. m, OPh+CH$_2$Ph), 6.25 (1H, m, H-1'), 5.85 (1H, 2d, $^3$J=7 Hz, H-5), 5.15 (1H, 2s, CH$_3$Ph), 4.55-4.1 (3H, m, H-3', H-4'), 4.05 (2H, m, H-5'), 1.50 (6H, m, $^3$J=6 Hz, 2CH$_3$dimethygly).

$^{13}$C-NMR (MeOD, 75 MHz): δ 28.2, 28.0 (CH$_3$ dimethygly), 58.6 (Cq dimethygly), 66.2, 66.1 (C-5'), 66.7 (CH$_2$Ph), 71.5 (C-3'), 80.6 (C-4'), 86.4 (C-1'), 97.0 (C-5), 123.9, 123.6 ('o', OPh), 127.3 (C-2'), 130.0, 129.7 ('m' OPh, Bn), 131.8 ('p', OPh), 137.6 ('ipso', CH$_2$Ph), 142.8, 142.7 (C-6), 151.2, 151.1 ('ipso', OPh), 158.1 (C-2), 167.9 (C-4), 176.8, 176.7 (COOBn).

Synthesis of Phenyl-(methoxy-L-alaninyl)-phosphorochloridate $C_{10}H_{13}ClNO_4P$, MW=277.64.

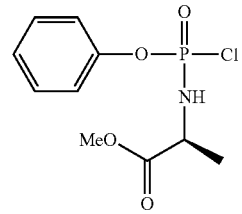

This is synthesised according to Standard procedure 4, using L-alanine methyl ester hydrochloride (2 g, 14.3 mmol), phenyldichlorophosphate (3.02 g, 2.14 ml, 14.3 mmol), and TEA (2.9 g, 4.0 ml, 28.7 mmol) in DCM (60 mL), to yield 3.91 g (98%) of crude product used without further purification.

$^{31}$P-NMR (CDCl$_3$, 121 MHz): δ 9.28, 8.97.

$^1$H-NMR (CDCl$_3$; 300 MHz): δ 7.39-7.34 (2H, m, 'o' OPh), 7.29-7.20 (2H, m 'm+p' OPh), 4.98 (1H, bs, NH), 4.27-4.09 (1H, m, CHala), 3.78 (3H, s, OCH$_3$), 1.52-1.49 (3H, 2×d, $^3$J=7 Hz, CH$_3$ala).

$^{13}$C-NMR (CDCl$_3$; 75 MHz): δ 20.9 (CH$_3$ala), 51.0 (CHala), 53.6 (OCH$_3$), 120.9 ('o'OPh), 126.4 ('p', OPh), 130.2 ('m', OPh), 150.1 ('ipso', OPh), 173.6(COOCH$_3$).

Synthesis of Phenyl-(ethoxy-L-alaninyl)-phosphorochloridate $C_{11}H_{15}ClNO_4P$, MW-291.67.

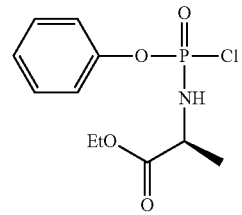

This is synthesised according to Standard procedure 4, using L-alanine ethyl ester hydrochloride (770 mg, 5.01 mmol), phenyldichlorophosphate (1.12 g, 5.01 mmol, 749 μL), and TEA (1.4 mL, 10.02 mmol) in DCM (40 mL). The crude was purified by flash chromatography (ethyl acetate/petroleum ether 7:3) affording 1.02 (69%) of oil.

$^{31}$P-NMR (CDCl$_3$, 121 MHz): δ 9.49, 9.07.

$^1$H-NMR (CDCl$_3$; 300 MHz): δ 7.39-7.34 (2H, m, 'o' OPh), 7.29-7.20 (2H, m, 'm+p' OPh), 4.95 (1H, bs, NH, 4.3-4.1 (3H, m, OCH$_2$CH$_3$, CHala), 1.50 (3H, 2×d, $^3$J=7 Hz, CH$_3$ala), 1.30 (3H, t, $^3$J=7.1 Hz, OCH$_2$CH$_3$).

$^{13}$C-NMR (CDCl$_3$; 75 MHz): δ 14.5 (CH$_3$CH$_2$), 20.9 (CH$_3$ala), 51.0 (CHala), 62.6 CH$_3$CH$_2$), 120.9 ('o' OPh), 126.5 ('p', OPh), 130.1 ('m', OPh), 150.1 ('ipso', OPh), 175.1 (COOCH$_2$CH$_3$).

Synthesis of
Phenyl-(benzoxy-L-alaninyl)-phosphorochloridate

C$_{16}$H$_{17}$ClNO$_4$P, MW=353.74.

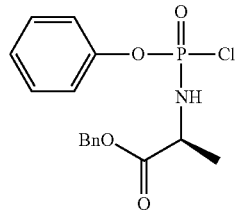

This is synthesised according to Standard procedure 4, using L-alanine benzyl ester hydrochloride (1.0 g, 4.64 mmol), phenyl-dichlorophosphate (980 mg, 0.69 ml, 4.64 mmol), and TEA (0.94 g, 1290 μL, 9.27 mmol) in DCM (40 mL). The crude was purified by flash chromatography (ethyl acetate/petroleum ether 6:4) affording 1.61 (98%) of oil.

$^{31}$P-NMR (CDCl$_3$, 121 MHz): δ 9.41, 9.23.

$^1$H-NMR (CDCl$_3$; 300 MHz): δ 7.41-7.21 (10H, m, OPh+CH$_2$Ph), 5.24 (2H, s, CH$_2$Ph), 4.95-4.88 (1H, bs, NH), 4.36-4.15 (1H, m, CHala), 1.52-1.49 (3H, 2×d, $^3$J=7 Hz, CH$_3$ala).

$^{13}$C-NMR (CDCl$_3$; 75 MHz): δ 20.8 (CH$_3$ala), 51.1 (CHala), 68.0 (CH$_2$Ph), 121.0 ('o' OPh), 126.4 ('p', OPh), 130.3, 129,0, 128.7 ('m'OPh, CH$_2$Ph), 135.5 ('ipso', CH$_2$Ph), 150.2 ('ipso', OPh), 172.9 (COOCH$_2$Ph).

Synthesis of p-nitrophenyl-(methoxy-L-alaninyl)-phosphorochloridate

C$_{10}$H$_{12}$ClN$_2$O$_6$P, MW=322.64.

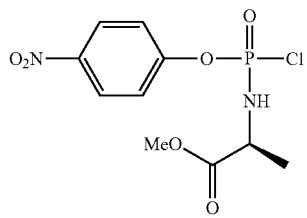

This is synthesised according to Standard procedure 4, using L-alanine methyl ester hydrochloride (0.70 g, 5.01 mmol), p-nitrophenyldichlorophosphate (1.362 g, 5.01 mmol), and TEA (1.4 ml, 10 mmol) in DCM (40 mL), to yield 1.60 g (99%) of crude product used without further purification.

$^{31}$P-NMR (CDCl$_3$, 121 MHz): δ 9.13, 9.03.

$^1$H-NMR (CDCl$_3$; 300 MHz): δ 8.1 (2H, 2d, $^3$J=8 Hz, OPh), 7.3 (2H, 2d, $^3$J=8 Hz, OPh), 5.0 (1H, bs, NH), 4.1 (1H, m, CHala), 3.75 (3H, s, OCH$_3$), 1.5-1.45 (3H, m, CH$_3$ala).

$^{13}$C-NMR (CDCl$_3$; 75 MHz): δ 20.8, 20.7 (CH$_3$ala), 51.1, 50.9 (CHala), 53.2, 53.2 (OCH$_3$), 121.8, 121.6 ('o' OPh), 126.5 ('m', OPh), 145.7 ('ipso', OPh), 154.7, 154.6 ('p', OPh), 173.4, 173.2 (COOCH$_3$).

Synthesis of p-nitrophenyl-(ethoxy-L-alaninyl)-phosphorochloridate

C$_{11}$H$_{14}$ClN$_2$O$_6$P, MW=336.67.

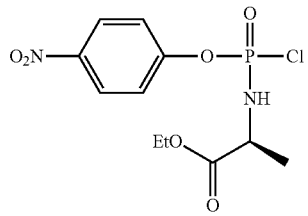

This is synthesised according to Standard procedure 4, using L-alanine ethyl ester hydrochloride (770 mg, 5.01 mmol), p-nitrophenyldichlorophosphate (1.362 g, 5.01 mmol), and TEA (1.4 mL, 10.02 mmol) in DCM (40 mL), to yield 1.64 g (98%) of crude product used without further purification.

$^{31}$P-NMR(CDCl$_3$, 121 MHz): δ 9.06, 8.81.

$^1$H-NMR (CDCl$_3$; 300 MHz): δ & 8.1 (2H, m, OPh), 7.4 (2H, m, OPh), 4.9-4.7 (1H, bs, NH), 4.3-4.1 (3H, m, OCH$_2$CH$_3$, CHala), 1.55-1.45 (3H, 2×d, $^3$J=7 Hz, CH$_3$ala), 1.40 (3H, t, $^3$J=7 Hz, OCH$_2$CH$_3$).

$^{13}$C-NMR (CDCl$_3$; 75 MHz): δ 14.5 (CH$_3$CH$_2$), 21.1, 20.9 (CH$_3$ala), 51.2, 51.0 (CHala), 62.6 CH$_3$CH$_2$), 121.7, 121.3 ('o' OPh), 126.2, 126.0 ('m', OPh), 145.7 ('ipso', OPh), 154.5 ('p', OPh), 173.4, 173.3 (COOCH$_2$CH$_3$).

Synthesis of p-nitrophenyl-(benzoxy-L-alaninyl)-phosphorochloridate

C$_{16}$H$_{16}$ClN$_2$O$_6$P, MW=398.04.

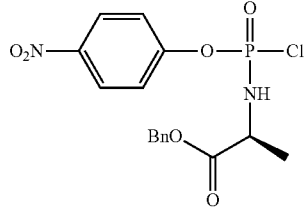

This is synthesised according to Standard procedure 4, using L-alanine benzyl ester hydrochloride (1.08 g, 5.01 mmol), para-nitrophenyl-dichloro phosphate (1.362 g, 5.01 mmol), and TEA (1.4 mL, 1.4 mmol) in DCM (40 mL), to yield 1.85 g (93%) of crude product used without further purification.

$^{31}$P-NMR (CDCl$_3$, 121 MHz): δ 9.15, 9.06.

$^1$H-NMR (CDCl$_3$; 300 MHz): δ 8.15 (2H, m, OPh), 7.45 (2H,m, OPh), 7.35-7.25 (5H, m, CH$_2$Ph), 5.2 (2H, 2s, CH$_2$Ph), 5.00 (1H, bs, NH) 4.2 (1H, m, CHala), 1.64 (3H, 2×d, J=7 Hz, CH$_3$ala).

$^{13}$C-NMR (CDCl$_3$; 75 MHz): δ 20.8 (CH$_3$ala), 51.1 (CHala), 68.0 (CH$_2$Ph), 121.4 ('o' OPh), 126.1 ('m'OPh), 130.3, 129.0 (CH$_2$Ph), 145.7 ('ipso', CH$_2$Ph), 150.2 ('ipso', OPh), 154.6 ('p', OPh), 172.9 (COOCH$_2$Ph).

Synthesis of p-fluorophenyl-(methoxy-L-alaninyl)-phosphorochloridate

C$_{10}$H$_{12}$ClFNO$_4$P, MW=295.63.

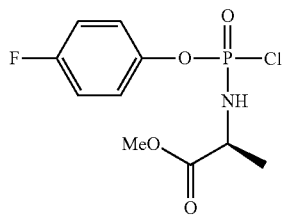

This is synthesised according to Standard procedure 4, using L-alanine methyl ester hydrochloride (0.70 g, 5.01 mmol), p-fluorophenyldichlorophosphate (1.210 g, 5.01 mmol), and TEA (1.4 ml, 10 mmol) in DCM (40 mL). The crude was purified by flash chromatography (ethyl acetate/petroleum ether 7:3) affording 1.11 g (75%) of oil.

$^{31}$P-NMR (CDCl$_3$, 121 MHz): δ 9.98, 9.96.

$^1$H-NMR (CDCl$_3$; 300 MHz): δ 7.1 (2H, m, OPh), 6.95 (2H, m, OPh), 5.0 (1H, bs, NH), 4.25-4.1 (1H, m, CHala), 3.78 (3H, 2s, OCH$_3$), 1.55 (3H, m, CH$_3$ala).

$^{13}$C-NMR (CDCl$_3$; 75 MHz): δ 20.8 (CH$_3$ala), 51.1, 50.9 (CHala), 53.3 (OCH$_3$), 117.1, 117.0 ('o' OPh), 122.6, 122.5 ('m', OPh), 146.0 ('ipso', OPh), 159.1, 159.0 ('p', OPh), 173.4, 173.2 (COOCH$_3$).

Synthesis of p-fluorophenyl-(ethoxy-L-alaninyl)-phosphorochloridate

C$_{11}$H$_{14}$ClFNO$_4$P, MW=309.66.

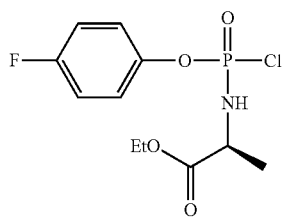

This is synthesised according to Standard procedure 4, using L-alanine ethyl ester hydrochloride (770 mg, 5.01 mmol), p-fluorophenyldichlorophosphate (1.210 g, 5.01 mmol), and TEA (1.4 mL, 10.02 mmol) in DCM (40 mL). The crude was purified by flash chromatography (ethyl acetate/petroleum ether 7:3) affording 1.07 (69%) of oil.

$^{31}$P-NMR (CDCl$_3$, 121 MHz): δ 10.04, 9.95.

$^1$H-NMR (CDCl$_3$; 300 MHz): δ 7.1 (2H, m, OPh), 6.95 (2H, m, OPh), 5.0 (1H, bs, NH), 4.25-4.1 (3H, m, OCH$_2$CH$_3$, CHala), 1.55 (3H, m, CH$_3$ala), 1.40 (3H, t, $^3$J=7 Hz, OCH$_2$CH$_3$).

$^{13}$C-NMR (CDCl$_3$; 75 MHz): δ 14.5 (CH$_3$CH$_2$), 21.1, 21.0 (CH$_3$ala), 51.2, 51.1 (CHala), 62.6 (CH$_3$CH$_2$), 117.3 ('o'OPh), 122.2, 122.0 ('m', OPh), 145.9, 145.8 ('ipso', OPh), 159.0 ('p', OPh), 173.6, 173.5 (COOCH$_2$CH$_3$).

Synthesis of p-fluorophenyl-(benzoxy-L-alaninyl)-phosphorochloridate

C$_{16}$H$_{16}$ClFNO$_4$P, MW=371.73.

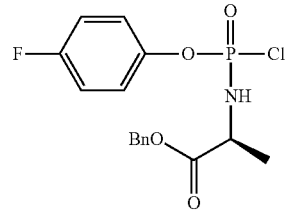

This is synthesised according to Standard procedure 4, using L-alanine benzyl ester hydrochloride (1.08 g, 5.01 mmol), para-fluorophenyl-dichloro phosphate (1.210 mg, 5.01 mmol), and TEA (1.4 mL, 1.4 mmol) in DCM (40 mL). The crude was purified by flash chromatography (ethyl acetate/petroleum ether 7:3) affording 1.599 (86%) of oil.

$^{31}$P-NMR (CDCl$_3$, 121 MHz): δ 9.15, 9.06.

$^1$H-NMR (CDCl$_3$; 300 MHz): δ 7.35-7.25 (5H, m, CH$_2$Ph), 7.1 (2H, m, OPh), 6.95 (2H, m, OPh), 5.2 (2H, 2s, CH$_2$Ph), 5.00 (1H, bs, NH), 4.25-4.1 (1H, m, CHala), 1.55 (3H, m, CH$_3$ala).

$^{13}$C-NMR (CDCl$_3$; 75 MHz): δ 20.8 (CH$_3$ala), 51.1, 51.0 (CHala), 68.1 (CH$_2$Ph), 117.0, 116.9 ('o' OPh), 122.6 ('m'OPh), 130.3, 129.0 (CH$_2$Ph), 135.7 ('ipso', CH$_2$Ph), 146.1, 146.0('ipso', OPh), 158.9 ('p', OPh), 173.1 (COOCH$_2$Ph).

Synthesis of 4-(trifluoromethyl)-phenyl-(methoxy-L-alaninyl)-phosphorochloridate C$_{11}$H$_{12}$ClF$_3$NO$_4$P, MW=345.64.

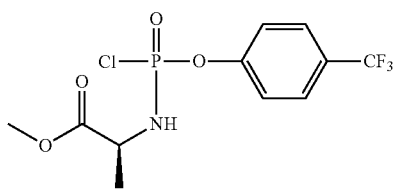

This is synthesised according to Standard procedure 4, using L-alanine methyl ester hydrochloride (1.0 g, 7.16 mmol), 4-(trifluoromethyl)-phenyl-phosphodichloridate (1.998 g, 7.16 mmol), and TEA (1.449 g, 14.32 mmol, 1916 µL) in DCM (30 mL), to yield 2.202 g (89.0%) of crude product used without further purification.

$^{31}$P-NMR (CDCl$_3$, 121 MHz): δ 9.36, 9.22.

$^1$H-NMR (CDCl$_3$; 300 MHz): δ 7.66 (2H, d, $^3$J=8.1 Hz, OPh), 7.44-7.33 (2H, m, OPh), 5.10 (1H, bs, NH), 3.81-3.78 (3H, 2s, CH$_3$O), 3.77-3.68 (1H, m, CH$_3$CH), 1.56-1.52 (3H, m, CHCH$_3$).

$^{13}$C-NMR (CDCl$_3$; 75 MHz): δ 20.6, 20.7 (CH$_3$CH), 50.9, 51.1 (CHCH$_3$), 53.2 (CH$_3$O), 121.4 ('o', OPh), 124.1 (CF$_3$, J=270 Hz), 128.0 ('m', OPh), 128.6 ('p', J=34 Hz), 152.4, 152.6 ('ipso', OPh), 173.4, 173.5 (COOCH$_3$).

Synthesis of 4-(trifluoromethyl)-phenyl-(ethoxy-L-alaninyl)-phosphorochloridate C$_{12}$H$_{14}$ClF$_3$NO$_4$, MW=359.67.

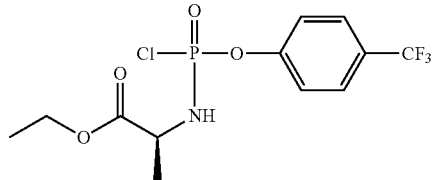

This is synthesised according to Standard procedure 4, using L-alanine ethyl ester hydrochloride (1.0 g, 6.50 mmol), 4-(trifluoromethyl)-phenyl-phosphodichloridate (1.813 g, 6.50 mmol), and TEA (1.316 g, 13.00 mmol, 1740 µL) in DCM (30 mL), to yield 2.150 g (92.2%) of crude product used without further purification.

$^{31}$P-NMR (CDCl$_3$, 121 MHz): δ 9.33, 9.28.

$^1$H-NMR (CDCl$_3$; 300 MHz): δ 7.70 (2H, d, $^3$J=8.2 Hz, OPh), 7.46-7.39 (2H, m, OPh), 4.78 (1H, bs, NH), 4.33-4.17 (3H, m, CH$_3$CH$_2$O+CHCH$_3$), 1.59-1.55 (1H, m, CHCH$_3$), 1.56-1.52 (3H, m, CH$_2$CH$_3$).

$^{13}$C-NMR (CDCl$_3$; 75 MHz): δ 14.5 (CH$_3$CH$_2$O), 20.8, 20.9 (CH$_3$CH), 50.3, 50.9 (CHCH$_3$), 62.3, 62.5 (CH$_3$CH$_2$O), 121.4 ('o', OPh), 124.1 (CF$_3$, J=270 Hz), 127.7 ('m', OPh), 128.7 ('p', J=33 Hz), 152.4 ('ipso', OPh), 172.9 (COOCH$_2$CH$_3$).

Synthesis of p-trifluorophenyl-(benzoxy-L-alaninyl)-phosphorochloridate

C$_{17}$H$_{16}$ClF$_3$NO$_4$P, MW=421.73.

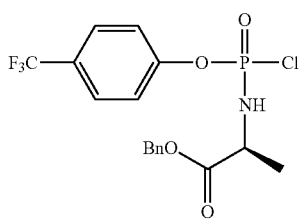

This is synthesised according to Standard procedure 4, using L-alanine benzyl ester hydrochloride (1.08 g, 5.01 mmol), para-trifluorophenyl-dichloro phosphate (1.490 mg, 5.01 mmol), and TEA (1.4 mL, 1.4 mmol) in DCM (40 mL). The crude was purified by flash chromatography (ethyl acetate/petroleum ether 6:4) affording 1.80 (85%) of oil.

$^{31}$P-NMR (CDCl$_3$, 121 MHz): δ 9.11, 8.84.

$^1$-NMR (CDCl$_3$; 300 MHz): δ 7.65 (2H, m, OPh), 7.4-7.2 (7H, m, CH$_2$Ph+2H OPh), 5.25 (2H, 2s, CH$_2$Ph), 4.75-4.55 (1H, bs, NH), 4.25-4.1 (1H, m, CHala), 1.60-1.55 (3H, 2d, $^3$J=7 Hz, CH$_3$ala).

$^{13}$C-NMR (CDCl$_3$; 75 MHz): δ 20.9 (CH$_3$ala), 51.3, 51.0 (CHala), 68.2, 68.1 (CH$_2$Ph), 121.4, 120.9 ('o', OPh), 125.2 (d, J=270 Hz, CF$_3$), 126.6 ('m', OPh), 129.1, 128.8, 127.8 (Bn), 130.0 ('p',q, J=32 Hz, OPh), 135.4 ('ipso', CH$_2$Ph), 153.0 ('ipso', OPh), 172.8 (COOCH$_2$Ph).

Synthesis of 4-chlorophenyl-(methoxy-L-alaninyl)-phosphorochloridate

C$_{10}$H$_{12}$Cl$_2$NO$_4$P, MW=312.09.

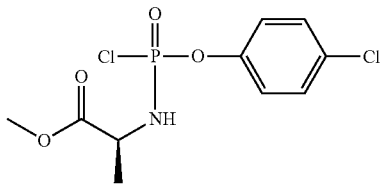

This is synthesised according to Standard procedure 4, using L-alanine methyl ester hydrochloride (1.0 g, 7.16 mmol), 4-chlorophenylphosphorodichloridate (1.757 g, 7.16 mmol), and TEA (1.449 g, 14.32 mmol, 1995 µL) in DCM (30 mL), to yield 1.621 g (72.5%) of crude product used without further purification.

$^{31}$P-NMR (CDCl$_3$, 121 MHz): δ 9.36, 9.07.

$^1$H-NMR (CDCl$_3$; 300 MHz): δ 7.35-7.15 (4H, m, OPh), 4.48-4.36 (1H, bs, NH), 4.22-4.04 (1H, m, CHCH$_3$), 3.76-3.74 (3H, 2s, CH$_3$O), 1.49-1.46 (3H, m, CHCH$_3$.

$^{13}$C-NMR (CDCl$_3$; 75 MHz): δ 21.0 (CH$_3$CH), 50.8, 51.1 (CHCH$_3$), 53.4 (CH$_3$O), 121.9, 122.1, 122.3, 122.4 ('o', OPh), 130.6, 130.4, 130.2 ('m', OPh), 132.0 ('p', OPh), 148.6 ('ipso', OPh), 173.5 (COOCH$_3$).

Synthesis of 4-chlorophenyl-(ethoxy-L-alaninyl)-phosphorochloridate

C$_{11}$H$_{14}$Cl$_2$NO$_4$P, MW=326.11.

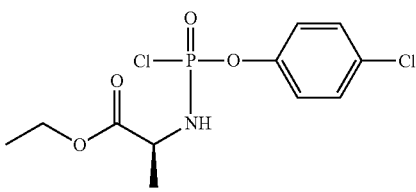

This is synthesised according to Standard procedure 4, using L-alanine ethyl ester hydrochloride (1.000 g, 6.50 mmol), 4-chlorophenylphosphorodichloridate (1.595 g, 6.50 mmol), and TEA (1.315 g, 13.00 mmol, 1810 µL) in DCM (20 mL), to yield 1.794 mg (yield 84.7%) of product.

$^{31}$P-NMR (CDCl$_3$, 121 MHz): δ 9.54, 9.25.

$^1$H-NMR (CDCl$_3$; 300 MHz): δ 7.44-7.21 (4H, m, OPh), 4.59 (1H, bs, NH), 4.33-4.13 (3H, m, OCH$_2$CH$_3$+CHCH$_3$), 1.57-1.56 (3H, m, CH$_3$CH), 1.43-1.21 (3H, m, OCH$_2$CH$_3$).

$^{13}$C-NMR (CDCl$_3$; 75 MHz): δ 14.5, 14.6 (OCH$_2$CH$_3$), 21.0, 21.5 (CH$_3$CH), 50.9, 51.2 (CHCH$_3$), 62.4, 62.5 (OCH$_2$CH$_3$), 122.04, 122.3, 122.4 ('o', OPh), 130.4 ('m', OPh), 131.9 ('p', OPh), 148.5, 148.6 ('ipso', OPh), 173.0, 173.1 (COOCH$_2$CH$_3$).

Synthesis of 4-nitrophenyl-(benzyl-2-amino-2-methylpropanoate)-phosphorochloridate $C_{16}H_{16}Cl_2NO_4P$, MW=388.18.

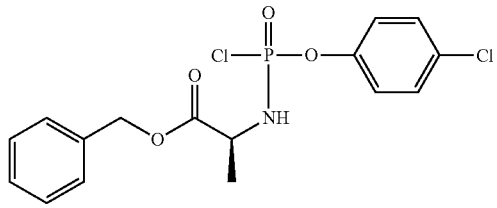

This is synthesised according to Standard procedure 4, using L-alanine benzyl ester hydrochloride (1.000 g, 4.63 mmol), 4-chlorophenylphosphodichloride (1.136 g, 4.63 mmol), and TEA (937.0 mg, 9.26 mmol, 1290 μL) in DCM (40 mL), to yield 1534 mg (yield 86.5%) of crude product used without further purification.

$^{31}$P-NMR (CDCl$_3$, 121 MHz): δ 9.43, 9.16.

$^{1}$H-NMR (CDCl$_3$; 300 MHz): δ 7.42-7.08 (9H, m, O Ph+CH$_2$Ph), 5.19 (2H, s, CH$_2$Ph), 4.61-4.54 (1H, bs, NH), 4.26-4.10 (1H, m, CHCH$_3$), 1.42-1.38 (3H, m, CH$_3$CH).

$^{13}$C-NMR (CDCl$_3$; 75 MHz): δ 20.9, 21.0 (CH$_3$CH), 51.0, 51.2 (CHCH$_3$), 68.1, 68.2 (OCH$_2$Ph), 122.3, 122.4 ('o', O Ph), 128.8, 129.1, 130.4 ('o', 'm', 'p', CH$_2$Ph+OPh), 131.9 ('ipso', CH$_2$Ph), 135.3 ('p', OPh), 148.5 ('ipso', OPh), 172.7, 172.8 (COOCH$_2$Ph).

Synthesis of phenyl-(methyl-2-amino-2-methylpropanoate)-phosphorochloridate $C_{11}H_{15}ClNO_4P$, MW=291.67.

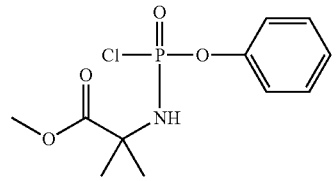

This is synthesised according to Standard procedure 4, using 2-aminoisobutyrate methyl ester hydrochloride (583.5 mg, 3.75 mmol), phenyl dichlorophosphate (791.1 mg, 3.75, 560 μL), and TEA (758.9 mg, 7.5 mmol, 1045 μL) in DCM (20 mL), to yield 1.041 g (95.2%) of crude product used without further purification.

$^{31}$P-NMR (CDCl$_3$, 121 MHz): δ 6.99 (s).

$^{1}$H-NMR (CDCl$_3$; 300 MHz): δ 7.41-7.17 (5H, m, OPh), 4.98 (1H, bs, NH), 3.80 (3H, s, OCH$_3$), 1.71-1.69 (6H, 2s, [CH$_3$]$_2$C).

$^{13}$C-NMR (CDCl$_3$; 75 MHz): δ 27.3, 27.2, 27.0 ([CH$_3$]$_2$C), 53.6 (OCH$_3$), 58.8 (C[CH$_3$]$_2$), 120.0, 121.1 ('o' OPh), 126.2 ('p', OPh), 130.3 ('m', OPh) 145.7 ('p', OPh), 150.2, 150.3 ('ipso', OPh), 175.6, 175.7 (COOCH$_3$).

Synthesis of phenyl-(ethyl-2-amino2-methylpropanoate)-phosphorochloridate $C_{12}H_{17}ClNO_4P$, MW=305.69.

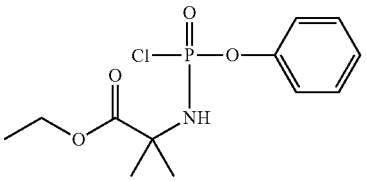

This is synthesised according to Standard procedure 4, using 2-aminoisobutyrate ethyl ester hydrochloride (628.6 mg, 3.75 mmol), phenyl dichlorophosphate (791.1 mg, 3.75, 560 μL), and TEA (758.9 mg, 7.5 mmol, 1045 μL) in DCM (20 mL), to yield 1.018 g (88.8%) of crude product used without further purification.

$^{31}$P-NMR (CDCl$_3$, 121 MHz): δ 7.02 (s)

$^{1}$H-NMR (CDCl$_3$; 300 MHz): δ 7.23-7.37 (5H, m, OPh), 4.98 (1H, bs, NH), 4.24 (2H, q, $^3$J=7.1 Hz, OCH$_2$CH$_3$), 1.70, 1.68 (6H, 2s, [CH$_3$]$_2$C), 1.30 (3H, t, $^3$J=7.1 Hz, OCH$_2$CH$_3$).

$^{13}$C-NMR (CDCl$_3$; 75 MHz): δ 14.5 (CH$_3$CH$_2$O), 27.3, 26.9 ([CH$_3$]$_2$C), 58.7 (C[CH$_3$]$_2$), 62.7 (OCH$_2$CH$_3$), 121.1, 121.0 ('o', OPh), 127.6 ('p', OPh), 130.7 ('m', OPh), 150.4 ('ipso', OPh), 175.2, 175.1 (COOCH$_2$CH$_3$).

Synthesis of phenyl-(benzyl-2-amino-2-methylpropanoate)-phosphorochloridate $C_{17}H_{19}ClNO_4P$, MWV=367.76.

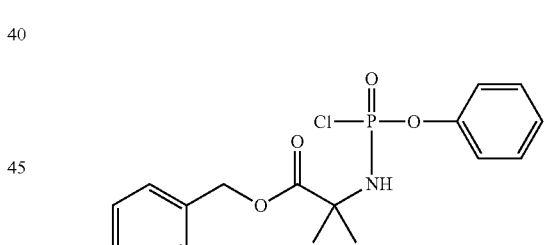

This is synthesised according to Standard procedure 4, using 2-aminoisobutyrate benzyl ester hydrochloride (861.4 mg, 3.75 mmol), phenyl dichlorophosphate (791.1 mg, 3.75, 560 μL), and TEA (758.9 mg, 7.5 mmol, 1045 μL) in DCM (30 mL). The crude was purified by flash chromatography (ethyl acetate/petroleum ether 6:4) affording 580 mg (42.2%) of oil.

$^{31}$P-NMR (CDCl$_3$, 121 MHz): δ 6.79 (s)

$^{1}$H-NMR (CDCl$_3$; 300 MHz): δ 7.45-7.27 (10H, m, O Ph+CH$_2$Ph), 5.28 (2H, s, CH$_2$Ph), 4.81, 4.78 (1H, 2bs, NH), 1.78, 1.75 (6H, 2s, [CH$_3$]C).

$^{13}$C-NMR (CDCl$_3$; 75 MHz): δ 27.3, 26.9 ([CH$_3$]C), 53.9 (C[CH$_3$]$_2$), 60.9 (CH$_2$Ph), 121.0, 126.3, 128.6, 129.0, 129.1, 130.3, 135.5 (OPh, CH$_2$Ph), 135.5 ('ipso', CH$_2$Ph), 150.3, 150.2 ('ipso', OPh), 175.0, 175.2 (COOCH$_2$Ph).

Synthesis of 4-nitrophenyl-(methyl-2-amino-2-methylpropanoate)-phosphorochloridate C$_{11}$H$_{14}$ClN$_2$O$_6$P, MW=336.67.

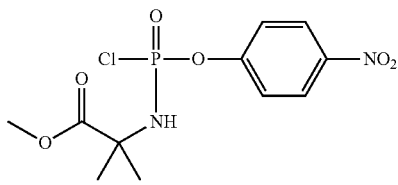

This is synthesised according to Standard procedure 4, using 2-aminoisobutyrate methyl ester hydrochloride (290.0 mg, 1.89 mmol), 4-nitrophenylphosphodichloride (483.3 mg, 1.89 mmol), and TEA (382.5 mg, 3.78 mmol, 526.9 μL) in DCM (15 mL), to yield 486 mg (yield 76.4%) of crude product used without further purification.

$^{31}$P-NMR (CDCl$_3$, 121 MHz): δ 6.61 (s)

$^1$H-NMR (CDCl$_3$; 300 MHz): δ 8.25 (2H, d, $^3$J=9.0 Hz, OPh), 7.43 (2H, d, $^3$J=9.0 Hz, OPh), 4.91-4.87 (1H, 2bs, NH), 3.79 (3H, s, OCH$_3$), 1.69-1.66 (6H, 2s, [CH$_3$]$_2$C).

$^{13}$C-NMR (CDCl$_3$; 75 MHz): δ 27.0, 27.1, 27.3 ([CH$_3$]$_2$C), 53.8 (OCH$_3$), 59.2 (C[CH$_3$]$_2$), 121.7, 121.8 ('o' OPh), 126.2 ('m', OPh), 145.7 ('p', OPh), 154.8, 154.7 ('ipso', OPh), 175.4, 175.6 (COOCH$_3$).

Synthesis of 4-nitrophenyl-(ethyl-2-amino-2-methylpropanoate)-phosphorochloridate C$_{12}$H$_{16}$ClN$_2$O$_6$P, MW=350.69.

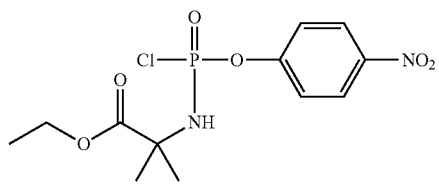

This is synthesised according to Standard procedure 4, using 2-aminoisobutyrate ethyl ester hydrochloride (270.0 mg, 1.61 mmol), 4-nitrophenylphodichloride (412.3 mg, 1.61 mmol), and TEA (325.8 mg, 3.22 mmol, 448.8 μL) in DCM (15 mL), to yield 500 mg (yield 88.5%) of crude product used without further purification.

$^{31}$P-NMR (CDCl$_3$, 121 MHz): δ 6.64 (s)

$^1$H-NMR (CDCl$_3$; 300 MHz): δ 8.35 (2H, d, $^3$J=9.0 Hz, OPh), 7.53 (2H, d, $^3$J=9.0 Hz, OPh), 4.99-4.96 (1H, 2bs, NH), 4.34 (2H, q, $^3$J=7.1 Hz, OCH$_2$CH$_3$), 1.79-1.76 (6H, 2s, [CH$_3$]$_2$C), 1.40 (3H, t, $^3$J=7.1 Hz, OCH$_2$CH$_3$.

$^{13}$C-NMR (CDCl$_3$; 75 MHz): δ 14.5 (OCH$_2$CH$_3$), 27.0, 27.3 ([CH$_3$]$_2$C), 59.1, 59.2 (C[CH$_3$]$_2$), 62.9, 63.0 (OCH$_2$CH$_3$), 121.7, 121.8 ('o' OPh, 126.2 ('m', OPh), 145.7 ('p', OPh), 154.7, 154.8 ('ipso' OPh), 175.4, 175.6 (CCOOCH$_2$CH$_3$).

Synthesis of 4-nitrophenyl-(benzyl-2-amino-2-methylpropanoate)-phosphorochloridate C$_{17}$H$_{18}$ClN$_2$O$_6$P, MW=412.76.

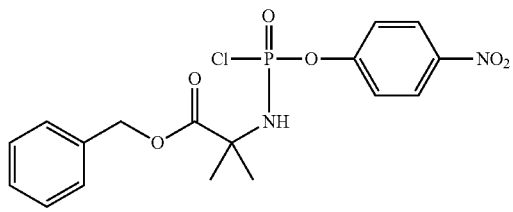

This is synthesised according to Standard procedure 4, using 2-aminoisobutyrate benzyl ester hydrochloride (578 mg, 2.52 mmol), 4-nitrophenylphosphodichloride (645 mg, 2.52 mmol), and TEA (510 mg, 5.04 mmol, 702.5 μL) in DCM (20 mL), to yield 936 mg (yield 90.0%) of crude product used without further purification.

$^{31}$P-NMR (CDCl$_3$, 121 MHz): δ 6.56 (s)

$^1$H-NMR (CDCl$_3$; 300 MHz): δ 8.29 (2H, d, $^3$J=9.0 Hz, OPh), 7.47 (2H, d, $^3$J=9.0 Hz, OPh), 7.40-7.37 (5H, m, CH$_2$Ph), 5.27 (2H, s, CH$_2$Ph), 5.04-5.01 (1H, 2bs, NH), 1.77-1.74 (6H, 2s, [CH$_3$]$_2$C).

$^{13}$C-NMR (CDCl$_3$; 75 MHz): δ 27.0, 27.3, ([CH$_3$]$_2$C), 59.2 (C[CH$_3$]$_2$), 68.5 (OCH$_2$Ph), 121.6, 121.7, 126.2, 128.6, 129.1, ('o', 'm', 'p', CH$_2$Ph+OPh), 135.7 ('ipso', CH$_2$Ph), 145.7 ('p', OPh), 154.7, 154.8 ('ipso', OPh), 175.8, 175.9 (COOCH$_2$Ph).

Synthesis of 4-chlorophenyl-(methyl-2-amino-2-methylpropanoate)-phosphorochloridate C$_{11}$H$_{14}$Cl$_2$NO$_4$P, MW=326.11.

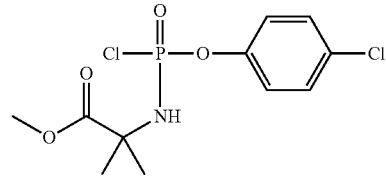

This is synthesised according to Standard procedure 4, using 2-aminoisobutyrate methyl ester hydrochloride (280.0 mg, 1.82 mmol), 4-chlorophenylphosphodichloride (447.4 mg, 1.82 mmol), and TEA (368.3 mg, 3.64 mmol, 507.3 μL) in DCM (20 mL), to yield 554 mg (yield 91.1%) of crude product used without further purification.

$^{31}$P-NMR (CDCl$_3$, 121 MHz): δ 7.05 (s)

$^1$H-NMR (CDCl$_3$; 300 MHz): δ 7.38 (2H, d, $^3$J=9.0 Hz, OPh), 7.28-7.24 (2H, 2d, $^3$J=9.0 Hz, OPh), 4.87-4.83 (1H, 2bs, NH), 3.84 (3H, s, OCH$_3$), 1.73-1.71 (6H, 2s, [CH$_3$]$_2$C).

$^{13}$C-NMR (CDCl$_3$; 75 MHz): δ 27.0, 27.3, ([CH$_3$]$_2$C), 53.7 (OCH$_3$), 58.9 (C[CH$_3$]$_2$), 122.5 ('o', OPh), 129.7 ('m', OPh), 131.8 ('p', OPh) 148.7, 148.9 ('ipso', OPh), 175.5, 175.7 (COOCH$_3$).

Synthesis of 4-chlorophenyl-(ethyl-2-amino-2-methylpropanoate)-phosphorochloridate $C_{12}H_{16}Cl_2NO_4P$, MW=340.14.

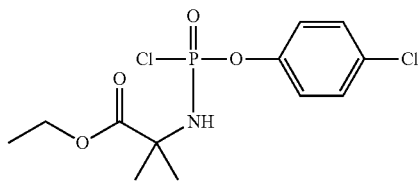

This is synthesised according to Standard procedure 4, using 2-aminoisobutyrate ethyl ester hydrochloride (293.4 mg, 1.75 mmol), 4-chlorophenylphosphodichloride (430.0 mg, 1.75 mmol), and TEA (354.2 mg, 3.50 mmol, 488.0 µL) in DCM (15 mL), to yield 571.7 mg (yield 96.1%) of crude product used without further purification.

$^{31}$P-NMR (CDCl$_3$, 121 MHz): δ 7.09 (s)

$^{1}$H-NMR (CDCl$_3$; 300 MHz): δ 7.38 (2H, d, $^3$J=9.1 Hz, OPh), 7.26 (2H, d, $^3$J=9.1 Hz, OPh), 4.88-4.84 (1H, 2bs, NH), 4.29 (2H, q, $^3$J=7.1 Hz, OCH$_2$CH$_3$), 1.74-1.70 (6H, 2s, [CH$_3$]C), 1.35 (3H, t, $^3$J=7.1 Hz, OCH$_2$CH$_3$).

$^{13}$C-NMR (CDCl$_3$; 75 MHz): δ 14.5 (OCH$_2$CH$_3$), 27.0, 27.3 ([CH$_3$]$_2$C), 58.9 (C[CH$_3$]$_2$), 62.8 (OCH$_2$CH$_3$), 122.5 ('o', OPh), 130.4 ('m', OPh), 131.8 ('p', OPh), 148.7, 148.8 ('ipso', OPh), 175.1, 175.3 (COOCH$_2$CH$_3$).

Synthesis of 4-chlorophenyl-(benzyl-2-amino-2-methylpropanoate)-phosphorochloridate $C_{17}H_{18}Cl_2NO_4P$, MW=402.21.

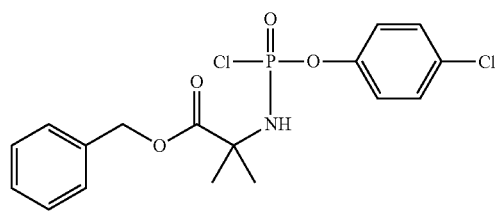

This is synthesised according to Standard procedure 4, using 2-aminoisobutyrate benzyl ester hydrochloride (402.0 mg, 1.75 mmol), 4-chlorophenylphosphodichloride (430 mg, 1.75 mmol), and TEA (354.2 mg, 3.50 mmol, 488.0 µL) in DCM (15 mL), to yield 657.9 mg (yield 93.5%) of crude product used without further purification.

$^{31}$P-NMR (CDCl$_3$, 121 MHz): δ 7.00 (s)

$^{1}$H-NMR (CDCl$_3$; 300 MHz): δ 7.39-7.12 (9H, m, CH$_2$Ph+OPh), 5.18 (2H, s, CH$_2$Ph), 4.75-4.72 (1H, 2bs, NH), 1.68-1.65 (6H, 2s, [CH$_3$]$_2$C).

$^{13}$C-NMR (CDCl$_3$; 75 MHz): δ 27.0, 27.3, ([CH$_3$]$_2$C), 59.0 (C[CH$_3$]$_2$), 68.4 (OCH$_2$Ph), 122.5, 128.6, 129.1, 130.7 ('o', 'm', 'p', CH$_2$Ph+OPh), 131.8 ('p', CH$_2$Ph), 135.4 ('p', OPh), 148.6, 148.7 ('ipso', OPh), 174.9, 175.1 (COOCH$_2$Ph).

Synthesis of 4-(trifluoromethyl)-phenyl-(benzyl-2-amino-2-methylpropanoate)-phosphorochloridate $C_{18}H_{18}ClF_3NO_4P$, MW=435.76.

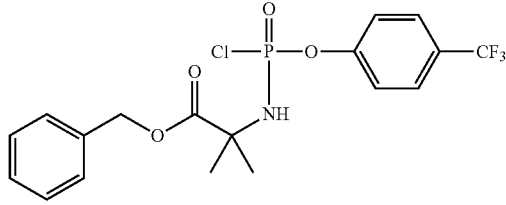

This is synthesised according to Standard procedure 4, using 2-aminoisobutyrate benzyl ester hydrochloride (341.0 mg, 1.49 mmol), 4-(trifluoromethyl)-phenyl-phosphodichloridate (414.3 mg, 1.49 mmol), and TEA (300.5 mg, 2.97 mmol, 413.9 µL) in DCM (15 mL), to yield 623.9 mg (96.4%) of crude product used without further purification.

$^{13}$P-NMR (CDCl$_3$, 121 MHz): δ 6.74 (s)

$^{1}$H-NMR (CDCl$_3$; 300 MHz): δ 7.66 (2H, d, $^3$J=8.8 Hz, OPh), 7.42-7.30 (7H, m, OPh+CH$_2$Ph), 5.25 (2H, s, CH$_2$Ph), 4.95-4.91 (1H, 2bs, NH), 1.75-1.72 (6H, 2s, (CH$_3$)$_2$C).

$^{13}$C-NMR (CDCl$_3$; 75 MHz): δ 26.9, 27.0, 27.3 ([CH$_3$]$_2$C), 59.1 (C[CH$_3$]$_2$), 68.4 (CH$_2$Ph), 121.1, 121.4, 127.7, 128.4, 128.5, 128.6, 128.9 ('o', 'm', 'p', OPh+CH$_2$Ph), 124.2 (CF$_3$, J=265 Hz), 135.4 ('ipso', CH$_2$Ph), 152.6, 152.7 ('ipso', OPh), 174.9, 175.0 (COOCH$_2$Ph).

Synthesis of Phenyl-(methoxy-α,α-cycloleucinyl)-phosphorochloridate $C_{13}H_{17}ClNO_4P$, MW=317.70.

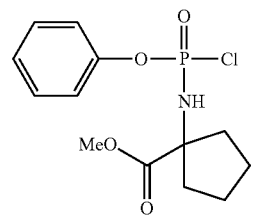

This is synthesised according to Standard procedure 4, using methyl-1-amino-1-cyclopentanoate hydrochloride salt (0.885 g, 5.01 mmol), phenyldichlorophosphate (1.12 g, 0.749 ml, 5.01 mmol), and TEA (1.4 ml, 10 mmol) in DCM (40 mL), to yield 1.266 g (81%) of crude product used without further purification.

$^{31}$P-NMR (CDCl$_3$, 121 MHz): δ 7.90.

$^{1}$H-NMR (CDCl$_3$; 300 MHz): δ 7.4-7.2 (5H, m, OPh), 4.3 (1H, bs, NH), 3.75 (3H, 2s, OCH$_3$), 2.15 (4H, m, 4H cyclopentane), 1.9-1.7 (4H, m, 4H cyclopentane).

$^{13}$C-NMR (CDCl$_3$; 75 MHz): δ 24.4 (2CH$_2$ cyclopent), 38.8, 38.7, 38.6 (2CH$_2$ cyclopent), 53.3, 53.2 (CH$_3$O), 66.6 (Cq cyclopentane), 121.1, 121.0 ('o' OPh), 126.3 ('p', OPh), 130.3, 130.2 ('m', OPh), 150.2 ('ipso', OPh), 174.8 (COOCH$_3$).

Synthesis of Phenyl-(ethoxy-α,α-cycloleucinyl)-phosphorochloridate

C$_{14}$H$_{19}$ClNO$_4$P, MW=331.73.

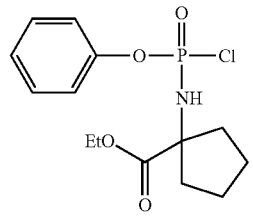

This is synthesised according to Standard procedure 4, using ethyl-1-amino-1-cyclopentanoate hydrochloride salt (955 mg, 5.01 mmol), phenyldichlorophosphate (1.12 g, 5.01 mmol, 749 µL), and TEA (1.4 mL, 10.02 mmol) in DCM (40 mL). The crude was purified by flash chromatography (ethyl acetate/petroleum ether 7:3) affording 1.457 g (89%) of oil.

$^{31}$P-NMR (CDCl$_3$, 121 MHz): δ 8.04, 7.97.

$^1$H-NMR (CDCl$_3$; 300 MHz): δ 7.4-7.1 (5H, m, OPh), 4.7 (1H, bs, NH), 4.2 (2H, 2q, $^3$J=7.1 Hz, OCH$_2$CH$_3$), 2.15 (4H, m, 4H cyclopentane), 1.9-1.7 (4H, m, 4H cyclopentane), 1.30 (3H, t, $^3$J=7.1 Hz, OCH$_2$CH$_3$).

$^{13}$C-NMR (CDCl$_3$; 75 MHz): δ 14.5 (CH$_3$CH$_2$), 24.5 (2CH$_2$ cyclopent), 38.8, 38.7, 38.6, 38.5 (2CH$_2$ cyclopent), 62.0 CH$_3$CH$_2$), 68.3 (Cq cyclopentane), 120.9 ('o' OPh), 126.3 ('p', OPh), 130.3 ('m', OPh), 150.3-150.2 ('ipso', OPh), 174.9-174.8 (COOCH$_2$CH$_3$).

Synthesis of Phenyl-(benzoxy-α,α-cycloleucinyl)-phosphorochloridate

C$_{19}$H$_{21}$ClNO$_4$P, MW=393.80.

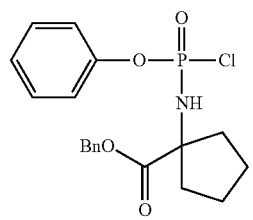

This is synthesised according to Standard procedure 4, using benzyl-1-amino-1-cyclopentanoate hydrochloride salt (0.984 g, 3.84 mmol), phenyl-dichlorophosphate (0.577 ml, 3.84 mmol), and TEA (1.08 mL, 7.69 mmol) in DCM (30 mL), to yield 1.485 g (98%) of crude product used without further purification.

$^{31}$P-NMR (CDCl$_3$, 121 MHz): δ 7.85.

$^1$H-NMR (CDCl$_3$; 300 MHz): δ 7.3-7.0 (10H, m, OPh+CH$_2$Ph), 5.2 (2H, s, CH$_2$Ph), 4.95-4.65 (1H, bs, NH), 2.25-2.1 (4H, m, 4H cyclopentane), 1.9-1.7 (4H, m, 4H cyclopentane).

$^{13}$C-NMR (CDCl$_3$; 75 MHz): δ 24.4, 24.3 (2CH$_2$ cyclopent), 38.8, 38.7, 38.5 (2CH$_2$ cyclopent), 67.3 (Cq cyclopentane), 68.0 (CH$_2$Ph), 121.0 ('o' OPh), 126.4 ('p', OPh), 130.1, 129.0, 128.8 ('m' OPh, CH$_2$Ph), 135.4 ('ipso', CH$_2$Ph), 150.1 ('ipso', OPh), 173.4 (COOCH$_2$Ph),

Synthesis of p-fluorophenyl-(methoxy-α,α-cycloleucinyl)-phosphorochloridate

C$_{13}$H$_{16}$ClNO$_4$P, MW=335.70.

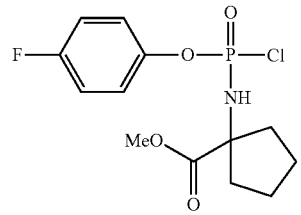

This is synthesised according to Standard procedure 4, using methyl-1-amino-1-cyclopentanoate hydrochloride salt (0.885 g, 5.01 mmol), parafluorophenyldichlorophosphate (1.21 g, 5.01 mmol), and TEA (1.4 ml, 10 mmol) in DCM (40 mL), to yield 1.65 g (99%) of crude product used without further purification.

$^{31}$P-NMR (CDCl$_3$, 121 MHz): δ 8.61.

$^1$H-NMR (CDCl$_3$; 300 MHz): δ 7.3-7.2 (2H, m, OPh), 7.1-7.0 (2H, m, OPh), 4.7 (1H, bs, NH), 3.78 (3H, 2s, OCH$_3$), 2.25-2.15 (4H, m, 4H cyclopentane), 2.0-1.8 (4H, m, 4H, m, 4H cyclopentane).

$^{13}$C-NMR (CDCl$_3$; 75 MHz): δ 24.4 (2CH$_2$ cyclopent), 38.7, 38.6, 38.5 (2CH$_2$ cyclopent), 53.3 (CH$_3$O), 66.3-66.2 (Cq cyclopentane), 117.1-116.8 ('o' OPh), 122.6-122.5 ('m', OPh), 146.1-145.9 ('ipso', OPh), 159.0 ('p', OPh), 175.3-175.2 (COOCH$_3$).

Synthesis of p-fluorophenyl-(ethoxy-α,α-cycloleucinyl)-phosphorochloridate

C$_{14}$H$_{18}$ClFNO$_4$P, MW=349.72.

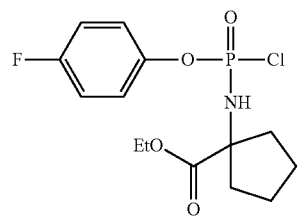

This is synthesised according to Standard procedure 4, using ethyl-1-amino-1-cyclopentanoate hydrochloride salt (955 mg, 5.01 mmol), para-fluorophenyldichlorophosphate (1.21 g, 5.01 mmol), and TEA (1.4 mL, 10.02 mmol) in DCM (40 mL), to yield 1.64 g (94%) of crude product used without further purification.

$^{31}$P-NMR (CDCl$_3$, 121 MHz): δ 8.70.

$^1$H-NMR (CDCl$_3$; 300 MHz): δ 7.3-7.2 (2H, m, OPh), 7.1-7.0 (2H, m, OPh), 4.8 (1H, bs, NH), 4.2 (2H, 2q,$^3$J=7.1 Hz, OCH$_2$CH$_3$), 2.25-2.1 (4H, m, 4H cyclopentane), 2.0-1.8 (4H, m, 4H cyclopentane), 1.4 (3H, t, $^3$J=7.1 Hz, OCH$_2$CH$_3$).

$^{13}$C-NMR (CDCl$_3$; 75 MHz): δ 14.4 (CH$_3$CH$_2$), 24.4 (2CH$_2$ cyclopent), 38.8, 38.7, 38.6, 38.5 (2CH$_2$ cyclopent), 62.3 CH$_3$CH$_2$), 68.3 (Cq cyclopentane), 117.4, 117.0 ('o' OPh), 122.7, 122.6 ('m', OPh), 146.1, 146.0 ('ipso', OPh), 159.0 ('p', OPh), 174.9 (COOCH$_2$CH$_3$).

Synthesis of p-fluorophenyl-(benzoxy-α,α-cyclo-leucinyl)-phosphorochloridate $C_{19}H_{20}ClFNO_4P$, MW=411.79.

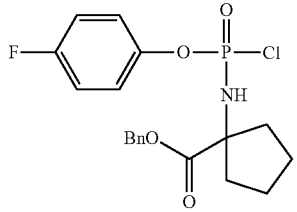

This is synthesised according to Standard procedure 4, using benzyl-1-amino-1-cyclopentanoate hydrochloride salt (1.281 g, 5.01 mmol), para-fluorophenyl-dichlorophosphate (1.21 g, 5.01 mmol), and TEA (1.4 mL, 10 mmol) in DCM (40 mL), to yield 1.85 g (90%) of crude product used without further purification.

$^{31}$P-NMR (CDCl$_3$, 121 MHz): δ 7.85.

$^1$H-NMR (CDCl$_3$; 300 MHz): δ 7.65-7.4 (5H, m, CH$_2$Ph), 7.3-7.2 (2H, m, OPh), 7.1-7.0 (2H, m, OPh), 5.2 (2H, s, CH$_2$Ph), 4.6 (1H, bs, NH), 2.2-2.1 (4H, m, 4H cyclopentane), 2.0-1.8 (4H, m, 4H cyclopentane).

$^{13}$C-NMR (CDCl$_3$; 75 MHz): δ 24.5 (2CH$_2$ cyclopent), 38.9, 38.8, 38.6, 38.5 (2CH$_2$ cyclopent), 68.1 (Cq cyclopentane), 68.4 (CH$_2$Ph), 117.0, 116.8 ('o' OPh), 122.6, 122.5 ('m' OPh) 129.1, 129.0, 128.8, 128.7 (CH$_2$Ph), 135.7 ('ipso', CH$_2$Ph), 146.1, 145.9 ('ipso', OPh), 159.0 ('p', OPh), 174.6 (COOCH$_2$Ph).

Synthesis of p-nitrophenyl-(methoxy-α,α-cyclo-leucinyl)-phosphorochloridate $C_{13}H_{16}ClN_2O_6P$, MW=362.70.

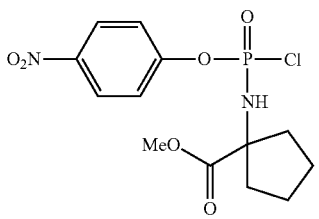

This is synthesised according to Standard procedure 4, using methyl-1-amino-1-cyclopentanoate hydrochloride salt (0.885 g, 5.01 mmol), para-nitrophenyldichlorophosphate (1.632 g, 5.01 mmol), and TEA (1.4 ml, 10 mmol) in DCM (40 mL), to yield 1.601 g (90%) of crude product used without further purification.

$^{31}$P-NMR (CDCl$_3$, 121 MHz): δ 8.02.

$^1$H-NMR (CDCl$_3$; 300 MHz): δ 8.2 (2H, 2d, $^3$J=8 Hz, O Ph), 7.32 (2H, 2d, $^3$J=8 Hz OPh), 4.9 (1H, bs, NH), 3.71 (3H, s, OCH$_3$), 2.25-2.00 (4H, m, 4H cyclopentane), 1.95-1.7 (4H, m, 4H cyclopentane).

$^{13}$C-NMR (CDCl$_3$; 75 MHz): δ 24.3 (2CH$_2$ cyclopent), 38.7, 38.6 (2CH$_2$ cyclopent), 53.3 (CH$_3$O), 68.6 (Cq cyclopentane), 121.8, 121.7 ('o' OPh), 126.0 ('m', OPh), 145.6 ('ipso', OPh), 154.8, 154.7 ('p', OPh), 175.1-175.0 (COOCH$_3$).

Synthesis of p-nitrophenyl-(ethoxy-α,α-cycloleuci-nyl)-phosphorochloridate $C_{14}H_{18}ClN_2O_6P$, MW=376.73.

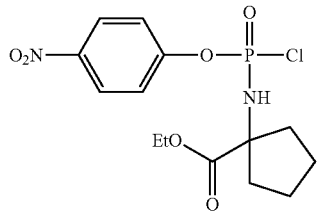

This is synthesised according to Standard procedure 4, using ethyl-1-amino-1-cyclopentanoate hydrochloride salt (955 mg, 5.01 mmol), para-nitrophenyldichlorophosphate (1.362 g, 5.01 mmol), and TEA (1.4 mL, 10.02 mmol) in DCM (40 mL), to yield 1.669 g (90%) of crude product used without further purification.

$^{31}$P-NMR (CDCl$_3$, 121 MHz): δ 7.95.

$^1$H-NMR (CDCl$_3$; 300 MHz): δ 8.1 (2H, 2d, $^3$J=8 Hz, O Ph), 7.28 (2H, 2d, $^3$J=8 Hz OPh), 4.8 (1H, bs, NH), 4.2 (2H, 2q, $^3$J=7.1 Hz, OCH$_2$CH$_3$), 2.2-2.0 (4H, m, 4H cyclopentane), 1.95-1.7 (4H, m, 4H cyclopentane), 1.27 (3H, t, $^3$J=7.1 Hz, OCH$_2$CH$_3$).

$^{13}$C-NMR (CDCl$_3$; 75 MHz): δ 14.4 (CH$_3$CH$_2$), 24.4 (2CH$_2$ cyclopent), 38.8, 38.7 (2CH$_2$ cyclopent), 62.4 CH$_3$CH$_2$), 68.5 (Cq cyclopentane), 121.8, 121.1 ('o' OPh), 126.1, 125.9 ('m', OPh), 145.6 ('ipso', OPh), 154.8 ('p', OPh), 174.9 (COOCH$_2$CH$_3$).

Synthesis of p-nitrophenyl-(benzoxy-α,α-cycloleuci-nyl)-phosphorochloridate $C_{19}H_{20}ClN_2O_6P$, MW=438.80.

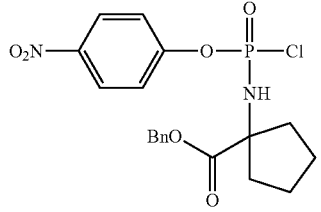

This is synthesised according to Standard procedure 4, using benzyl-1-amino-1-cyclopentanoate hydrochloride salt (0.835 g, 3.25 mmol), para-nitrophenyl-dichlorophosphate (0.85 g, 3.25 mmol), and TEA (0.91 mL, 6.7 mmol) in DCM (30 mL), to yield 1.215 g (85%) of crude product used without further purification.

$^{31}$P-NMR (CDCl$_3$, 121 MHz): δ 7.99, 7.90.

$^1$H-NMR (CDCl$_3$; 300 MHz): δ 8.1 (2H, 2d, $^3$J=8 Hz, O Ph), 7.4-7.2 (7H, m, OPh+CH$_2$Ph), 5.18 (2H, s, CH$_2$Ph), 5.0 (1H, bs, NH), 2.2-2.0 (4H, m, 4H cyclopentane), 1.95-1.75 (4H, m, 4H cyclopentane).

$^{13}$C-NMR (CDCl$_3$; 75 MHz): δ 24.4 (2CH$_2$ cyclopent), 38.8, 38.7, 38.6, 38.5 (2CH$_2$ cyclopent), 68.0 (CH$_2$Ph), 68.6 (Cq cyclopentane), 121.8, 121.7 ('o' OPh), 126.1, 125.9 ('m' OPh) 129.1, 129.0, 128.8, 128.6 (CH$_2$Ph), 135.7 ('ipso', CH$_2$Ph), 145.6 ('ipso', OPh), 154.8, 154.7 ('p', OPh), 174.5, 174.4 (COOCH$_2$Ph).

Synthesis of p-chlorophenyl-(methoxy-α,α-cyclo-
leucinyl)-phosphorochloridate $C_{13}H_{16}Cl_2NO_4P$, MW=352.15.

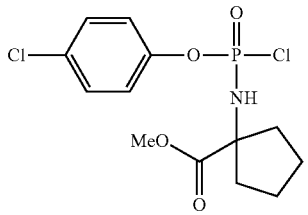

This is synthesised according to Standard procedure 4, using methyl-1-amino-1-cyclopentanoate hydrochloride salt (0.443 g, 2.5 mmol), para-chlorophenyldichlorophosphate (0.613 g, 2.5 mmol), and TEA (0.7 ml, 5 mmol) in DCM (20 mL), to yield 0.852 g (98%) of crude product used without further purification.

$^{31}$P-NMR (CDCl$_3$, 121 MHz): δ 9.55, 9.5.

$^1$H-NMR (CDCl$_3$; 300 MHz): δ 7.35-7.15 (4H, m, OPh), 4.95 (1H, bs, NH), 3.78 (3H, s, OCH$_3$), 2.2-2.00 (4H, m, 4H cyclopentane), 1.95-1.7 (4H, m, 4H cyclopentane).

$^{13}$C-NMR (CDCl$_3$; 75 MHz): δ 24.3 (2CH$_2$ cyclopent), 38.7 (2CH$_2$ cyclopent), 53.3 (CH$_3$O), 68.6 (Cq cyclopentane), 122.0 ('o' OPh), 130.1 ('m', OPh), 133.2 ('p', OPh), 149.9 ('ipso', OPh), 175.1-175.0 (COOCH$_3$).

Synthesis of p-chlorophenyl-(ethoxy-α,α-cycloleuci-
nyl)-phosphorochloridate $C_{14}H_{18}Cl_2NO_4P$, MW=366.18.

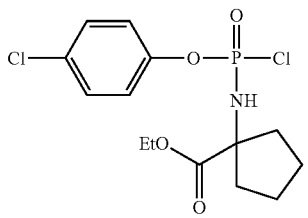

This is synthesised according to Standard procedure 4, using ethyl-1-amino-1-cyclopentanoate hydrochloride salt (0.477 g, 2.5 mmol), para-chlorophenyldichlorophosphate (0.613 g, 2.5 mmol), and TEA (0.7 mL, 5 mmol) in DCM (20 mL), to yield 0.880 g (97%) of crude product used without further purification.

$^{31}$P-NMR (CDCl$_3$, 121 MHz): δ 9.85, 9.70.

$^1$H-NMR (CDCl$_3$; 300 MHz): δ 7.35-7.15 (4H, m, OPh), 4.9 (1H, bs, NH), 4.22 (2H, 2q, $^3$J=7.1 Hz, OCH$_2$CH$_3$), 2.2-2.0 (4H, m, 4H cyclopentane), 1.95-1.7 (4H, m, 4H cyclopentane), 1.27 (3H, t, $^3$J=7 Hz, OCH$_2$CH$_3$.

$^{13}$C-NMR (CDCl$_3$; 75 MHz): δ 14.4 (CH$_3$CH$_2$), 24.4 (2CH$_2$ cyclopent), 38.8, 38.7 (2CH$_2$ cyclopent), 62.5, 62.4 CH$_3$CH$_2$), 68.1 (Cq cyclopentane), 122.2, 122.1 ('o' OPh), 130.1 ('m', OPh), 133.2 ('p', OPh), 149.8 ('ipso', OPh), 174.8 (COOCH$_2$CH$_3$).

Synthesis of p-chlorophenyl-(benzoxy-α,α-cyclo-
leucinyl)-phosphorochloridate $C_{19}H_{20}Cl_2NO_4P$, MW=428.25.

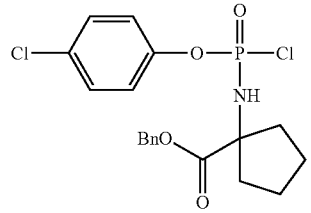

This is synthesised according to Standard procedure 4, using benzyl-1-amino-1-cyclopentanoate hydrochloride salt (0.640 g, 2.5 mmol), para-chlorophenyl-dichlorophosphate (0.613 g, 2.5 mmol), and TEA (0.7 mL, 5 mmol) in DCM (20 mL), to yield 1.041 g (97%) of crude product used without further purification.

$^{31}$P-NMR (CDCl$_3$, 121 MHz): δ 9.39, 8.95.

$^1$H-NMR (CDCl$_3$; 300 MHz): δ 7.4-7.15 (9H, m, O Ph+CH$_2$Ph), 5.20 (2H, s, CH$_2$Ph), 5.0 (2H, s, CH$_2$Ph), 5.0 (1H, bs, NH), 2.2-2.0 (4H, m, 4H cyclopentane), 1.95-1.75 (4H, m, 4H cyclopentane).

$^{13}$C-NMR (CDCl$_3$; 75 MHz): δ 24.4 (2CH$_2$ cyclopent), 38.8, 38.7, 38.6 (2CH$_2$ cyclopent), 68.1, 68.0 (CH$_2$Ph), 68.2 (Cq cyclopentane), 121.9, 121.8 ('o' OPh), 130.5, 130.4, 129.3, 129.2 ('m'OPh, CH$_2$Ph), 133.2 ('p', OPh), 135.7 ('ipso', CH$_2$Ph), 149.9 ('ipso', OPh), 174.3, 174.2 (COOCH$_2$Ph).

Synthesis of p-trifluorophenyl-(methoxy-α,α-cyclo-
leucinyl)-phosphorochloridate $C_{14}H_{16}ClF_3NO_4P$, MW=385.70.

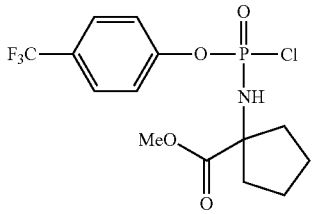

This is synthesised according to Standard procedure 4, using methyl-1-amino-1-cyclopentanoate hydrochloride salt (0.443 g, 2.5 mmol), para-trifluorophenyldichlorophosphate (0.700 g, 2.5 mmol), and TEA (0.7 ml, 5 mmol) in DCM (20 mL), to yield 0.931 g (97%) of crude product used without further purification.

$^{31}$P-NMR (CDCl$_3$, 121 MHz): δ 8.80, 8.62.

$^1$H-NMR (CDCl$_3$; 300 MHz): δ 7.65 (2H, 2d, $^3$J=8 Hz, O Ph), 7.35 (2H, 2d, $^3$J=8 Hz OPh), 5.02 (1H, bs, NH), 3.78 (3H, s, OCH$_3$), 2.25-2.05 (4H, m, 4H cyclopentane), 1.95-1.7 (4H, m, 4H cyclopentane).

$^{13}$C-NMR (CDCl$_3$; 75 MHz): δ 22.8 (2CH$_2$ cyclopent), 37.5, 37.2 (2CH$_2$ cyclopent), 51.5 (CH$_3$O), 68.4 (Cq cyclopentane), 120.0 ('o', OPh), 124.8 (d, J=270 Hz, CF$_3$), 126.6 ('m', OPh), 129.5 ('p',q, J=32 Hz, OPh), 152.8 ('ipso', OPh), 175.2 (COOCH$_3$).

Synthesis of p-trifluorophenyl-(ethoxy-α,α-cyclo-leucinyl)-phosphorochloridate $C_{15}H_{18}ClF_3NO_4P$, MW=399.73.

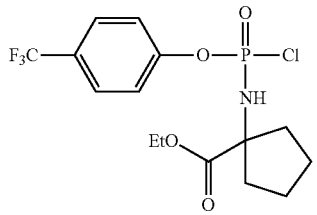

This is synthesised according to Standard procedure 4, using ethyl-1-amino-1-cyclopentanoate hydrochloride salt (0.477 g, 2.5 mmol), para-trifluorophenyldichlorophosphate (0.700 g, 2.5 mmol), and TEA (0.7 mL, 5 mmol) in DCM (20 mL), to yield 0.950 g (89%) of crude product used without further purification.

$^{31}$P-NMR (CDCl$_3$, 121 MHz): δ 8.49.

$^1$H-NMR (CDCl$_3$; 300 MHz): δ 7.45 (2H, m, OPh), 7.2 (2H, m, OPh), 5.12 (1H, bs, NH), 4.05 (2H, m, OCH$_2$CH$_3$), 2.15-2.0 (4H, m, 4H cyclopentane), 1.9-1.65 (4H, m, 4H cyclopentane), 1.2 (3H, 2t, $^3$J=7 Hz, OCH$_2$CH$_3$.

$^{13}$C-NMR (CDCl$_3$; 75 MHz): δ 14.3 (CH$_3$CH$_2$), 24.2, 24.1 (2CH$_2$ cyclopent), 38.6, 38.5, 38.4 (2CH$_2$cyclopent), 62.0 CH$_3$CH$_2$), 68.4 (Cq cyclopentane), 121.5 ('o', OPh), 125.0 (d, J=270 Hz, CF$_3$), 127.5 ('m', OPh), 129.9 ('p',q, J=32 Hz, OPh), 152.8, 152.7 ('ipso', OPh), 174.9, 174.6 (COOCH$_2$CH$_3$).

Synthesis of p-trifluorophenyl-(benzoxy-α,α-cyclo-leucinyl)-phosphorochloridate $C_{20}H_{20}ClF_3NO_4P$, MW=461.80.

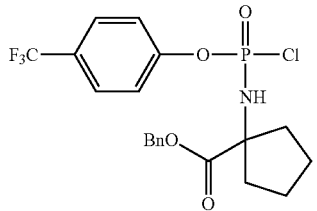

This is synthesised according to Standard procedure 4, using benzyl-1-amino-1-cyclopentanoate hydrochloride salt (0.700 g, 2.73 mmol), para-trifluorophenyl-dichlorophosphate (0.75 g, 2.73 mmol), and TEA (0.75 mL, 5.47 mmol) in DCM (25 mL), to yield 1.089 g (86%) of crude product used without further purification.

$^{31}$P-NMR (CDCl$_3$, 121 MHz): δ 9.39, 8.95.

$^1$H-NMR (CDCl$_3$; 300 MHz): δ 7.50 (2H, m, OPh), 7.4-7.15 (7H, m, OPh+CH$_2$Ph), 5.20 (2H, s, CH$_2$Ph), 4.95 (1H, bs, NH), 2.2-2.0 (4H, m, 4H cyclopentane), 1.95-1.75 (4H, m, 4H cyclopentane).

$^{13}$C-NMR (CDCl$_3$; 75 MHz): δ 24.3 (2CH$_2$ cyclopent), 38.8, 38.7, 38.6 (2CH$_2$ cyclopent), 68.1, 68.0 (CH$_2$Ph), 68.2 (Cq cyclopentane), 121.4, 121.3 ('o', OPh), 125.1 (d, J=270 Hz, CF$_3$), 126.6 ('m', OPh) 129.2, 128.8, 127.8 (Bn), 129.8 ('p',q, J=32 Hz, OPh), 135.7 ('ipso', CH$_2$Ph), 153.5 ('ipso', OPh), 174.5, 174.4 (COOCH$_2$Ph).

Synthesis of Phenyl-(methoxy-L-phenylalaninyl)-phosphorochloridate $C_{16}H_{17}ClNO_4P$, MW=353.74.

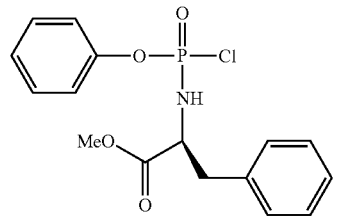

This is synthesised according to Standard procedure 4, using L-phenylalanine methyl ester hydrochloride (1.08 g, 5 mmol), phenyldichlorophosphate (1.12 g, 0.75 ml, 5 mmol), and TEA (1.4 ml, 10 mmol) in DCM (40 mL), to yield 1.626 g (92%) of crude product used without further purification.

$^{31}$P-NMR (CDCl$_3$, 121 MHz): δ 9.1, 8.95.

$^1$H-NMR (CDCl$_3$; 300 MHz): δ 7.3-7.1 (10H, m, CH$_2$Ph+OPh), 5.00 (1H, bs, NH), 4.35 (1H, m, CHphenylala), 3.79 (3H, 2s, CH$_3$O), 3.00 (2H, m, CH$_2$Ph)

$^{13}$C-NMR (CDCl$_3$; 75 MHz): δ 36.3 (CH$_2$phenylalanine), 53.0 (CH$_3$O), 56.6, 56.5 (CHphenylala), 121.0 ('o' OPh), 126.4 ('p', OPh), 130.2 ('m', OPh), 150.2 ('ipso', OPh), 174.1 (COOCH$_3$).

Synthesis of Phenyl-(methoxy-L-leucinyl)-phosphorochloridate $C_{13}H_{19}ClNO_4P$, MW=319.72

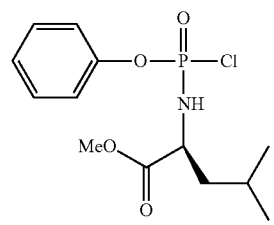

This is synthesised according to Standard procedure 4, using L-leucine methyl ester hydrochloride (0.91 g, 5 mmol), phenyldichlorophosphate (1.12 g, 0.75 ml, 5 mmol), and TEA (1.4 ml, 10 mmol) in DCM (40 mL), to yield 1.58 g (99%) of crude product used without further purification.

$^{31}$P-NMR (CDCl$_3$, 121 MHz): δ 9.45. 9.35.

$^1$H-NMR (CDCl$_3$; 300 MHz): δ 7.4-7.2 (5H, m, OPh), 4.90 (1H, bs, NH), 3.95 (1H, m, CHCH$_2$CH(CH$_3$)$_2$), 3.78 (3H, s, OCH$_3$), 1.8 (1H, m, CHCH$_2$CH(CH$_3$)$_2$), 1.8-1.5 (2H, m, CHCH$_2$CH(CH$_3$)2), 1.0-0.9 (6H, m, CHCH$_2$CH(CH$_3$)$_2$).

$^{13}$C-NMR (CDCl$_3$; 75 MHz): δ 23.2, 23.1, 22.4, 22.3 (2C, CHCH$_2$CH(CH$_3$)$_2$), 24.9, 24.8 (CHCH$_2$CH(CH$_3$)$_2$), 43.6 (CHCH$_2$CH(CH$_3$)$_2$), 53.2 (CH30), 53.7, 53.6 (CHCH$_2$CH ($CH_3$)$_2$), 120.9 ('o' OPh), 126.4 ('p', OPh), 130.2 ('m', OPh), 150.1 ('ipso', OPh), 173.6 ($\underline{C}OOCH_3$).

Synthesis of Phenyl-(benzoxy-L-leucinyl)-phosphorochloridate. $C_{19}H_{23}ClNO_4P$, MW=395.82

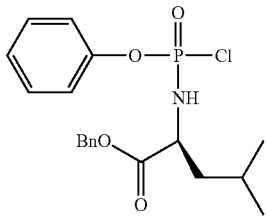

This is synthesised according to Standard procedure 4, using L-leucine benzyl ester hydrochloride (1.29 g, 5.0 mmol), phenyl-dichlorophosphate (1.12 g, 0.75 ml, 5.0 mmol), and TEA (1.4 mL, 10.0 mmol) in DCM (40 mL), to yield 1.88 g (95%) of crude product used without further purification.

$^{31}$P-NMR (CDCl$_3$, 121 MHz): δ 9.93, 9.57.

$^1$H-NMR (CDCl$_3$; 300 MHz): δ 7.5-7.2 (10H, m, O Ph+CH$_2$Ph), 5.2 (2H, 2s, CH$_2$Ph), 4.95 (1H, bs, NH), 4.2-4.1 (1H, m, $\overline{C}HCH_2CH(CH_3)_2$), 1.95-1.80 (1H, m, $\overline{C}HCH_2CH(CH_3)_2$), 1.7 (2H, m, CHCH$_2$CH(CH$_3$)$_2$), 1.0-0.9 (6H, m, CHCH$_2$CH(CH$_3$)$_2$).

$^{13}$C-NMR (CDCl$_3$; 75 MHz): δ 23.2, 23.1, 22.4, 22.3 (2C, CHCH$_2$CH(CH$_3$)$_2$), 24.9 (CHCH$_2$CH(CH$_3$)$_2$), 43.5 (CHCH$_2$CH(CH$_3$)$_2$), 53.8, 53.3 (CHCH$_2$CH(CH$_3$)$_2$), 67.8, 67.7 (CH$_2$Ph), 120.7 ('o' OPh), 126.4 ('p', OPh), 130.2, 129, 1, 128.8, 128.7 ('m'OPh, CH$_2$Ph), 135.8 ('ipso', CH$_2$Ph), 150.2 ('ipso', OPh), 174.1 ($\underline{C}O\overline{O}CH_2Ph$).

Synthesis of p-nitrophenyl-(benzoxy-L-leucinyl)-phosphorochloridate. $C_{19}H_{22}ClN_2O_6P$, MW=440.81

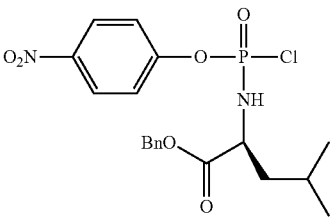

This is synthesised according to Standard procedure 4, using L-leucine benzyl ester hydrochloride (1.08 g, 5.01 mmol), para-nitrophenyl-dichloro phosphate (1.362 g, 5.01 mmol), and TEA (1.4 mL, 1.4 mmol) in DCM (40 mL), to yield 2.08g (95%) of crude product used without further purification.

$^{31}$P-NMR (CDCl$_3$, 121 MHz); δ 9.87, 9.38.

$^1$H-NMR (CDCl$_3$; 300 MHz): δ 8.25-8.10 (2H, m, OPh), 7.35-7.25 (7H, m, OPh+CH$_2$Ph), 5.15 (2H, 2s, CH$_2$Ph), $\overline{4.95}$ (1 H, bs, NH), 4.15 ($\overline{1H}$, m, $\overline{C}HCH_2CH(CH_3)_2$), $\overline{1.95}$ (1H, m, CHCH$_2$C$\overline{H}$(CH$_3$)2), 1.7 (2H, m, CHCH$_2$CH(CH$_3$)2), 1.0-0.9 (6H, m, CHCH$_2$CH(CH$_3$)$_2$).

$^{13}$C-NMR (CDCl$_3$; 75 MHz): δ 23.2, 23.1, 22.1, 22.0 (2C, CHCH$_2$CH(CH$_3$)$_2$), 24.8 (CHCH$_2$CH(CH$_3$)$_2$), 43.4, 43.3 (CHCH$_2$CH(CH$_3$)$_2$), 54.2, 53.9 (CHCH$_2$CH(CH$_3$)$_2$), 68.0 67.9 (CH$_2$Ph), 121.6 ('o' OPh), 126.2, 126.1 ('m'OPh), 129.2, 129.0 (CH$_2$Ph), 135.4, 135.3 ('ipso', CH$_2$Ph), 145.8, 145.7 ('ipso', OP$\overline{h)}$, 154.7, 154.5 ('p', OPh), 173.0, 172.8 ($\underline{C}OOCH_2Ph$).

Synthesis of pchlorophenyl-(benzoxy-L-leucinyl)-phosphorochloridate. $C_{19}H_{22}Cl_2NO_4P$, MW=430.26

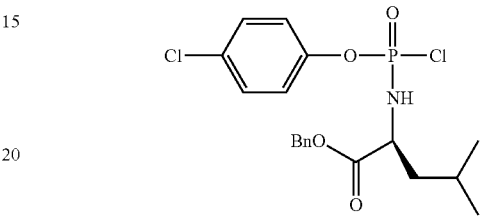

This is synthesised according to Standard procedure 4, using L-leucine benzyl ester hydrochloride (0.644 g, 2.5 mmol), para-chlorophenyl-dichlorophosphate (0.613 g, 2.5 mmol), and TEA (0.7 mL, 5 mmol) in DCM (20 mL), to yield 0.968 g (90%) of crude product used without further purification.

$^{31}$P-NMR (CDCl$_3$, 121 MHz): δ 9.71, 9.55.

$^1$H-NMR (CDCl$_3$; 300 MHz): δ 7.4-7.0 (9H, m, OPh+CH$_2$ Ph), 5.15 (2H, s, CH$_2$Ph), 4.5 (1H, d, 3J=7 Hz, NH), $\overline{4.0}$ (1H, m, CHCH$_2$CH($\overline{CH_3}$)$_2$), 1.9-1.8 (1H, m, CHCH$_2\overline{C}$H(CH$_3$)$_2$), 1.7 (2H, m, CHCH$_2$CH(CH$_3$)$_2$), 0.85 (6H, m, CHCH$_2$CH (CH$_3$)$_2$).

$^{13}$C-NMR (CDCl$_3$; 75 MHz): δ 23.4, 23.3, 22.5, 22.4 (2C, CHCH$_2$CH(CH$_3$)$_2$), 25.0 (CHCH$_2$CH(CH$_3$)$_2$), 43.8, 43.7 (CHCH$_2$CH(CH$_3$)$_2$), 54.0, 53.8 (CHCH$_2$CH(CH$_3$)$_2$), 68.2 ( CH$_2$Ph), 122.5 ('o' OPh), 130.5, 130.4, 129.3, 129.2 ('m'OPh, CH$_2$Ph), 133.2 ('p', OPh), 135.7 ('ipso', CH$_2$Ph), 149.9, 149.8 ('ipso', OPh), 173.4, 173.2 ($\underline{C}OOCH_2Ph$).

Synthesis of 4-chlorophenyl-(methyl-2-amino-2-methylpropanoate)-phosphorochloridate. $C_{11}H_{14}Cl_2NO_4P$, MW=326.11

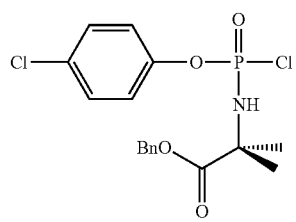

This is synthesised according to Standard procedure 4, using 2-aminoisobutyrate methyl ester hydrochloride (280.0 mg, 1.82 mmol), 4-chlorophenylphosphodichloride (447.4 mg, 1.82 mmol), and TEA (368.3 mg, 3.64 mmol, 507.3 µL) in DCM (20 mL), to yield 554 mg (yield 91.1%) of crude product used without further purification.

$^{31}$P-NMR (CDCl$_3$, 121 MHz): δ 7.05 (s)

$^{1}$H-NMR (CDCl$_3$; 300 MHz): δ 7.38 (2H, d, $^3$J=9.0 Hz, OPh), 7.29-7.24 (2H, 2d, $^3$J=9.0 Hz, OPh), 4.87-4.83 (1H, 2bs, NH) 3.84 (3H, s, OCH$_3$), 1.73-1.71 (6H, 2s, [CH$_3$]$_2$C)

$^{13}$C-NMR (CDCl$_3$; 75 MHz): δ 27.0, 27.3, ([CH$_3$]$_2$C), 53.7 (OCH$_3$), 58.9 (C[CH$_3$]$_2$), 122.5 ('o', OPh), 129.7 ('m', OPh), 131.8 ('p', OPh) 148.7, 148.9 ('ipso', OPh), 175.5, 175.7 (COOCH$_3$).

Synthesis of 4-chlorophenyl-phosphodichloridate.
C$_6$H$_4$Cl$_3$O$_2$P, MWW=245.43

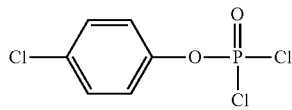

This was synthesised according to Standard procedure 3, using phosphorus-oxychloride 1533 mg, 10.00mmol, 932 μL), 4-chlorophenol (1.285 g, 10.00 mmol) and TEA (1.011 g, 0.00 mmol, 1394 μL) in ethylether (100 mL) to give an oil (1.897 g, 77.3% yield).

$^{31}$P-NMR (CDCl$_3$, 121 MHz): δ 5.18.

$^{1}$H-NMR (CDCl$_3$; 300 MHz): δ 7.45 (2H, d, 3J=9.0 Hz, OPh), 7.30 (2H, d, $^3$J=9.0 Hz, OPh).

$^{13}$C-NMR (CDCl$_3$; 75 MHz): δ 122.5 ('o', OPh), 130.6 ('m', OPh), 133.2 ('p', OPh), 148.5 ('ipso', OPh).

Synthesis of 4-(trifluoromethyl)-phenyl-phosphodichloridate. C$_7$H$_4$ClF$_3$O$_3$P, MW=278.98

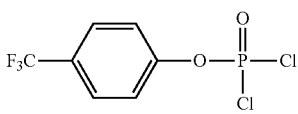

This was synthesised according to Standard procedure 3, using phosphorus-oxychloride (1.570 mg, 10.24 mmol, 954.5 μL), 4-trifluoromethylphenol (1660 g, 10.24 mmol) and TEA (1.036 g, 10.24 mmol, 1427 μL) in ethylether (100 mL) to give an oil (2.521 g, 88.2% yield).

$^{31}$P-NMR (CDCl$_3$, 121 MHz): δ 4.75.

$^{1}$H-NMR (CDCl$_3$; 300 MHz): δ 7.77 (2H, d, 3J8.4 Hz, OPh), 7.49 (2H, d, $^3$J=8.4 Hz, $^{13}$C-NMR (CDCl$_3$; 75 MHz): δ 121.6 ('o', OPh), 123.6 (CF$_3$, J=271 Hz, OPh), 128.2 ('m', OPh), 129.7 ('p', J=33 Hz), 152.7 ('ipso', OPh).

Synthesis of 4-fluorophenyl-phosphodichloridate.
C$_6$H$_4$Cl$_2$FO$_2$P, MW=228.97

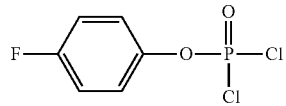

This was synthesised according to Standard procedure 3, using phosphorus-oxychloride (1.395 mL, 15.00 mmol), 4-chlorophenol (1.68 g, 15.00 mmol) and TEA (2.1 mL, 15.00 mmol) in ethylether (140 mL) to give an oil (3.96 g, 96% yield).

$^{31}$P-NMR (CDCl$_3$, 121 MHz): δ 5.52.

$^{1}$H-NMR (CDCl$_3$; 300 MHz): δ 7.15 (2H, d, 3J=8.0 Hz, OPh), 7.05 (2H, d, 3J=8.0 Hz, OPh).

$^{13}$C-NMR (CDCl$_3$; 75 MHz): δ 116.8 ('o', OPh), 122.1 ('m', OPh), 146.7 ('p', OPh), 158.7 ('ipso', OPh).

Experimental data are given in Table I illustrating the activity of compounds embodying the present invention, and of some comparative compounds, with respect to human breast cancer cell line NDA MB231, human colon cancer cell line HT115 and human prostrate cancer cell line PC-3. The compounds include those whose preparations are described above and compounds made by preparative methods corresponding to the methods described above.

The experimental procedures used human colon cancer cell line (HT115), human prostate cancer cell line (PC-3), human breast cancer cell line (MDA MB 231) and normal human umbilical vein endothelial cell (HUVEC). Compounds were diluted over a range of concentrations and added to cells over 1 to 3 days. The cytotoxity was determined using a MTT assay at the end of each experiment.

In the Table:

ArO refers to Ar as defined above with respect to formula I;

J refers to the moiety of the present compounds represented by, respectively, ROCOCR'R"NH—, as defined above with respect to formula I, or, with respect to Examples 51, 52 and 53, HOCOCR'R"NH—, as defined above with respect to formula II; and B refers to the base moiety of the present compounds as defined above with respect to formula I or formula II.

BVU stands for 2-bromovinyl uridine.

5-(C═CC[O]O)MeU stands for methyl propenoate-2'-deoxyuridine.

GemCyt stands for Gemcitabine.

Examples A, 1, 67 and G are comparative Examples.

Example A is 5-(2-Bromovinyl)-2'-deoxyuridine.

Example 1 is Example 1 above corresponding to compound (7) above.

Example 67 is propenate-2'-deoxyuridine.

Example G is gemcitabine.

Examples 51, 52 and 53 are compounds embodying formula II above.

| Ex | ArO | J | B | EC50/μM Breast MDA MB231 | EC50/μM Colon HT115 | EC50/μM Prostate PC-3 |
|---|---|---|---|---|---|---|
| A | — | — | BVU | 125 | 78.7 | 120 |
| 1 | PhO | MeAlaNH | BVU | 79 | 244.5 | 155 |
| 2 | PhO | BnAlaNH | BVU | 34 | 1.4 | 19 |
| 3 | PhO | EtAlaNH | BVU | 56 | 52 | 36 |
| 4 | p-CF3PhO | BnAlaNH | BVU | 31 | 7.4 | 9.3 |
| 5 | p-FPhO | MeAlaNH | BVU | 159 | 17 | 58 |
| 6 | p-FPhO | EtAlaNH | BVU | 46 | 11 | 42 |
| 7 | p-FPhO | BnAlaNH | BVU | 17 | 3.5 | 16 |
| 8 | p-NO2PhO | BnAlaNH | BVU | 28 | — | 9 |
| 9 | p-NO2PhO | EtAlaNH | BVU | 177 | 118.7 | 365 |
| 10 | p-NO2PhO | MeAlaNH | BVU | 105 | 96.7 | 10.4 |
| 11 | p-ClPhO | EtAlaNH | BVU | 28.7 | 14.9 | 3.4 |
| 12 | p-ClPhO | BnAlaNH | BVU | 6.2 | 3.4 | 2.4 |
| 13 | p-ClPhO | MeAlaNH | BVU | 61 | 70.2 | 13 |
| 14 | PhO | Bn(Me2Gly)NH | BVU | 19 | 14.5 | 5.1 |
| 15 | p-CF3PhO | MeAlaNH | BVU | 47 | 79.2 | 15 |
| 16 | PhO | Me(cPntGly)NH | BVU | 79 | 77 | 16 |
| 17 | PhO | Et(cPntGly)NH | BVU | 44 | 81.3 | 41 |
| 18 | PhO | Bn(cPntGly)NH | BVU | 78 | 9.7 | 33 |
| 19 | p-NO2PhO | Me(cPntGly)NH | BVU | 56 | 38.2 | 88 |
| 20 | p-NO2PhO | Et(cPntGly)NH | BVU | 13 | 57.3 | 15 |
| 21 | p-NO2PhO | Bn[cPntGly]NH | BVU | 8.4 | 17.2 | 2.2 |
| 22 | PFPhO | Me[cPntGly]NH | BVU | 57 | 59.7 | 51 |
| 23 | PFPhO | Et[cPntGly]NH | BVU | 9.9 | 18.1 | 2.7 |
| 24 | PFPhO | Bn[cPntGly]NH | BVU | 9.4 | 17 | 3.7 |
| 25 | p-CF3PhO | EtAlaNH | BVU | 33.8 | | 4.6 |
| 26 | PhO | Me(Me2Gly)NH | BVU | 41.1 | 77.9 | 1.5 |
| 27 | PhO | Et(Me2Gly)NH | BVU | 217.9 | 39.7 | 76.1 |
| 28 | p-CF3PhO | Me(cPntGly)NH | BVU | 28.8 | 21.2 | — |
| 29 | p-CF3PhO | Et(cPntGly)NH | BVU | 45.6 | 15.1 | 4.3 |
| 30 | p-CF3PhO | Bn(cPntGly)NH | BVU | 6.9 | 6.4 | — |
| 32 | p-ClPhO | Me(cPntGly)NH | BVU | 2.6 | 99.3 | 52.2 |
| 33 | p-ClPhO | Et[cPntGly]NH | BVU | 12 | 97.9 | 83.2 |
| 34 | p-ClPhO | Bn[cPntGly]NH | BVU | 3.9 | 8.9 | 6.3 |
| 35 | PhO | MeLeuNH | BVU | 18.5 | 7.7 | 75.7 |
| 36 | PhO | Me[Phe]NH | BVU | 19.8 | 32.1 | 86.9 |
| 37 | PhO | BnLeuNH | BVU | 2.8 | 7 | 7.16 |
| 38 | p-NO2PhO | BnLeuNH | BVU | 6.3 | 10.7 | 7.2 |
| 39 | p-ClPhO | BnLeuNH | BVU | 4.3 | 288.5 | 193.1 |
| 42 | p-ClPhO | Me(Me2Gly)NH | BVU | 8.7 | 183.4 | 441.6 |
| 43 | p-ClPhO | Et(Me2Gly)NH | BVU | 5.9 | 174.3 | 1.15 |
| 44 | p-ClPhO | Bn(Me2Gly)NH | BVU | 2.3 | 4.5 | 9.12 |
| 45 | p-NO2PhO | Me(Me2Gly)NH | BVU | 9.4 | 24.7 | 222.8 |
| 46 | p-NO2PhO | Et(Me2Gly)NH | BVU | 2 | 224 | 82.4 |
| 47 | p-NO2PhO | Bn(Me2Gly)NH | BVU | 4.5 | 16.7 | 27.2 |
| 48 | p-CF3PhO | Bn(Me2Gly)NH | BVU | 1.3 | 7 | 0.61 |
| 49 | o-ClPhO | BnAlaNH | BVU | 5.4 | 16.2 | 5.4 |
| 50 | o-ClPhO | Bn(Me2Gly)NH | BVU | 5.7 | 3.9 | 6.59 |
| 51 | — | L-AlaNH | BVU | 295.4 | | |
| 52 | — | LeuNH | BVU | 438.1 | | |
| 53 | — | PhAlaNH | BVU | 66 | | |
| 54 | PhO | Bn[PhAla]NH | BVU | 5.1 | | |
| 55 | PhO | Me[D-Ala]NH | BVU | 392.7 | | |
| 56 | PhO | Bn[D-Ala]NH | BVU | 20.8 | | |
| 57 | p-NO2PhO | Bn[D-Ala]NH | BVU | 20.2 | | |
| 58 | p-CF3 | Me[Me2Gly]NH | BVU | 83.6 | | |
| 59 | p-CF3 | Et[Me2Gly]NH | BVU | 24.7 | | |
| 60 | p-FPhO | Et[Me2Gly]NH | BVU | 86.8 | | |
| 61 | p-CF3PhO | Bn[L-PhAla]NH | BVU | 6.3 | | |
| 62 | p-CF3PhO | Bn[L-Leu]NH | BVU | 1.9 | | |
| 63 | PhO | tBu[L-Ala]NH | BVU | 31.5 | | |
| 64 | p-NO2PhO | Bn[L-PhAla]NH | BVU | 16.6 | | |
| 65 | p-FPhO | Me{Me2Gly)NH | BVU | | | |
| 66 | p-NO2PhO | Me(Me2Gly)NH | 5-(C≡CC[O]OMe)U | 20.7 | | |
| 67 | — | — | 5-(C≡CC[O]OMe)U | 93.7 | | |
| 69 | PhO | MeMetNH | BVU | — | — | 6.3 |
| 70 | PhO | MeTrpNH | BVU | — | — | 16 |
| 71 | PhO | BnMetNH | BVU | — | — | 6.3 |
| 72 | PhO | BnIleNH | BVU | — | — | 1.6 |
| 73 | PhO | EtIleNH | BVU | — | — | 30.6 |
| 74 | PhO | MeGlyNH | BVU | — | — | 31 |
| 75 | PhO | BnGlyNH | BVU | — | — | 29 |
| 77 | p-Cl PhO | BnGlyNH | BVU | — | — | 150 |

TABLE-continued

| Ex | ArO | J | B | EC50/μM Breast MDA MB231 | EC50/μM Colon HT115 | EC50/μM Prostate PC-3 |
|---|---|---|---|---|---|---|
| 78 | p-CF₃PhO | BnValNH | BVU | — | — | 1.6 |
| 80 | PhO | Me₂AspNH | BVU | — | — | 158 |
| 81 | PhO | Et₂GluNH | BVU | — | — | 31 |
| 82 | m-ClPhO | BnAlaNH | BVU | — | — | 21 |
| 83 | m-ClPhO | BnMe₂GlyNH | BVU | — | — | 6.3 |
| 84 | p-FphO | BnMe₂GlyNH | BVU | — | — | 4.5 |
| 85 | PhO | BnValNH | BVU | — | — | 31.2 |
| 86 | p-ClPho | BnValNH | BVU | — | — | 0.9 |
| 87 | p-FphO | BnValNH | BVU | — | — | 1.6 |
| 88 | PhO | BnPhGlyNH | BVU | — | — | 0.75 |
| 89 | p-ClPhO | BnPhGlyNH | BVU | — | — | 6.5 |
| 91 | p-CF₃PhO | BnPhGlyNH | BVU | — | — | 0.7 |
| 94 | PhO | i-BuAlaNH | BVU | — | — | 51 |
| 95 | PhO | 2-BuAlaNH | BVU | — | — | 6.8 |
| G | — | — | GemCyt | 2.8 | 606.1 | 3.12 |
| 31 | PhO | BnAlaNH | GemCyt | 42.6 | 5.7 | 0.22 |
| 40 | p-ClPhO | BuAlaNH | GemCyt | 9.2 | 16.1 | 15.4 |
| 41 | p-ClPhO | Bn[Me2Gly]NH | GemCyt | 3.1 | 317.1 | 68.8 |

Gemcitabine (Example G in the Table) and compound CPF31 (Example 31 in the Table: gemcitabine-[phenyl-(benzoxy-L-alaninyl)]-phosphate) were compared in a mouse model with xenografts of human cancer (colon HT115 and prostate PC3).

Mice were dosed daily at a range of concentrations (0.01-10 μM) and tumour volume assessed versus control.

Kaplan-Meier statistics were computed regarding incident-free survival.

Figure 1:
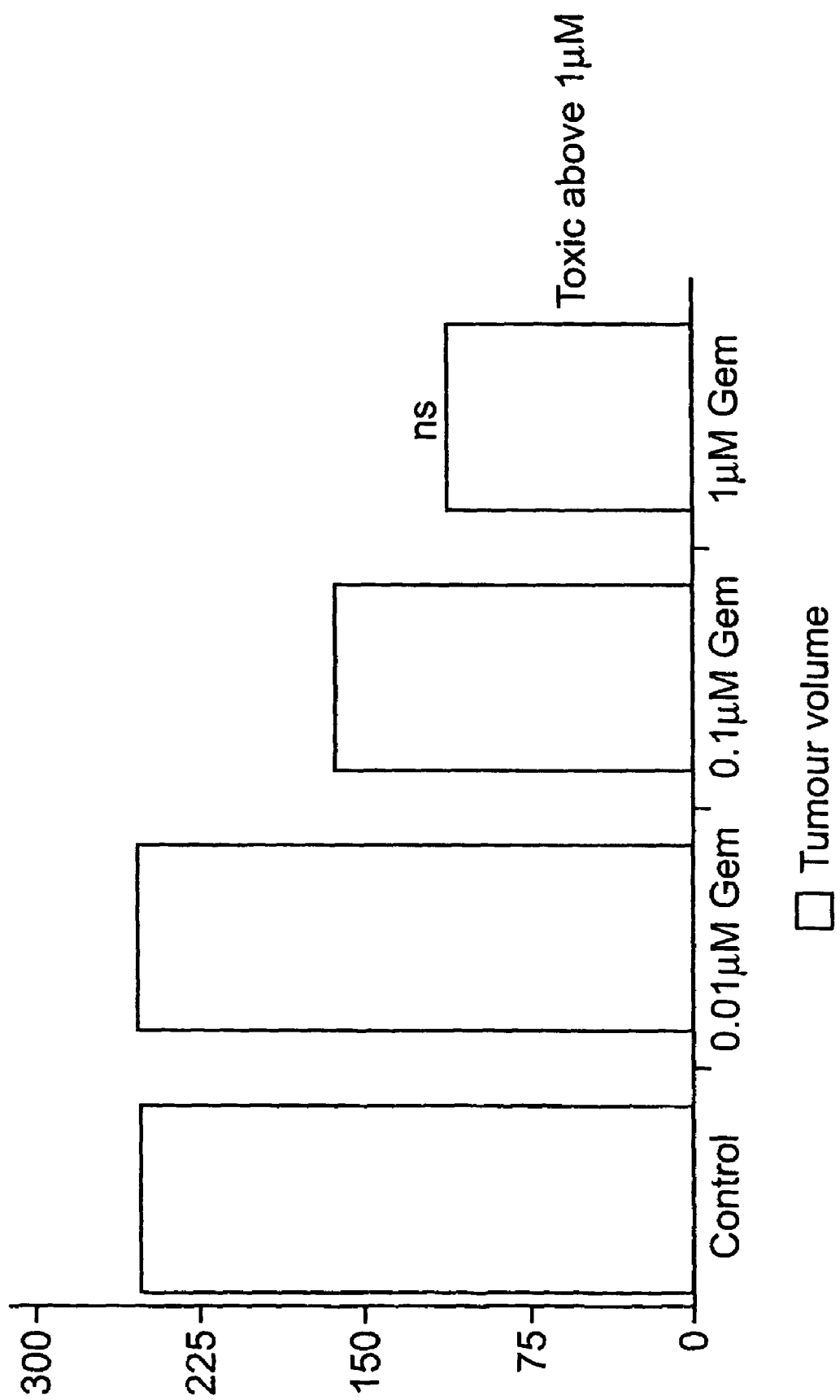
FIG. 1 shows for the mouse xenograft the tumour volume for prostate data at day 13 using Gemzar™ (gemcitabine available ex. Lilly)

Referring to the drawings, CPF31 can be seen to be significantly less toxic than gemcitabine.

CPF31 was significantly effective at reducing prostate and colon tumour volume relative to control at daily dosing of 5 and 10 μM (3 and 6 μg/ml). Gemcitabine was not effective at the highest non-toxic concentration.

Figure 2:
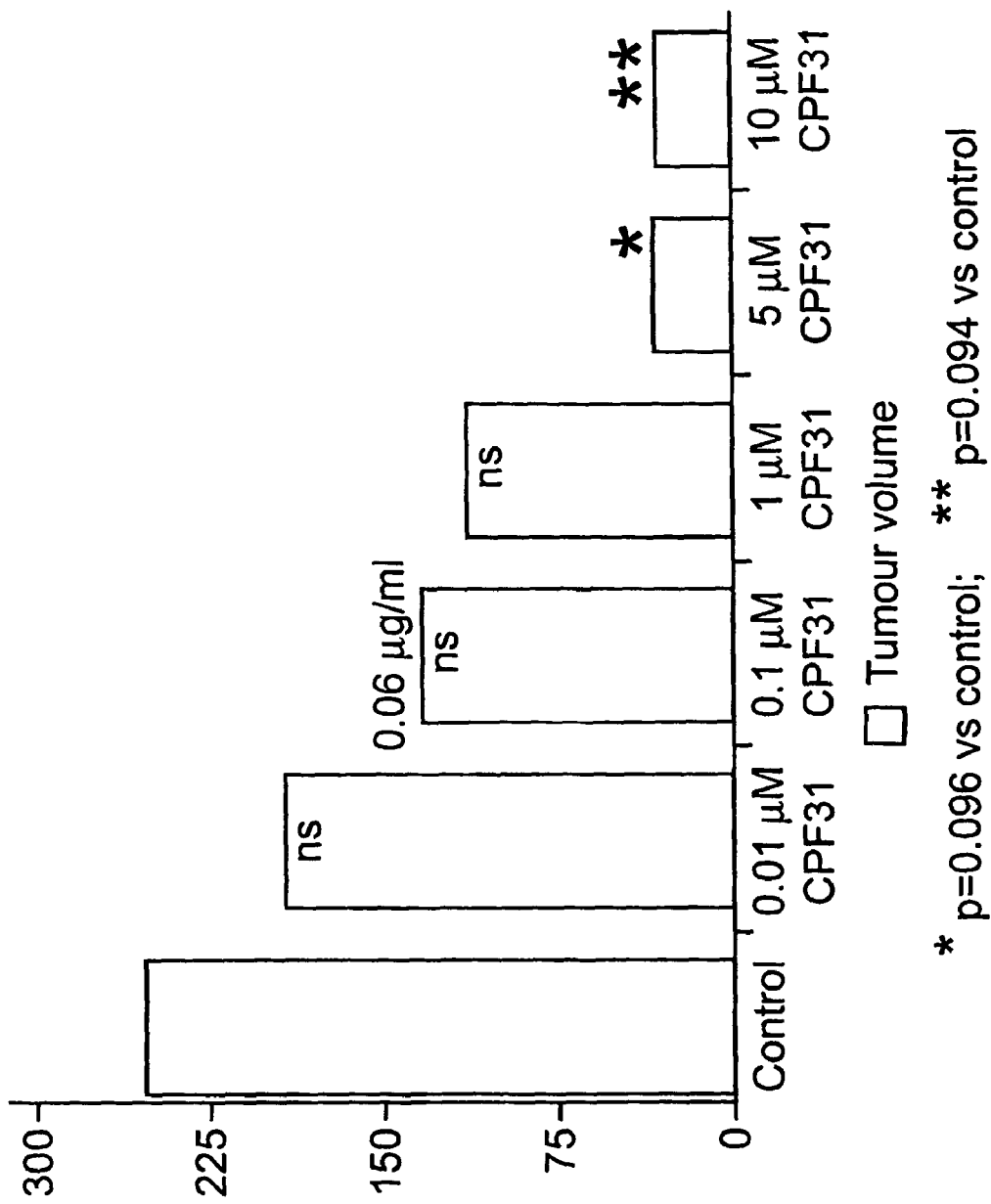
FIG. 2 shows for the mouse xenograft the tumour volume for prostate data at day 13 using CPF31.

Gemzar is seen from FIG. 1 to be toxic above 1 μM. In contrast, CPF31 is seen from FIG. 2 to have substantially lower toxicity.

Figure 3:
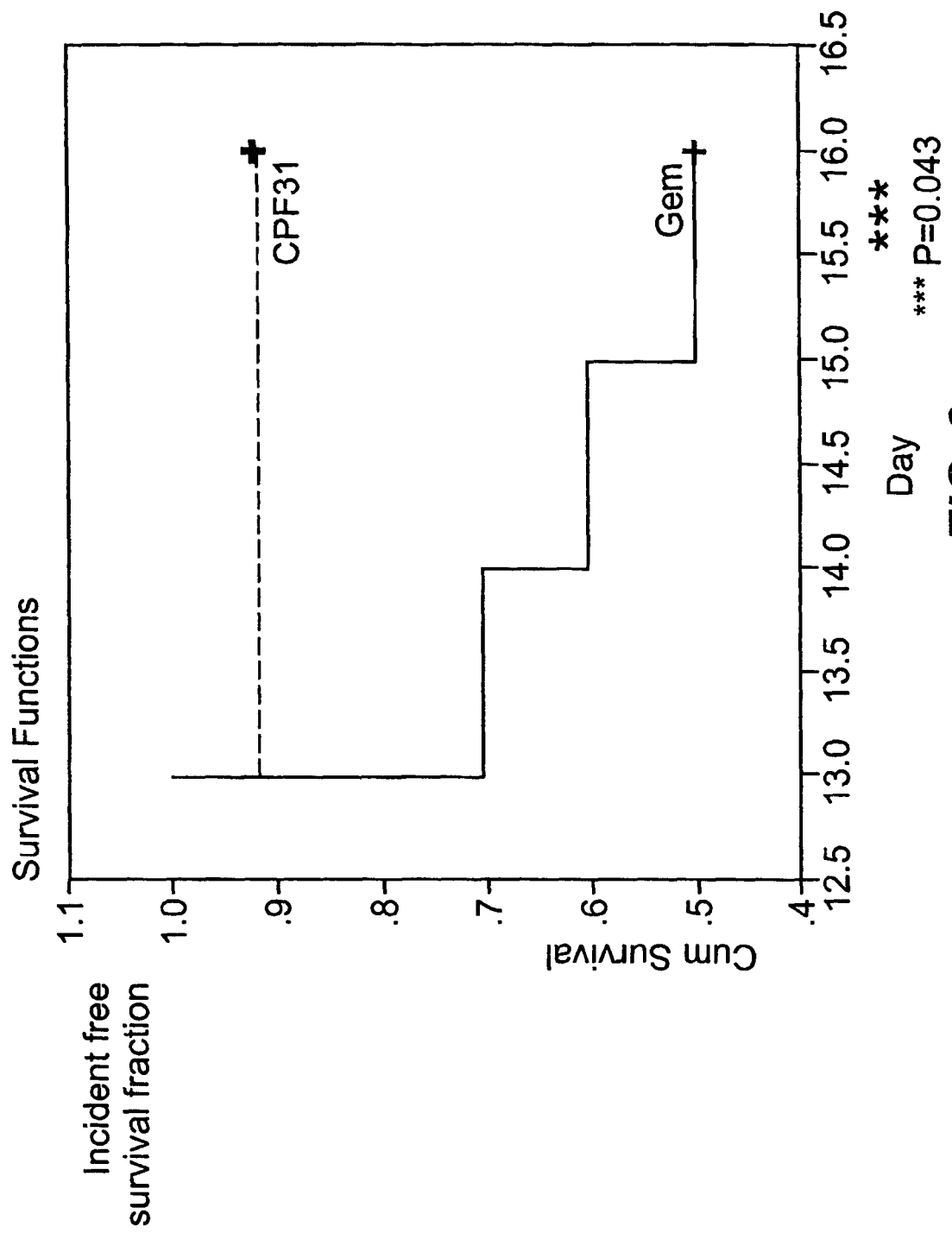
FIG. 3 shows the incident free survival functions v. day for each of CPF31 and gemcitabine.

FIG. 3 shows that CPF31 has significantly lower side effects on a comparable basis: 3 animals show serious toxicity (10% body mass loss) in GMZ and in CPF31 on day 10, collectively 4 in GMZ and 1 in CPF31 on day 11 and 5 in GMZ and 1 in CPF on day 13. Using Chi square analysis by combining 5 and 10 μM groups, the significance is p=0.193, 0,078 and 0.0289 on day 10, 11 and 13. It is clear that by day 13, CPF31 displayed signficantly less side effects, and the anti-cancer effects continue to exceed that of Gemzar.

FIG. 3 shows the Kaplan-Meier survival curve, incidence free survival: based on the loss according to weight loss. A Cox proportion analysis shows that CPF31 is far less toxic than GMZ based on the weight-loss calculated loss (p=0.043).

Figure 4:
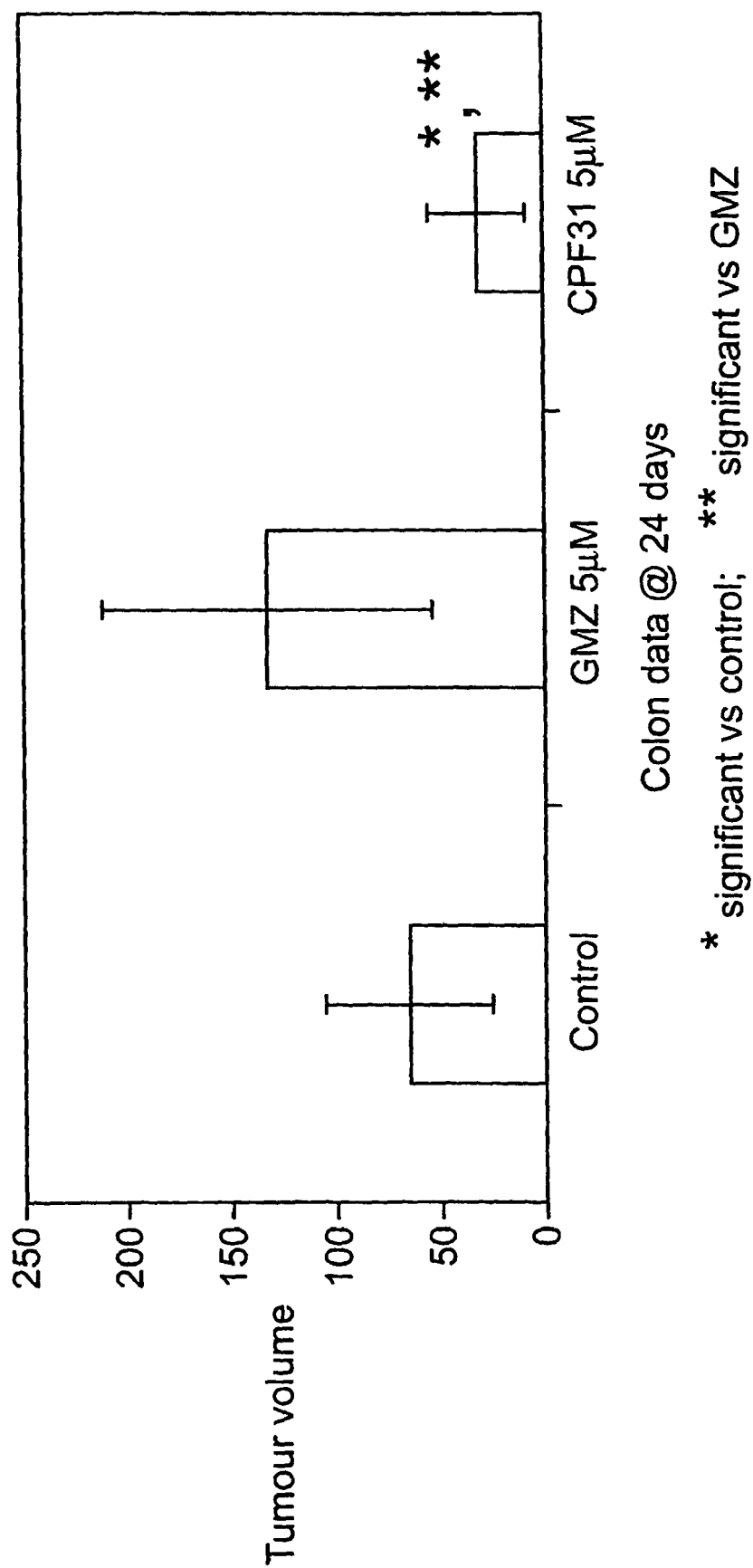
FIG. 4 shows for the mouse xenograft the tumour volume for colon data at day 24 using, respectively, Gemzar and compound CPF31.

CPF31 was found to be active at 5 μM in vitro, whereas Gemzar was found to be active at 600 μM, with respect to the same colon cell line. FIG. 4 shows the results of testing both in vivo at 5 μM. The greater activity of CPF31 in reducing tumour volume is shown in FIG. 4.

The invention claimed is:

1. A chemical compound having formula I:

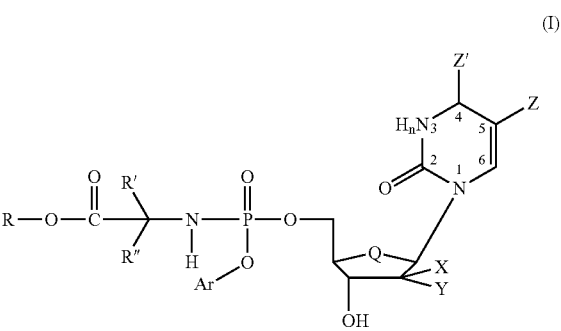

wherein:
R is selected from the group comprising alkyl, aryl and alkylaryl;
R' and R" are independently selected from the group comprising H, alkyl and alkylaryl, or
R' and R" together form an alkylene chain so as to provide, together with the C atom to which they are attached, a cyclic system;
Q is selected from the group comprising —O— and —CH₂—;
X and Y are independently selected from the group comprising H, halogen, OH and —CH₃;
Ar is a monocyclic aromatic ring moiety or a fused bicyclic aromatic ring moiety, either of which said ring moieties is carbocyclic or heterocyclic and is optionally substituted, any such substituent being selected from the group comprising halogen, halomethyl, oxo, hyroxy, carboxy, carboxyC₁₋₁₆ alkyl, alkoxy, alkoyl, alkoyloxy, aryloxy, aryloyl, aryloyloxy, amino, C₁₋₆alkylamino, diC₁₋₆alkylamino, cyano, azide, nitro, thiol, C₁₋₆ alkylthiol, sulphony, sulphoxide, heteocyclic groups, alkyl groups and aryl groups;

Z is H, n is 0,

Z' is —NH₂ and a double bond exists between position 3 and position 4, or a pharmaceutically acceptable derivative of a compound of formula I the derivative which upon administration to a recipient is capable of providing directly or indirectly a compound of formula I.

2. A compound according to claim 1 wherein R is selected from the group comprising a $C_{1-16}$ primary or secondary alkyl group, a $C_{5-7}$ carbocyclic aryl group or a $C_{1-6}alkylC_{5-11}$ aryl group.

3. A compound according to claim 2 wherein R is selected from the group $CH_3$, $—C_2H_5$ and $—CH_2C_6H_5$.

4. A compound according to claim 3 wherein R is $—CH_2C_6H_5$.

5. A compound according to claim 1 wherein Ar is an optionally substituted $C_6$ monocyclic aromatic ring moiety.

6. A compound according to claim 5 wherein Ar is selected from the group comprising $—C_6H_5$, $pCF_3C_6H_4—$, $pFC_6H_4—$, $pNO_2C_6H_4—$, $pClC_6H_4—$ and $oClC_6H_4—$.

7. A compound according to claim 1 wherein R' and R" are, independently, selected from the group comprising H, $C_{1-6}$ primary, secondary and tertiary alkyl, $C_{1-3}alkylC_{5-7}$ aryl, or, when together they form an alkylene chain, they provide, together with the C atom to which they are attached, a $C_{3-8}$ carbocyclic aliphatic ring.

8. A compound according to claim 7 wherein R' and R" are, independently, selected from the group comprising H, methyl, benzyl and $CH_2CH(CH_3)_2$, or, R' and R" together with the C atom to which they are attached, provide a $C_{5-6}$ ring.

9. A compound according to claim 8 wherein R' and R" are each methyl.

10. A compound according to claim 8 wherein one of R' and R" is H and one of R' and R" is methyl.

11. A compound according to claim 8 wherein R' and R", together with the C atom to which they are attached, provide a pentyl ring.

12. A compound according to claim 1 wherein R' and R" correspond to the side chains of a naturally occurring amino acid.

13. A compound according to claim 1 wherein Q is O.

14. A compound according to claim 1 wherein, each of X and Y is F.

15. A compound according to claim 1 wherein, X is OH and Y is H.

16. A compound according to claim 1 wherein, X is H and Y is OH.

17. A compound selected from the group comprising:
Gemcitabine-[phenyl-(benzoxy-L-alaninyl)]-phosphate;
Gemcitabine-[para-chlorophenyl-(benzoxy-L-alaninyl)]-phosphate and
Gemcitabine-[para-chlorophenyl-(benzoxy-α,α-dimethylglycinyl)]-phosphate.

18. A compound according to claim 1 for use in the treatment of cancer.

19. A method for the treatment of cancer comprising administration to a patient in need of such treatment an effective dose of a compound according to claim 1.

20. A pharmaceutical composition comprising a compound according to claim 1 with a pharmaceutically acceptable carrier, diluent or excipient.

21. A method of preparing a pharmaceutical composition comprising the step of combining a compound according to claim 1 with a pharmaceutically acceptable excipient, carrier or diluent.

22. A process for the preparation of a compound of formula I according to claim 1, the process comprising reacting of a compound of formula (III):

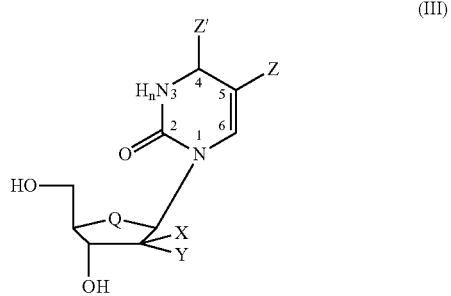

with a compound of formula (IV)

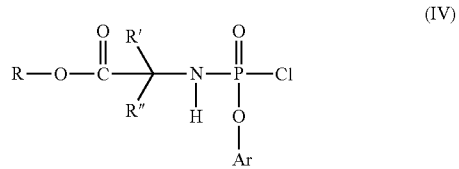

wherein Ar, n, Q, R, R', R", X, Y, Z and Z' " have the meanings described in claim 1 and a double bond exists between position 3 and position 4.

* * * * *